US009763982B2

(12) United States Patent
Jewett

(10) Patent No.: US 9,763,982 B2
(45) Date of Patent: Sep. 19, 2017

(54) DEPLETION OF CANCER STEM CELLS

(71) Applicant: THE REGENTS OF THE UNIVERSITY OF CALIFORNIA, Oakland, CA (US)

(72) Inventor: Anahid Jewett, Valencia, CA (US)

(73) Assignee: The Regents of the University of California, Oakland, CA (US)

( * ) Notice: Subject to any disclaimer, the term of this patent is extended or adjusted under 35 U.S.C. 154(b) by 60 days.

(21) Appl. No.: 14/637,235

(22) Filed: Mar. 3, 2015

(65) Prior Publication Data
US 2015/0238530 A1 Aug. 27, 2015

Related U.S. Application Data

(63) Continuation-in-part of application No. 13/135,222, filed on Jun. 29, 2011, now abandoned.

(60) Provisional application No. 61/398,681, filed on Jun. 29, 2010.

(51) Int. Cl.
A61K 35/00 (2006.01)
A61K 35/17 (2015.01)
A61K 31/337 (2006.01)
A61K 31/198 (2006.01)
A61K 45/06 (2006.01)
C12N 5/0783 (2010.01)
A61K 38/20 (2006.01)
A61K 38/21 (2006.01)
A61K 39/395 (2006.01)
C07K 16/28 (2006.01)
A61K 35/12 (2015.01)
A61K 39/00 (2006.01)

(52) U.S. Cl.
CPC ............ *A61K 35/17* (2013.01); *A61K 31/198* (2013.01); *A61K 31/337* (2013.01); *A61K 38/2013* (2013.01); *A61K 38/212* (2013.01); *A61K 39/3955* (2013.01); *A61K 45/06* (2013.01); *C07K 16/283* (2013.01); *C12N 5/0646* (2013.01); *A61K 35/12* (2013.01); *A61K 2039/577* (2013.01)

(58) Field of Classification Search
CPC ................................ A61K 35/12; A61K 35/17
See application file for complete search history.

(56) References Cited

U.S. PATENT DOCUMENTS

| | | |
|---|---|---|
| 7,670,611 B2 | 3/2010 | Cohen |
| 8,148,356 B2 | 4/2012 | Pavliv |
| 2004/0062764 A1 | 4/2004 | Neuwelt et al. |
| 2004/0161433 A1 | 8/2004 | Teshigawara et al. |
| 2009/0068141 A1 | 3/2009 | Parkhurst et al. |
| 2010/0305057 A1 | 12/2010 | Rathos et al. |
| 2011/0150902 A1 | 6/2011 | Markovic |

OTHER PUBLICATIONS

Miller et al. (Blood. Nov. 1, 1992; 80 (9): 2221-9).*
Salagianni et al. (J. Immunol. Mar. 15, 2011; 186 (6): 3327-35).*
Miller et al. (Blood. Apr. 15, 2005; 105 (8): 3051-7).*
Lundqvist et al. (Blood. Jun. 11, 2009; 113 (24): 6120-6127).*
Ysebaert et al. (Leukemia. Jul. 2010; 24 (7): 1310-6).*
Zhou et al. (Blood. Oct. 29, 2009; 114 (18): 3793-802).*
Prlic et al. (J. Exp. Med. Apr. 21, 2003; 197 (8): 967-76).*
Jamieson et al. (J. Immunol. Jan. 15, 2004; 172 (2): 864-70).*
Dudley et al. (Science. Oct. 25, 2002; 298 (5594): 850-4).*
Pietra et al. (Int. Immunol. Jul. 2009; 21 (7): 793-801).*
Goldfarb et al. (Anticancer Res. May-Jun. 1998; 18 (3A): 1441-6).*
Geller et al. (Cytotherapy. Jan. 2011; 13 (1): 98-107; pp. 1-19).*
Iovino et al. (Immunotherapy. Jan. 2011; 3 (1): 97-106).*
Maine (J. Clin. Invest. Jul. 2002; 110 (2): 157-9).*
Ames et al. (J. Immunol. Oct. 15, 2015; 195 (8): 4010-9).*
Kimura et al. (Cancer. Jul. 1, 1997; 80 (1): 42-9).*
Haller et al. (Blood. Jun. 11, 2009; 113 (24): 6120-7).*
Yoshida et al. (Cancer Res. Sep. 1, 1998; 48 (17): 5011-6).*
DeBlaker-Hohe et al. (Cell Immunol. Oct. 1, 1995; 165 (1): 33-43).*
Galatiuc et al. (Cell Immunol. Jul. 1995; 163 (2): 167-77).*
Jewett et al. (Cancer Immunol. Immunother. Feb. 2012; 61 (2): 265-74).*
Tseng et al. (Oncotarget. Aug. 21, 2015; 6 (24): 20002-25).*
Bui et al. (Front. Immunol. Dec. 2, 2015; 6: 576; pp. 1-15).*
Kaur et al. (Front. Immunol. Apr. 5, 2017; 8: 297; pp. 1-21).*
Belyaev et al. (Med. Hypotheses. Feb. 2014; 82 (2): 129-33).*
Otten et al. (Science. Mar. 8, 1991; 251 (4998): 1228-31).*
Jewett et al. (J. Cancer. 2013; 4 (1): 12-24).*
Tseng et al. (PLoS One. Jul. 16, 2010; 5 (7): e11590; pp. 1-16).*
Jewett, et al., "Cytokine dependent inverse regulation of CD54 (ICAM1) and major histocompatibility complex class I antigens by nuclear factor kappaB in HEp2 tumor cell line: effect on the funciton of natural killer cells." Hum Immunol (2003), 54(5):505-20.
Jewett, et al., "Emerging mechanisms of immunosuppression in oral cancers." J Dent Res (2006), 85(12):1061-73.
Jewett, et al., "Inhibition of nuclear factor kappa B (NFkappaB) activity in oral tumor cells prevents depletion of NK cells and increases their functional activation." Cancer Immunol Immunother (2006), 55(9):1052-63.
Jewett, et al., "Rapid and potent induction of cell death and loss of NK cell cytotoxicity against oral tumors by F(ab')2 fragment of anti-CD16 antibody." Cancer Immunol Immunother (2008), 57(7):1053-66.
Jewett, et al., "Strategies to rescue mesenchymal stem cells (MSCs) and dental pulp stem cells (DPSCs) from NK cell mediated cytotoxicity." PLoS One 5(3):e9874.
Jewett, et al., "Target-induced inactivation and cell death by apoptosis in a subset of human NK cells." J Immunol (1996), 156(3):907-15.
Morrison, et al., "Chemokine-mediated recruitment of NK cells is a critical host defense mechanism in invasive aspergillosis." J Clin Invest (2003), 112(12):1862-70.

(Continued)

*Primary Examiner* — Stephen Rawlings
(74) *Attorney, Agent, or Firm* — Pamela J. Sherwood; Bozicevic, Field & Francis LLP

(57) ABSTRACT

Compositions and methods are provided for killing of cancer stem cells, and for the transplantation of pluripotent stem cells and differentiated cells derived therefrom.

16 Claims, 42 Drawing Sheets

(56) References Cited

OTHER PUBLICATIONS

Paranjpe, et al., "N-acetylcysteine protects dental pulp stromal cells from HEMA-induced apoptosis by inducing differentiation of the cells." Free Radic Biol Med (2007), 43(10):1394-1408.
Wang, et al., "Regulation of the innate and adaptive immune responses by Stat-3 signaling in tumor cells." Nature Medicine (2004), 10(1):48-54.
Zhang, et al., "A subpopulation of CD133(+) cancer stem-like cells characterized in human oral squamous cell carcinoma confer resistance to chemotherapy." Cancer Letters (2010), 289(2):151-60.
Maasilta et al., (Radiation and Oncology, 1992, v.25, pp. 192-195).

* cited by examiner

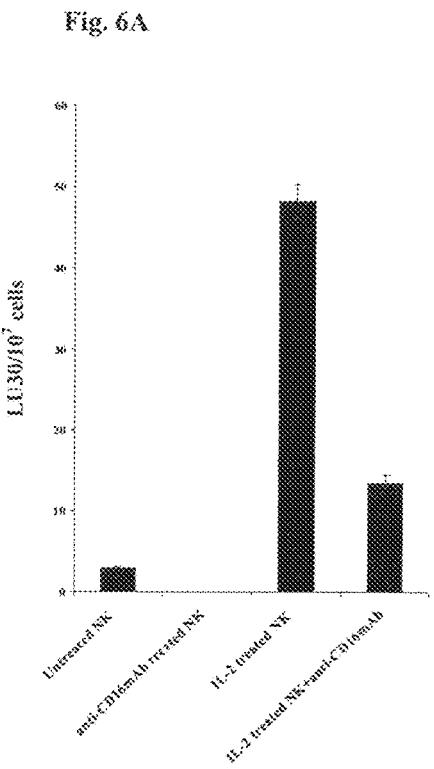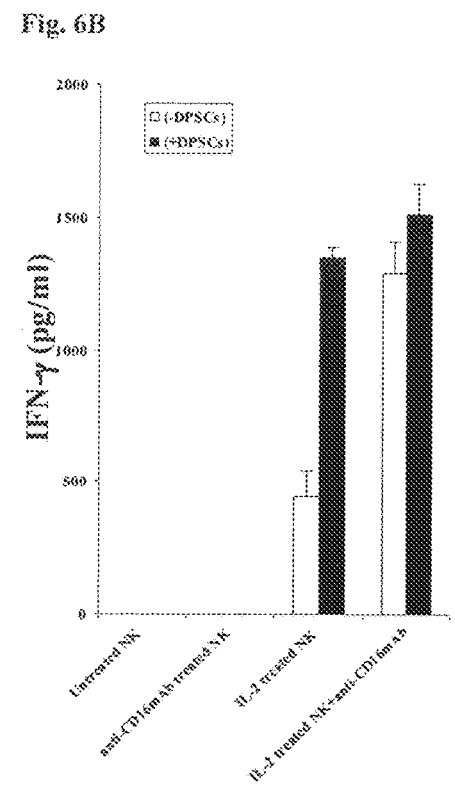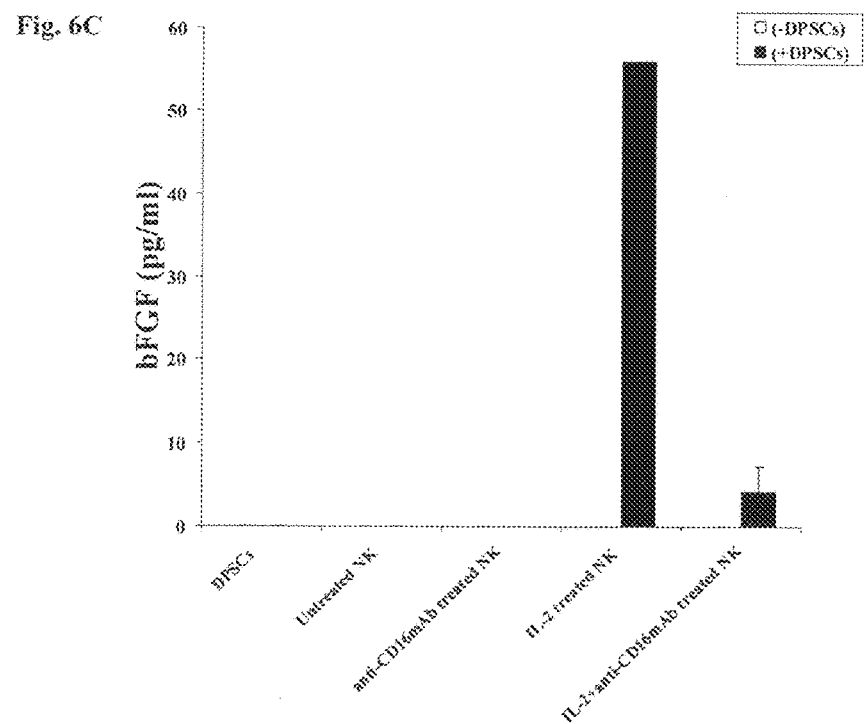

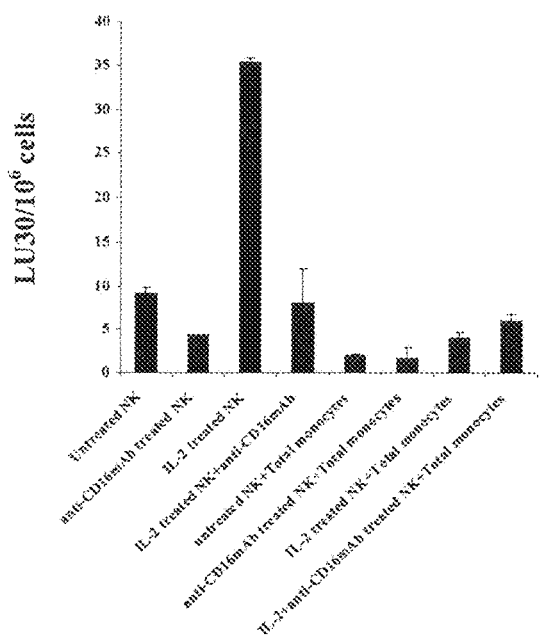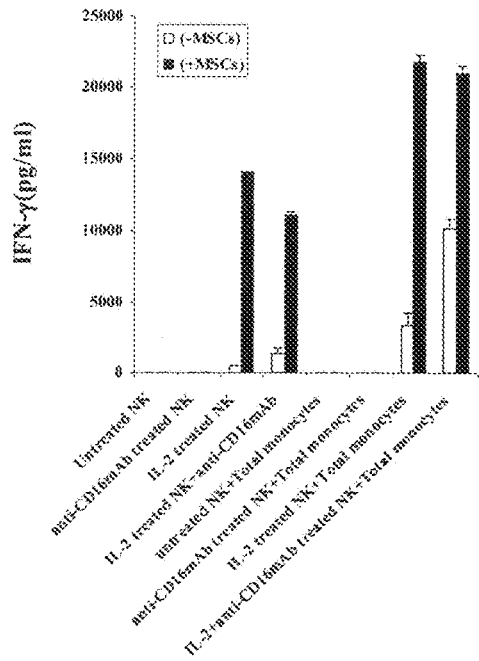

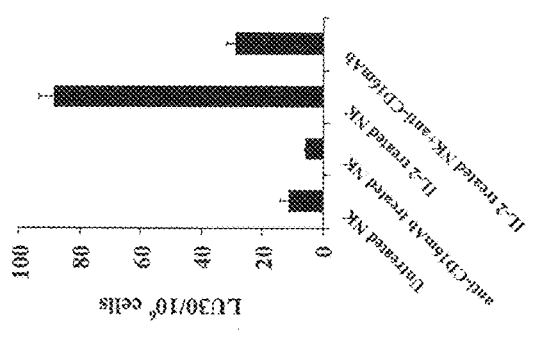
Figures 18A
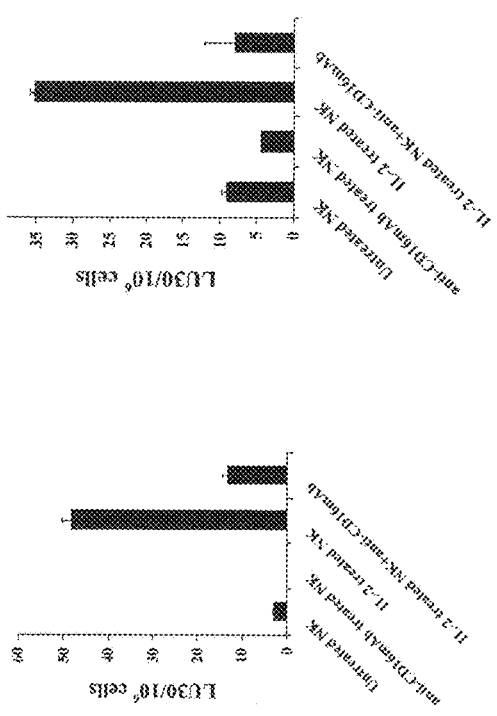
Figures 18B
Figures 18D
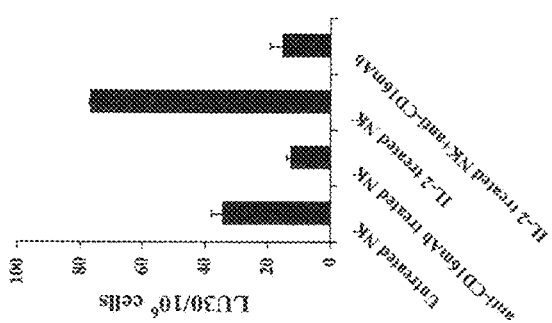
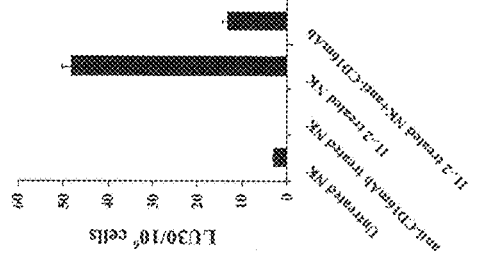
Figures 18C

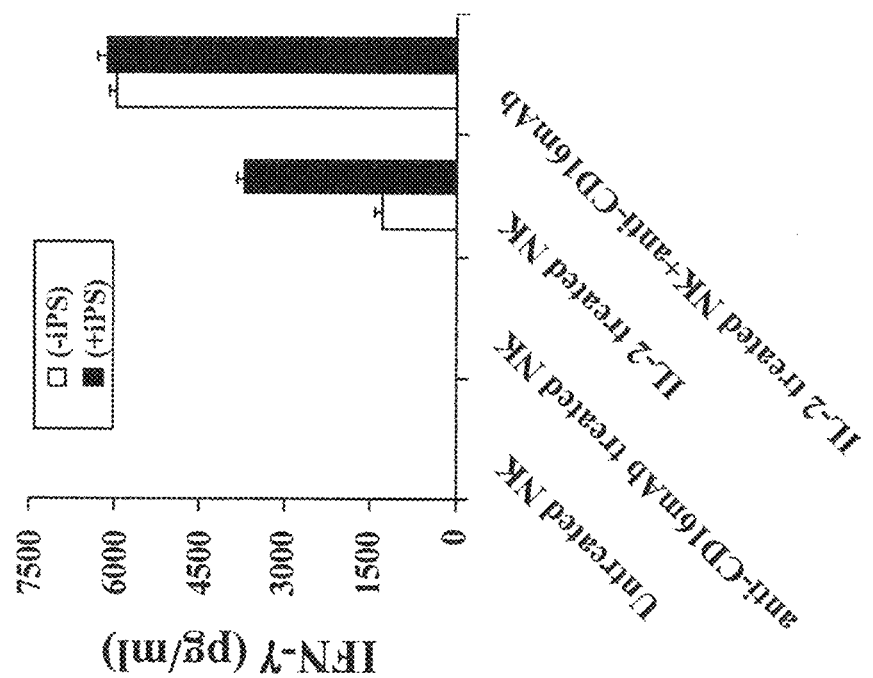
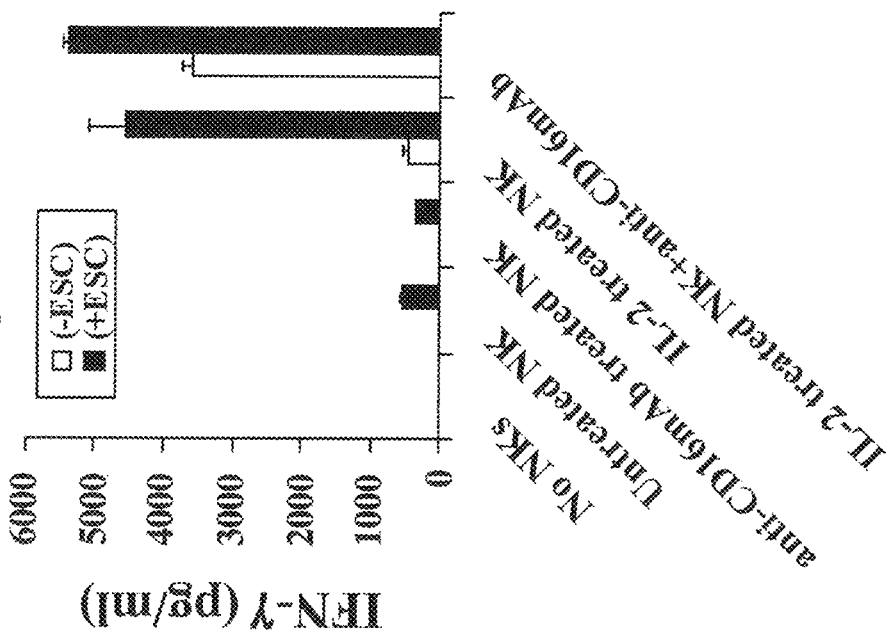

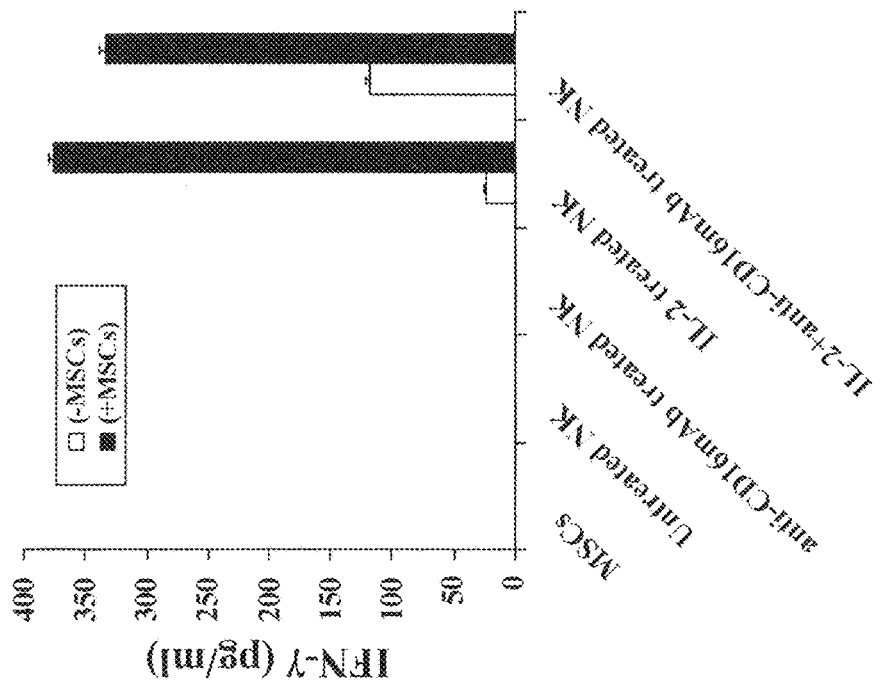
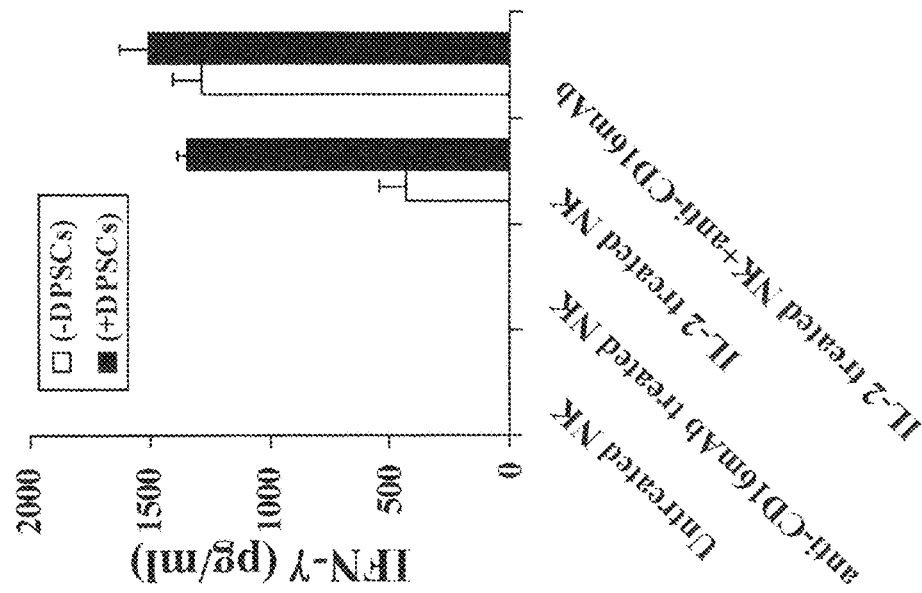
Figures 19C
Figures 19D

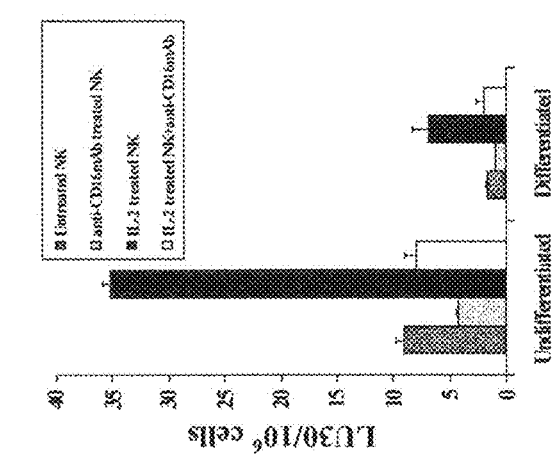
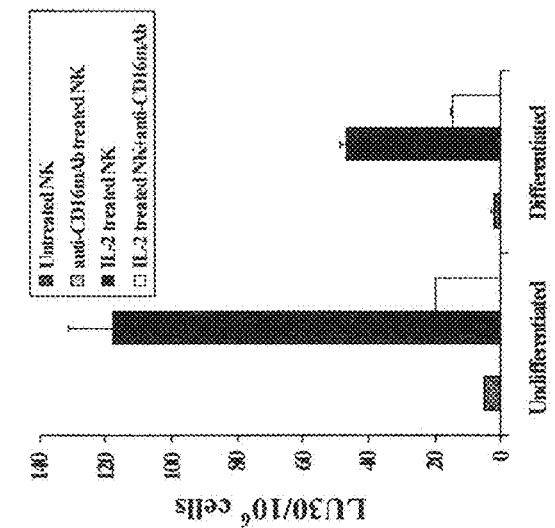
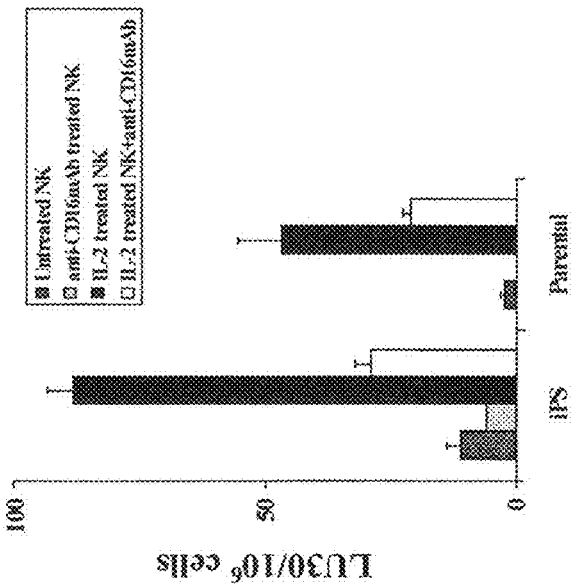
Figures 21A
Figures 21B
Figures 21C

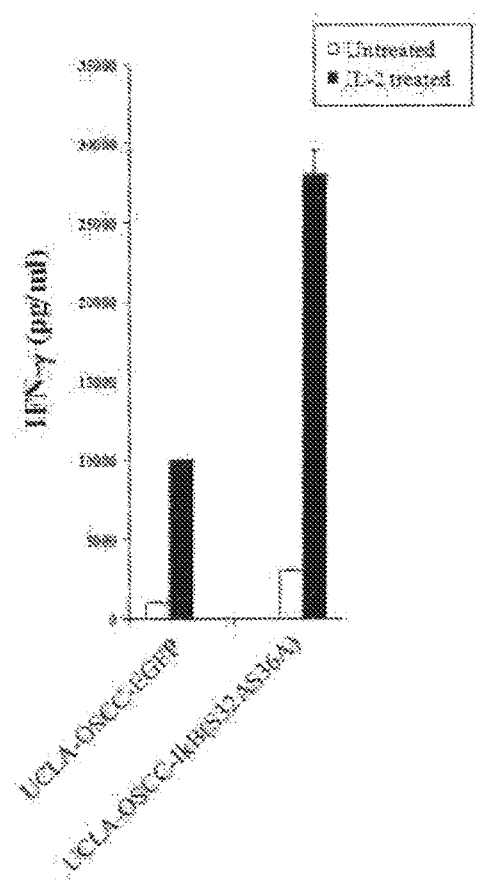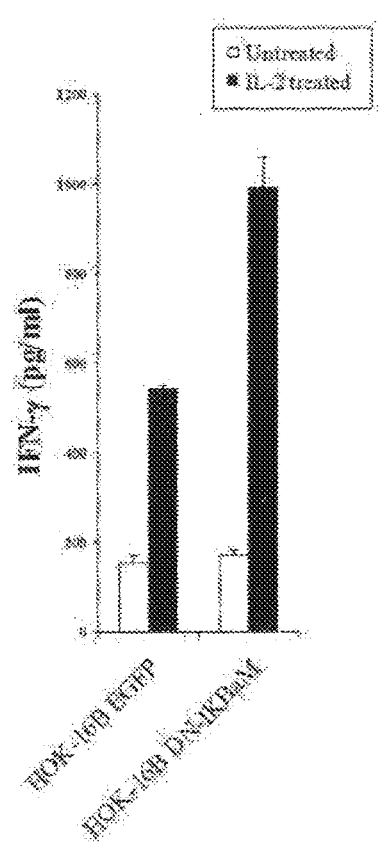
Figures 23E
Figures 23F (day 0)

(day 2)

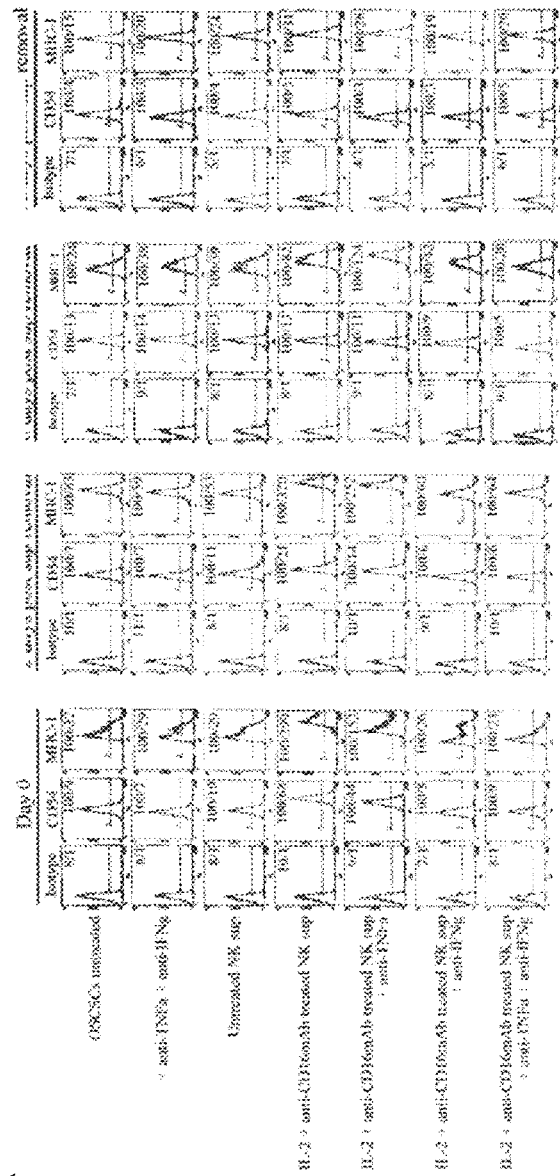
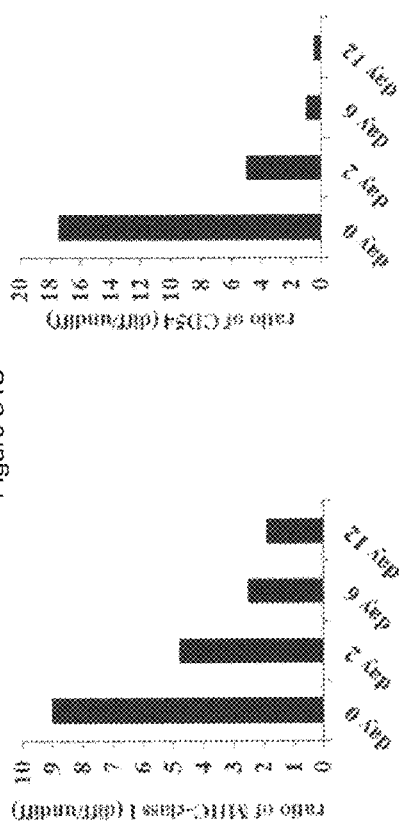
Figure 34A
Figure 34B
Figure 34C

DEPLETION OF CANCER STEM CELLS

FEDERALLY SPONSORED RESEARCH AND DEVELOPMENT

This invention was made with Government support under Grant Number DE012880, awarded by the National Institutes of Health. The Government has certain rights in the invention.

BACKGROUND OF THE INVENTION

Immunosuppression and tumor escape from immune recognition are thought to be major factors responsible for the establishment and progression of cancer. A number of factors responsible for the suppression of NK cell cytotoxicity in humans have been identified previously. However, the significance and the precise mechanism of this suppression induced during the interaction of NK cells with either tumor cells or healthy primary cells are not well understood. It is shown that freshly isolated tumor infiltrating NK cells are not cytotoxic to autologous tumors. Moreover, NK cells obtained from the peripheral blood of patients with cancer have significantly reduced cytotoxic activity. In addition, NK cell cytotoxicity is suppressed after their interaction with stem cells. However, interaction of NK cells with the resistant tumors does not lead to suppression of NK cell cytotoxicity.

Many mechanisms have been proposed for the functional inactivation of tumor associated NK cells including the over-expression of Fas ligand, the loss of mRNA for granzyme B and decreased CD16 and its associated zeta chain.

Many metastatic tumor cells exhibit constitutively elevated NFκB activity. Increased NFκB activity is shown to have a causal relationship to neoplastic transformation, and uncontrolled cell growth in many cell types. Human solid tumors exhibit constitutively activated NFκB.

We have previously shown that NK resistant primary oral keratinocyte tumors demonstrate higher nuclear NFκB activity and secrete significant levels of Granulocyte Monocyte-Colony Stimulating Factor (GM-CSF), Interleukin (IL)-1β, IL-6 and IL-8. Moreover, the addition of Non-steroidal anti-inflammatory drugs (NSAIDs) which inhibit NFκB have the ability to reverse immunosuppression induced by a tobacco-specific carcinogen in addition to their well-established ability to decrease oral dysplasia as well as induction of overt cancer in transgenic animals. In agreement, we have previously demonstrated that inhibition of NFκB by Sulindac treatment of tumor cells increases functional activity of NK cells. In addition, targeted inhibition of NFκB in skin epithelial cells resulted in the induction of auto-immunity and inflammation.

The exact mechanism by which NFκB nuclear function in oral keratinocytes modulate and shape the function of key interacting immune effectors is yet to be determined. We have previously shown that inhibition of NFκB by the IκB super-repressor in HEp2 tumors leads to significant increase in cytotoxicity and secretion of IFN-γ by the human NK cells. However, neither the underlying significance nor the physiological relevance of NFκB modulation in tumors or in primary cells responsible for the alteration of NK cell cytotoxic function have been addressed or studied previously. It is clear that the objective in cancer is to enhance the function of cytotoxic immune effectors and in auto-immunity and inflammation the aim is to inhibit immune effector function. Therefore, dissection of the underlying mechanisms of immune activation when NFκB is modulated in the cells might help design strategies to target each disease accordingly. Indeed, targeted inhibition of NFκB function in both the intestinal epithelial cells and the myeloid cells was previously shown to result in a significant decrease in the size and the numbers of the tumor cells.

Regenerative medicine is the process of creating living, functional tissues to repair or replace tissue or organ function lost due to age, disease, damage, or congenital defects. This field holds the promise of regenerating damaged tissues and organs in the body by introducing outside cells, tissue, or even whole organs to integrate and become a part of tissues or replace whole organ. Importantly, regenerative medicine has the potential to solve the problem of the shortage of organs available for donation compared to the number of patients that require life-saving organ transplantation.

One key to the success of regenerative medicine strategies has been the ability to isolate and generate stem cells, including pluripotent stem cells. In one aspect, pluripotent stem cells can be differentiated into a necessary cell type, where the mature cells are used to replace tissue that is damaged by disease or injury. This type of treatment could be used to replace neurons damaged by spinal cord injury, stroke, Alzheimer's disease, Parkinson's disease, or other neurological problems. Cells grown to produce insulin could treat people with diabetes and heart muscle cells could repair damage after a heart attack. This list could conceivably include any tissue that is injured or diseased.

The generation of pluripotent stem cells that are genetically identical to an individual provides unique opportunities for basic research and for potential immunologically-compatible novel cell-based therapies. Methods to reprogram primate somatic cells to a pluripotent state include differentiated somatic cell nuclear transfer, differentiated somatic cell fusion with pluripotent stem cells, and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

A significant first hurdle in stem cell-based therapy is the differentiation of pluripotent cells into a desired tissue type. Such methods currently rely on the step-wise introduction of factors and conditions to guide the cells down a developmental pathway, resulting eventually in a mature or committed progenitor cell that can transplanted into a patient.

Embryonic stem cells (ESCs) are an attractive source for tissue regeneration and repair therapies because they can be cultured indefinitely in vitro and can be differentiated into virtually any cell type in the adult body. However, for this approach to succeed, the transplanted ESCs must engraft successfully and survive long enough to permit a therapeutic benefit. An important obstacle facing the engraftment and function of hESCs is transplant rejection by the immune system. The present invention addresses this issue.

SUMMARY OF THE INVENTION

Compositions and methods are provided for treatment of cancer, particularly the killing of cancer stem cells, by administration of natural killer cells for the purpose of killing cancer cells, and by differentiation of the stem cells. In some embodiments the cancer stem cells are carcinoma stem cells, including without limitation squamous carcinoma stem cells. In other embodiments the cancer stem cells are adenocarcinoma cells, including without limitation pancreatic adenocarcinoma cancer stem cells. In some embodiments the cancer stem cells are oral squamous carcinoma stem cells.

Cancers are optionally profiled prior to treatment to determine the presence of cancer stem cells, where such cells may be identified by the presence of markers known in the art, including without limitation expression of CD44, CD133, etc., where the presence of the cancer stem cells, e.g. at 0.1%, 1%, 2%, 5% or more of the tumor mass is indicative that the individual is suited for treatment by the methods of the invention.

The present invention demonstrates a dual aspect of NK cell biology, termed split anergy. In a microenvironment, significant infiltration of immune effectors can anergize NK cells to lose cytotoxicity and gain the ability to secrete cytokines. NK cells are likely to encounter and interact with other immune effectors such as monocytes/macrophages, other myeloid-derived suppressor cells (MDSCs) or with cancer-associated fibroblasts. These NK cells then support differentiation of stem cells. NK cell-differentiated epithelial cells will no longer be killed or induce cytokine secretion by the NK cells, resulting in the resolution of inflammation.

Two distinct strategies can be applied with respect to NK cells and eliminating tumors: one which targets cancer stem cells and the other which targets differentiated cancer cells. Cancer stem cells are more resistant to chemotherapeutic drugs but sensitive to NK cell mediated killing, while differentiated cancer cells are more resistant to NK cell mediated killing but relatively more sensitive to chemotherapeutic drugs. A combination therapy can provide for the elimination of both undifferentiated and differentiated tumors. These patients may benefit from repeated allogeneic NK cell transplantation for elimination of cancer stem cells. NK cells also have the benefit of differentiating cancer stem cells, thereby increasing the sensitivity to chemotherapy.

In some embodiments, a sequential procedure is used to treat cancer. As endogenous NK cells can be anergic, allogeneic cells can be used. An effective dose of activated NK cells are brought into contact with the tumor cell population, which has the effect of killing cancer stem cells and differentiating cancer stem cells. For example, an effective dose of NK cells treated with IL-2, anti-CD16 and autologous monocytes or osteoclasts, can be administered for treatment of cancer. The NK cells can be additionally treated with sonicated probiotic bacteria to increase cytokine expression. As a final step the cancer can be treated with a chemotherapeutic agent to eliminate the differentiated tumor cells, e.g. with paclitaxel and NAC. In some embodiments, NK cells are activated by culture in the presence of NK cells are enriched from peripheral blood and activated by culture in the presence of IL-2, anti-CD16 antibodies, sonicated probiotic bacteria, and osteoclasts.

The methods of the invention involve an initial depletion of effector cells in the tumor microenvironment, for example by irradiation, chemotherapy, and the like, in a dose that is sufficient to substantially deplete monocytes present in the tumor microenvironment. NK cells are then delivered to the tumor site, e.g. by localized injection at the site of cancer or in close proximity to the site of cancer, although systemic administration may find use, e.g. when the cancer is metastatic. In some embodiments the NK cells are autologous. In other embodiments the NK cells are allogeneic. Repeated administration of NK cells to lyse cancer stem cells may be required. The administered NK cells initially kill cancer stem cells, and can then differentiate the cancer stem cells to a population that is sensitive to chemotherapy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A). UCLA-OSCCs or UCLA-OSCSCs were left untreated or treated with EGF (10 ng/ml), and the cell extracts were prepared after an overnight incubation, and run on polyacrylamide gel, after which the bands were transferred and blotted with an antibody specific for phospho-Stat3 (FIG. 1B). UCLA-OSCCs or UCLA-OSCSCs at a density of $2\times10^5$ cells per well were transduced with the NFκB-Luciferase lentiviral reporter vector for 48 hours before they were lysed and luciferase activity measured [RLU/s] using a luminometer. An internal lentiviral vector expressing constitutive Luciferase was used for normalization (FIG. 1C). One of three representative experiments is shown in this figure.

FIGS. 6A-6C Lysis of DPSCs by untreated and IL-2 treated NK cells is inhibited by anti-CD16 antibody treatment, however, the same treatment induced significant secretion of IFN-γ by the NK cells. NK cells (1×10$^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled DPSCs and NK cell cytotoxicity was determined using a standard 4 hour $^{51}$Cr release assay, and the lytic units 30/10$^6$ were determined using inverse number of NK cells required to lyse 30% of the DPSCs×100 (FIG. 6A). NK cells were treated as described in FIG. 6A and each NK sample at (1×10$^5$/ml) either cultured in the absence of DPSCs or added to DPSCs at an NK to DPSC ratio of 1:1. After an overnight culture, supernatants were removed from the cultures and the levels of IFN-γ (FIG. 6B), and bFGF (FIG. 6C) secretion were determined using specific ELISAs. One of five representative experiments is shown in this figure.

FIGS. 7A-7E Lysis of MSCs by untreated and IL-2 treated NK cells is inhibited by anti-CD16 antibody treatment, however, the same treatment induced significant secretion of IFN-γ by the NK cells. NK cells (1×10$^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled MSCs and NK cell cytotoxicity was determined using a standard 4 hour $^{51}$Cr release assay, and the lytic units 30/10$^6$ were determined using inverse number of NK cells required to lyse 30% of the MSCs×100 (FIG. 7A). NK cells were treated as described in FIG. 7A and each NK sample at (1×10$^5$/ml) either cultured in the absence of MSCs or added to MSCs at an NK to MSC ratio of 1:1. After an overnight culture, supernatants were removed from the cultures and the levels of IFN-γ (FIG. 7B), and bFGF (FIG. 7C) secretion were determined using specific ELISAs. One of five representative experiments is shown in this figure. Monocytes were purified from PBMCs and irradiated as indicated in the Material and Methods section. MSCs (1×10$^6$ cells/plate) were cultured with the irradiated monocytes (monocyte:MSC ratio of 1:1) for 24-48 hours before they were removed from the plates, washed and labeled with $^{51}$Cr and used as targets in the cytotoxicity assays against NK cells. The NK samples were either left untreated or treated with anti-CD16 mAb (3 µg/ml), IL-2 (1000 u/ml), or a combination of IL-2 (1000 u/ml) and anti-CD16 mAb (3 µg/ml) for 24-48 hours before they were added to $^{51}$Cr labeled MSCs at different effector to target (E:T) ratios. Supernatants were removed after 4 hours of incubation and the released radioactivity counted by a γ counter. % cytotoxicity was determined at different E:T ratio, and LU$_{30}$/10$^6$ cells were calculated using the inverse of the number of effectors needed to lyse 30% of the MSCs×100. One of three representative experiments is shown in this figure (FIG. 7D). MSCs (1×10$^5$ cells/well) were co-cultured with and without irradiated Monocytes at 1:1 MSCs to monocytes for 24-48 hours before untreated or IL-2 (1000 u/ml) pre-treated or anti-CD16mAb (3 µg/ml) pre-treated, or a combination of IL-2 (1000 u/ml) and anti-CD16 mAb (3 µg/ml) pre-treated NK cells at 1:1:1 NK:monocyte:MSC ratios were added. NK cells were pre-treated as indicated for 24-48 hours before they were added to the co-cultures of monocytes and MSCs. NK samples were also cultured in the absence of monocytes and MSCs. After 24-48 hours of the addition of NK cells the supernatants were removed from the cultures and the levels IFN-γ (FIG. 7E) were determined using ELISA. One of five representative experiments is shown in this figure.

FIGS. 18A-18D. Lysis of stem cells by NK cells.

FIGS. 19A-19D. Stem cells triggered significant secretion of IFN-γ from IL-2 treated NK cells when compared to IL-2 treated NK cells in the absence of stem cells.

FIGS. 21A-21C. Differentiated DPSCs are more resistant to NK cell mediated cytotoxicity.

FIGS. 23A-23F. Blocking NFκB in UCLA-OSCCs and HOK-16B oral epithelial cells lowered IL-6 to IFN-γ ratios and increased their sensitivity to NK cell mediated cytotoxicity.

FIGS. 34A-34C Increased expression of CD54 and MHC class I on OSCSCs differentiated with supernatants from IL-2 and anti-CD16mAb treated NK cells. OSCSCs were treated with NK supernatants in the presence and absence of anti-TNF-α and anti-IFN-γ antibodies as described in FIG. 1A and the surface expression of CD54 and MHC Class 1 on untreated and NK supernatant treated OSCSCs were assessed after 4 days of differentiation. After differentiation, OSCSCs were washed and cultured in normal culture medium without the addition of NK supernatants for a period of 2 days, 6 days and 12 days (FIG. 34A). Surface expression of CD54 and MHC Class I at each time point was assessed after PE conjugated antibody staining followed by flow cytometric analysis. Isotype control antibodies were used as controls. The numbers on the right hand corner are the percentages and the mean channel fluorescence intensities in each histogram. The ratios of MHC class I (FIG. 34B) or CD54 (FIG. 34C) at days 0, 2, 6 and 12 were determined by using the mean channel fluorescence of the IL-2+anti-CD16mAb treated NK supernatant differentiated OSCSCs to the mean channel fluorescence of the untreated OSCSCs.

Figure 1A:
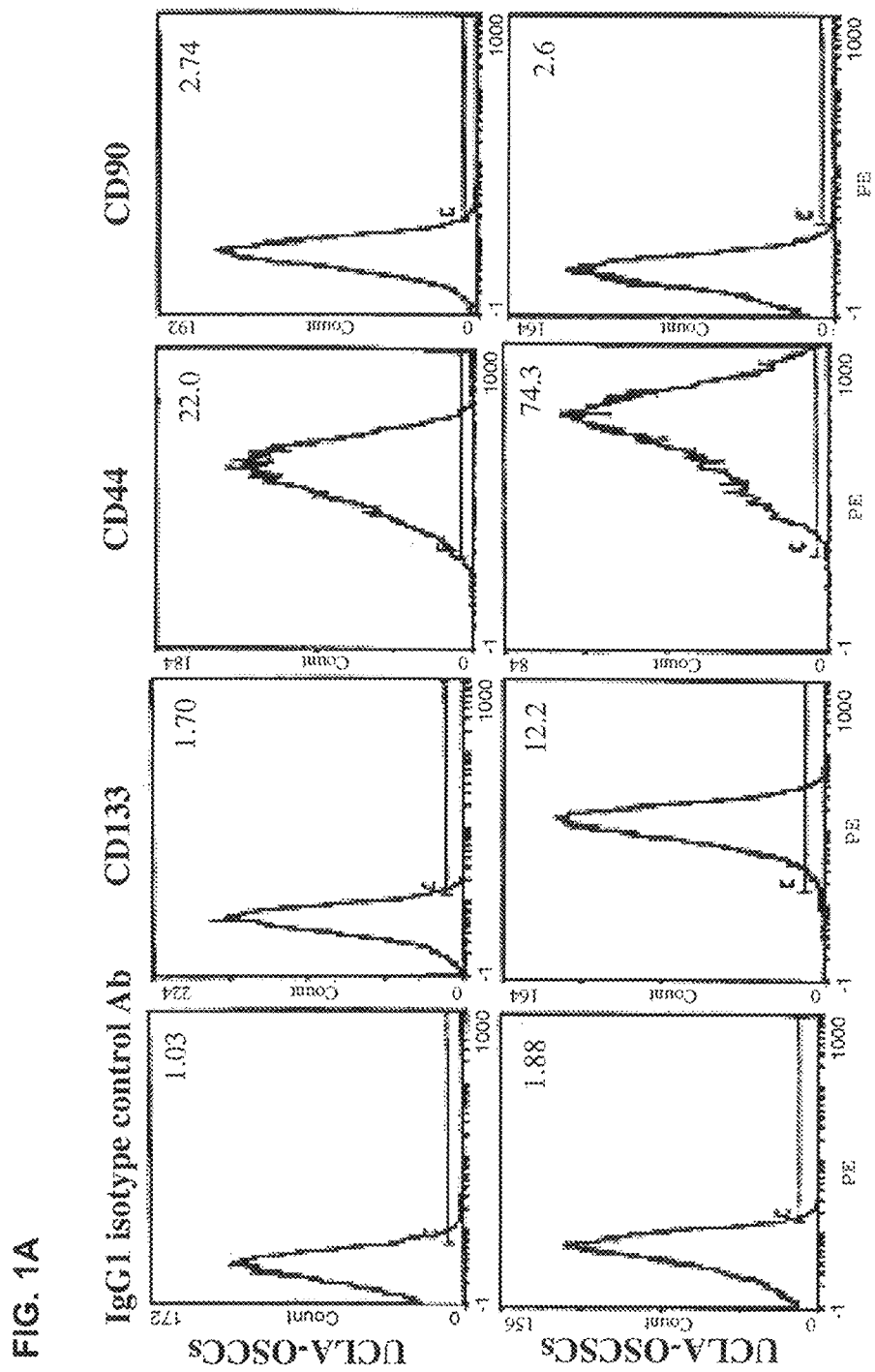
FIGS. 1A-1C. Phenotypic characteristics of UCLA-OSCCs and UCLA-OSCSCs. UCLA-OSCCs or UCLA-OSCSCs were detached, washed and stained with the antibodies recognizing surface receptors indicated in the figure and analyzed by flow cytometry. Isotype control antibodies were used as controls. The numbers on the right hand corner are the mean channel fluorescence intensity.
Figure 1A:
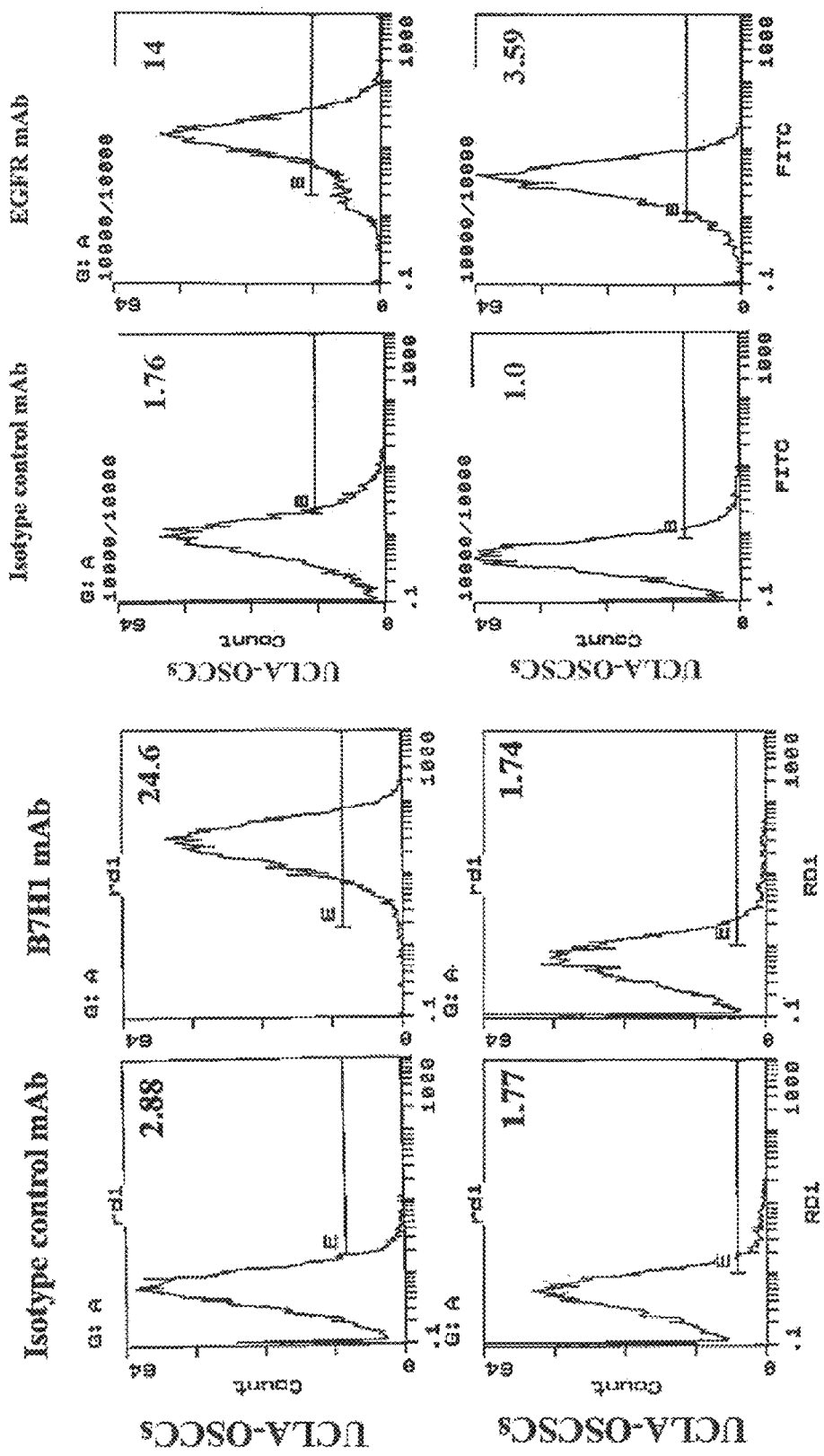

Significant infiltration of immune effectors can anergize NK cells to lose cytotoxicity and gain the ability to secrete cytokines, a term which we previously coined 'split anergy' in NK cells, and to support differentiation of stem cells. NK cells are likely to encounter and interact with other immune effectors such as monocytes/macrophages, other myeloid-derived suppressor cells (MDSCs) or with cancer-associated fibroblasts, in order to be conditioned to form anergized/regulatory NK (NKreg) cells. NK cells may also directly interact with stem cells at the base of the epithelial layer, in which case by eliminating their bound stem cells, they can become conditioned to support differentiation of other stem cells. NK cell-differentiated epithelial cells will no longer be killed or induce.

DETAILED DESCRIPTION OF THE INVENTION

Compositions and methods are provided for the treatment of cancer with NK cells. The methods of the invention involve an initial depletion of effector cells in the tumor microenvironment, for example by irradiation, chemotherapy, and the like, in a dose that is sufficient to substantially deplete monocytes present in the tumor microenvironment. NK cells are then delivered to the tumor site. In some embodiments the NK cells are autologous. In other embodiments the NK cells are allogeneic. Repeated administration of NK cells to lyse cancer stem cells may be required. The NK cells are typically activated by culturing in the presence of IL-2 and monocytes or osteoclasts, which culture conditions may further include sonicated probiotic bacteria; and/or anti-IL-16. In some embodiments the NK cells are activated by culture with osteoclasts, IL-2, anti-CD16 and sonicated probiotic bacteria. The NK cells may be cultures for about 6 hours, about 12 hours, about 18 hours, about 24 hours, about 36 hours about 48 hours, or about 2 days, about 3 days, about 4 days or more. The ratio of NK cells to monocytes and/or osteoclasts may be about 100:1, 50:1, 10:1, 5:1, 3:1, 2:1, 1:1, 1:2, 1:3, 1:5, 1:10, 1:50, 1:100. Monocytes or osteoclasts may be allogeneic, autologous, a primary or established cell line, etc.

The methods of the invention may be combined with therapy designed to differentiate stem cells, and to then eliminate the differentiated cancer cells present in a tumor, e.g. in a combination therapy with EGFR antibody (Erbitux), a therapeutic dose of a taxane and N-acetylcysteine. The methods of the invention may also be enhanced by blocking or targeted knock-down of COX2 and/or NFκB in the tumor.

As used herein, a recipient is an individual to whom tissue or cells from another individual (donor), commonly of the same species, has been transferred. Generally the MHC antigens, which may be Class I or Class II, will be matched, although one or more of the MHC antigens may be different in the donor as compared to the recipient. The recipient and donor are generally mammals, preferably human. Laboratory animals, such as rodents, e.g. mice, rats, etc. are of interest for drug screening, elucidation of developmental pathways, etc. For the purposes of the invention, the cells may be allogeneic, autologous, or xenogeneic with respect to the recipient.

Anti CD16 antibody can be used to tolerize NK cells to support differentiation of stem cells. Anti-CD16 antibody will block cytotoxicity of the NK cells but will induce secretion of IFN-γ which will induce differentiation and resistance of stem cells, thus NK cells will be treated with IL-2 and/or IL-12, or IFN-α in the presence of anti-CD16 antibody to induce split anergy which will then support differentiation of stem cells. The cells can be further combined with autologous monocytes or osteoclasts; and/or sonicated probiotic bacteria.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

Cancer stem cells. It is well documented that many types of tumors contain cancer cells with heterogeneous phenotypes, reflecting aspects of the differentiation that normally occurs in the tissues from which the tumors arise. The variable expression of normal differentiation markers by cancer cells in a tumor suggests that some of the heterogeneity in tumors arises as a result of the anomalous differentiation of tumor cells. It has been shown for solid cancers that the cells are phenotypically heterogeneous and that only a small proportion of cells are clonogenic in culture and in vivo. Tumorigenic and non-tumorigenic populations of cancer cells can be isolated based on their expression of cell surface markers. In many cases of breast cancer, only a small subpopulation of cells had the ability to form new tumors.

The presence of cancer stem cells has profound implications for cancer therapy. For many years, however, it has been recognized that small numbers of disseminated cancer cells can be detected at sites distant from primary tumors in patients that never manifest metastatic disease. Most cancer cells lack the ability to form a new tumor such, that only the dissemination of rare cancer stem cells can lead to metastatic disease. If so, the goal of therapy must be to identify and kill this cancer stem cell population. Squamous carcinoma stem cells (SCSC) are known in the art to be positive for expression of CD44 and CD133, and negative for expression of specific lineage markers.

Samples, including tissue sections, slides, etc. containing a squamous carcinoma tissue, are optionally stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the carcinoma.

The invention finds use in the treatment of squamous cell carcinomas. Carcinomas are malignancies that originate in the epithelial tissues. Epithelial cells cover the external surface of the body, line the internal cavities, and form the lining of glandular tissues. In adults, carcinomas are the most common forms of cancer.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

Squamous cells are flat cells which form the surface of an epithelium. They can be identified histologically by the fact that they look flattened and thin under a microscope. Epithelia lined by squamous cells can be classified as either simple squamous epithelium or stratified squamous epithelium.

Squamous cell carcinoma is a carcinoma that may occur in many different organs, including the skin, mouth, esophagus, lungs, and cervix. It is a malignant tumor of epithelium that shows squamous cell differentiation. Squamous cell carcinoma is usually developed in the epithelial layer of the skin and sometimes in various mucous membranes of the body. This type of cancer can be seen on the skin, lips, inside the mouth, throat or esophagus.

The most common noncutaneous tumor of the head and neck is squamous cell carcinoma of the larynx, followed by squamous cell carcinomas of the palatine tonsil, tongue, and floor of the mouth. Somewhat less common are tumors of the salivary gland, jaw, nose and paranasal sinuses, and ear. Tumors of the thyroid gland, eye, and skin are discussed elsewhere in the manual. Excluding the skin and thyroid gland, >90% of head and neck cancers are squamous cell (epidermoid) carcinomas, and 5% are melanomas, lymphomas, and sarcomas. The Epstein-Barr virus plays a role in the pathogenesis of nasopharyngeal cancer.

Oral squamous cell carcinoma affects about 30,000 Americans each year. Oral squamous cell carcinoma is the most common oral or pharyngeal cancer. The chief risk factors for oral squamous cell carcinoma are smoking and alcohol use. Squamous cell carcinoma of the tongue may also result from Plummer-Vinson syndrome, syphilis, or chronic trauma. About 40% of intraoral squamous cell carcinomas begin on the floor of the mouth or on the lateral and ventral surfaces of the tongue. About 38% of all oral squamous cell carcinomas occur on the lower lip, and about 11% begin in the palate and tonsillar area.

If carcinoma of the tongue is localized (no lymph node involvement), 5-yr survival is about 50%. For localized carcinoma of the floor of the mouth, 5-yr survival is 65%. With lymph node metastasis, the 5-yr survival is 20%. For lower lip lesions, 5-yr survival is 90%, and metastases are rare. Carcinoma of the upper lip tends to be more aggressive and metastatic. For carcinoma of the palate and tonsillar area, 5-yr survival is 68% if patients are treated before lymph node involvement but only 17% after involvement. Metastases reach the regional lymph nodes first and later the lungs. Surgery and radiation therapy are the treatments of choice.

About 90% of vulvar cancers are squamous cell carcinomas. Vulvar cancer most often occurs in elderly women. It usually manifests as a palpable lesion. Diagnosis is by biopsy. Treatment includes excision and inguinal and femoral lymph node dissection. Vulvar cancer accounts for about 3 to 4% of gynecologic cancers in the US. Average age at diagnosis is about 70, and incidence increases with age. Risk factors include vulvar intraepithelial neoplasia (VIN), human papillomavirus infection, heavy cigarette smoking, lichen sclerosus, squamous hyperplasia, squamous carcinoma of vagina or cervix, and chronic granulomatous diseases. VIN is a precursor to vulvar cancer. VIN may be multifocal. Sometimes adenocarcinoma of the vulva, breast, or Bartholin's glands also develops.

Squamous cell carcinoma of the skin is a malignant tumor of epidermal keratinocytes that invades the dermis, usually occurring in sun-exposed areas. The incidence in the US is 80,000 to 100,000 cases annually, with 2000 deaths. Local destruction may be extensive, and metastases occur in advanced stages. Diagnosis is by biopsy. Treatment depends on the tumor's characteristics and may involve curettage and electrodesiccation, surgical excision, cryosurgery, or, occasionally, radiation therapy.

Squamous cell carcinoma is the most common malignancy of the larynx. In the US, it is 4 times more common in men and is more common among blacks than whites. Over 95% of patients are smokers; 15 pack-years of smoking increases the risk 30-fold. Sixty percent of patients present with localized disease alone, 25% with local disease and regional nodal metastatic disease, and 15% with advanced disease, distant metastases, or both. Common sites of origin are the true vocal cords (glottis) particularly the anterior portion, supraglottic larynx (epiglottis), hypopharynx (pyriform sinus), and postcricoid area.

The most common malignant esophageal tumor is squamous cell carcinoma. Symptoms are progressive dysphagia and weight loss. Diagnosis is by endoscopy, followed by CT and endoscopic ultrasound for staging. Treatment varies with stage and generally includes surgery with or without chemotherapy and radiation. Long-term survival is poor except for those with local disease. About 8000 cases of esophageal squamous cell carcinoma occur annually in the US.

About 80 to 85% of all cervical cancers are squamous cell carcinoma. Diagnosis is by screening cervical Papanicolaou (Pap) test and biopsy. Staging is clinical. Treatment usually includes surgical resection, radiation therapy, and, unless cancer is localized, chemotherapy; if cancer is widely metastasized, treatment is primarily chemotherapy. Cervical cancer results from cervical intraepithelial neoplasia (CIN), which appears to be caused by infection with human papillomavirus (HPV) type 16, 18, 31, 33, 35, or 39.

CIN is graded as 1 (mild cervical dysplasia), 2 (moderate dysplasia), or 3 (severe dysplasia and carcinoma in situ). CIN 3 is unlikely to regress spontaneously; if untreated, it may, over months or years, penetrate the basement membrane, becoming invasive carcinoma. Invasive cervical cancer usually spreads by direct extension into surrounding tissues or via the lymphatics to the pelvic and para-aortic lymph nodes. Hematogenous spread is possible.

Another common carcinoma is adenocarcinoma. Pancreatic cancer is one example, where pancreatic adenocarcinoma accounts for 85% of pancreatic cancers. These adenocarcinomas start within the part of the pancreas which make digestive enzymes. Several other types of cancer, which collectively represent the majority of the non-adenocarcinomas, can also arise from these cells. Signs and symptoms of the most common form of pancreatic cancer may include yellow skin, abdominal or back pain, unexplained weight loss, light-colored stools, dark urine and loss of appetite. There are usually no symptoms in the disease's early stages, and symptoms that are specific enough to suspect pancreatic cancer typically do not develop until the disease has reached an advanced stage. By the time of diagnosis, pancreatic cancer has often spread to other parts of the body.

Natural killer cells (or NK cells) are a type of cytotoxic lymphocyte that constitute a major component of the innate immune system. NK cells play a major role in the rejection of tumors and cells infected by viruses. They usually express the surface markers CD16 (FcγRIII) and CD56 in humans. Given their strong cytolytic activity and the potential for auto-reactivity, NK cell activity is tightly regulated. NK cells must receive an activating signal, which can come in a variety of forms. NK cells are activated in response to interferons or macrophage-derived cytokines. Cytokines involved in NK activation include IL-12, IL-15, IL-18, IL-2, and CCL5.

NK cells may be isolated by negative or positive selection using methods and reagents known in the art. For example negative selection may utilize commercially available antibodies that bind to CD3, CD4, CD19, CD66b, glycophorin, etc. Alternatively NK cells may be positively selected for expression of CD56, and/or CD16.

Taxanes are a class of chemotherapeutic agent, which include, without limitation, the following compounds:

| Common Name | Trade Name | Structure |
|---|---|---|
| paclitaxel | TAXOL® | 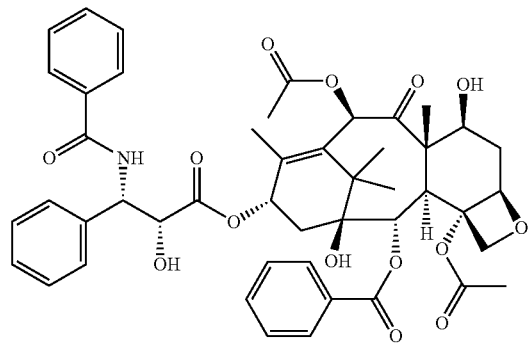 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O] |

-continued

| Common Name | Trade Name | Structure |
|---|---|---|
| docetaxel | TAXO-TERE® | 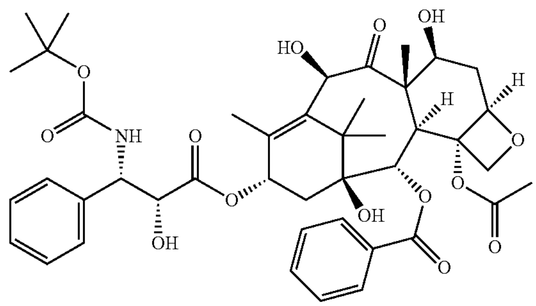 |
| MAC 32 TL 139 | MILA-TAXEL® | 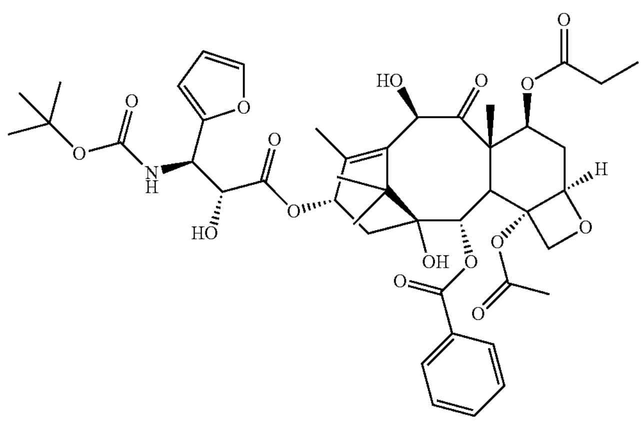 [SMILES: CCC(=O)O[C@H]1C[C@H]2OC[C@@]2(OC(C)=O)C2[C@H](OC(=O)c3ccccc3)[C@]3(O)C[C@H](OC(=O)[C@H](O)[C@@H](NC(=O)OC(C)(C)C)c4ccco4)C(C)=C([C@@H](O)C(=O)[C@@]21C)C3(C)CC] |
| TL-909; MST-997 | SIMO-TAXEL® | 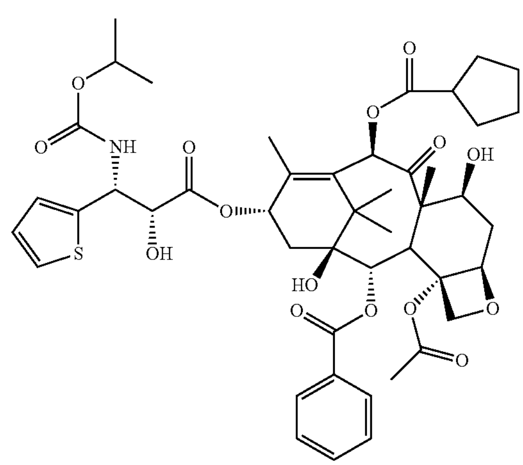 [SMILES: CC(=O)O[C@@]12CO[C@@H]1C[C@H](O)[C@@]1(C)C(=O)[C@H](OC(=O)C3CCCC3)C3=C(C)[C@@H](OC(=O)[C@H](O)[C@@H](NC(=O)OC(C)C)c4cccs4)C[C@@](O)([C@@H](OC(=O)c4ccccc4)C12)C3(C)C] |

-continued
| Common Name | Trade Name | Structure |
|---|---|---|
| TL-310 | | 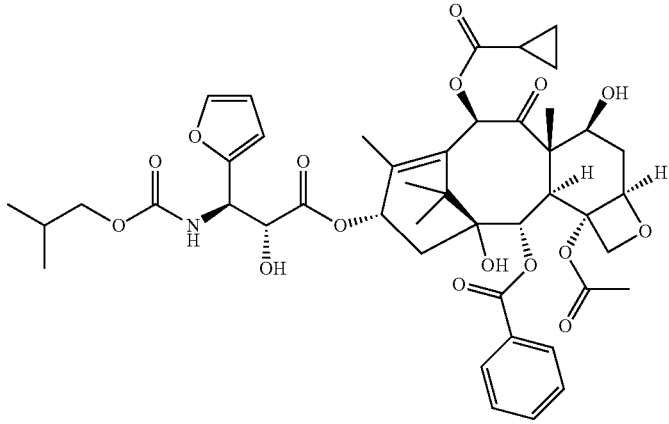 |
| BMS-184476 | | 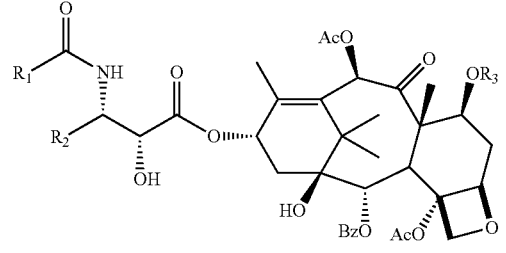 |
| BMS-275183 | | 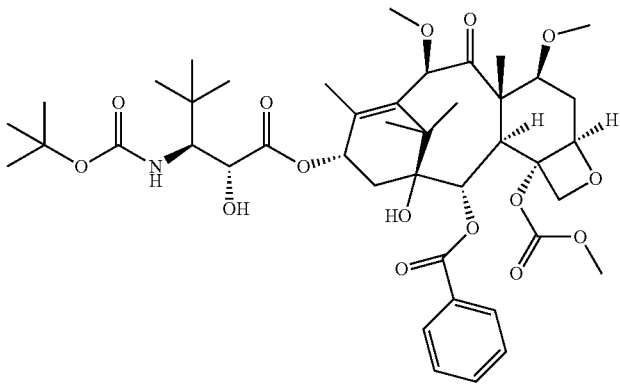 |
| DJ-927 | TESE-TAXEL® | 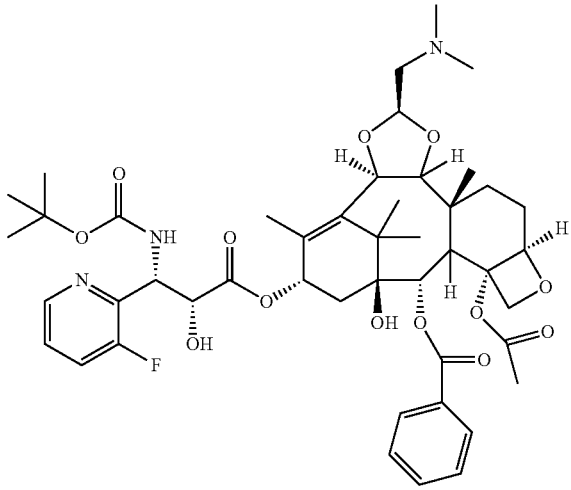 [SMILES: CC(=O)O[C@@]12CO[C@@H]1CC[C@@]1(C)C3O[C@H](CN(C)C)O[C@@H]3C3=C(C)[C@@H](OC(=O)[C@H](O)[C@@H](NC(=O)OC(C)(C)C)c4ncccc4F)C[C@@](O)([C@@H](OC(=O)c4ccccc4)C12)C3(C)C] |

-continued
| Common Name | Trade Name | Structure |
|---|---|---|
| RPR 109881; RPR 109881A | LAROTAXEL® | 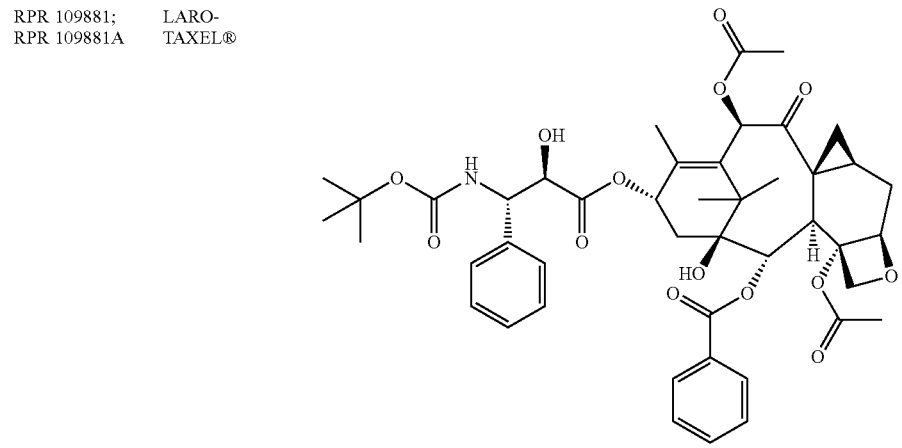 |
| Bay-59-8862, IDN-5109, SB-T-101131 | ORTATAXEL® | 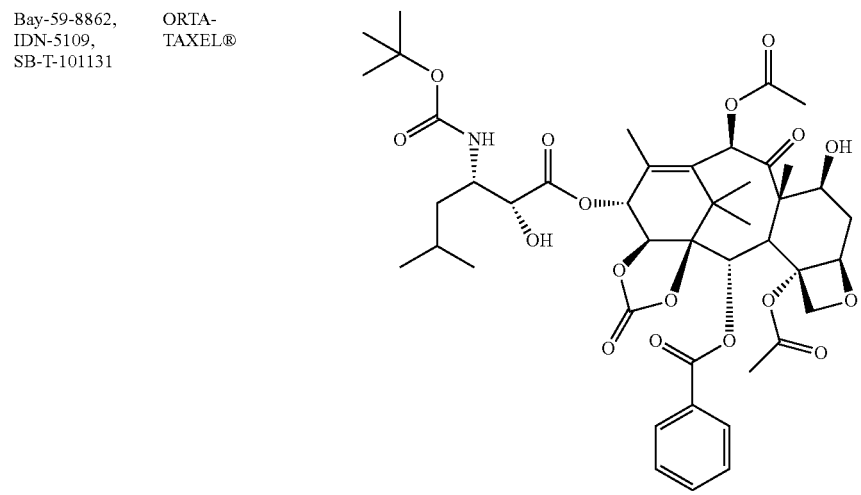 |
| Docosahexaenoyl (DHA)-paclitaxel | TAXOPREXIN® | 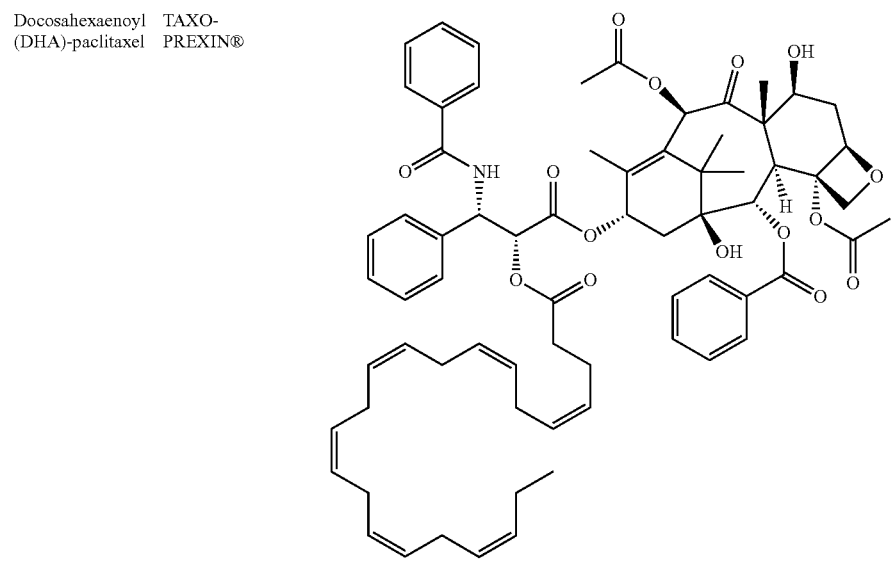 |

-continued

| Common Name | Trade Name | Structure |
|---|---|---|
| TPI-287 | | 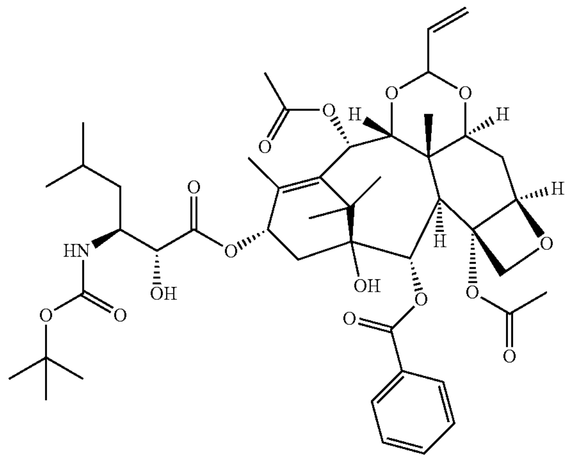 |
| CT-2103 (paclitaxel poliglumex) | XYOTAX® OPAXIO® | 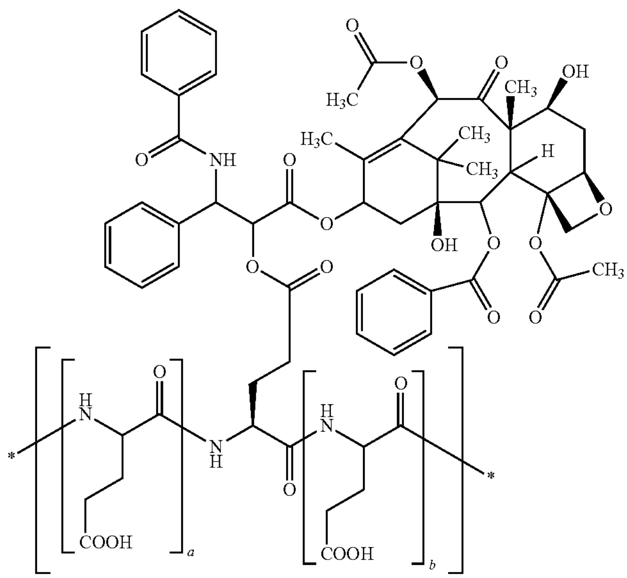 |

As used throughout, "modulation" is meant to refer to an increase or a decrease in the indicated phenomenon (e.g., modulation of a biological activity refers to an increase in a biological activity or a decrease in a biological activity).

Probiotic Bacteria.

Various strains of probiotic bacteria find use in the methods of the invention, including without limitation *Streptococcus thermophilus, Bifidobacterium longum, Bifidobacterium breve, Bifidobacterium infantis, Lactobacillus acidophilus, Lactobacillus plantarum, Lactobacillus casei,* and *Lactobacillus bulgaricus*, or a combination thereof. For example a combination of all 8 strains may be used, herein referred to as AJ2. The bacteria may be sonicated before contacting with NK cells. The ratio of bacteria to NK cells may be used at a cell:cell ratio of 10:1; 5:1, 1:1, 1:5, 1:10, etc. The presence of the probiotic bacteria increases cytokine production by the NK cells, including IFNγ and IL-10. Three probiotic bacteria strains: *Streptococcus thermophilus, Bifidobacterium longum,* and *Bifidobacterium breve*, and a mixture of eight probiotic strains, AJ2, produce significantly higher cytokine levels in NK cells. The addition of probiotic bacteria to NK treated with IL-2 and anti-CD16mAb significantly accelerates cytokine production capability of the NK cells.

By "pluripotency" and pluripotent stem cells it is meant that such cells have the ability to differentiate into all types of cells in an adult organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPS cells" it is meant that the differentiated somatic cells can be induced to become, i.e. can be reprogrammed to become, iPS cells. In other words, the somatic cell can be induced to redifferentiate so as to establish cells having the morphological characteristics, growth ability and pluripotency of pluripotent cells. iPS cells have an hESClike morphology, growing as flat colonies with large nucleocytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, pluripotent cells are capable of forming teratomas. In addition, they are capable of forming or contributing to ectoderm, mesoderm, or endoderm tissues in a living organism.

Stem Cells and Cultures Thereof.

Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human iPS and human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2): 205-16; etc.) The stem cells may be obtained from any mammalian species, e.g. human, equine, bovine, porcine, canine, feline, rodent, e.g. mice, rats, hamster, primate, etc.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection.

Progenitor or Differentiated Cells.

A "differentiated cell" is a cell that has progressed further down the developmental pathway than the cell it is being compared with. Thus, embryonic stem cells can differentiate to lineage-restricted progenitor cells (such as a mesodermal stem cell), which in turn can differentiate into other types of progenitor cells further down the pathway (such as an cardiomyocyte progenitor), and then to an end-stage differentiated cell, which plays a characteristic role in a certain tissue type, and may or may not retain the capacity to proliferate further. For the purposes of the present invention, progenitor cells are those cells that are committed to a lineage of interest, but have not yet differentiated into a mature cell.

The potential of ES cells to give rise to all differentiated cells provides a means of giving rose to any mammalian cell type, and so a very wide range of culture conditions may be used to induce differentiation, and a wide range of markers may be used for selection. One of skill in the art will be able to select markers appropriate for the desired cell type.

Among the differentiated cells of interest are cells not readily grown from somatic stem cells, or cells that may be required in large numbers and hence are not readily produced in useful quantities by somatic stem cells. Such cells may include, without limitation, neural cells, oligodendrocytes, pancreatic islet cells, hematopoietic cells, cardiac muscle cells, etc.

For example, NCAM may be used as a marker for the selection of aggregates comprising neural lineage cells, inter alia (see Kawasaki et al. (2002) PNAS 99:1580-1585). Neuronal subpopulations can be derived from in vitro differentiation of embryonic stem (ES) cells by treatment of embryo-like aggregates with retinoic acid (RA). The cells express Pax-6, a protein expressed by ventral central nervous system (CNS) progenitors. CNS neuronal subpopulations generated expressed combinations of markers characteristic of somatic motoneurons (Islet-1/2, Lim-3, and HB-9), cranial motoneurons (Islet-1/2 and Phox2b) and interneurons (Lim-1/2 or EN1) (Renoncourt et al. (1998) Mech Dev. 179(1-2):185-97; Harper et al. (2004) PNAS 101(18):7123-8).

Another lineage of interest is pancreatic cells. The pancreas is composed of exocrine and endocrine compartments. The endocrine compartment consists of islets of Langerhans, clusters of four cell types that synthesize peptide hormones: insulin ($\beta$ cells), glucagon ($\alpha$ cells), somatostatin ($\gamma$ cells), and pancreatic polypeptide (PP cells). Although the adult pancreas and central nervous system (CNS) have distinct origins and functions, similar mechanisms control the development of both organs. Strategies that induce production of neural cells from ES cells can be adapted for endocrine pancreatic cells. Useful culture conditions include plating EBs into a serum-free medium, expansion in the presence of basic fibroblast growth factor (bFGF), followed by mitogen withdrawal to promote cessation of cell division and differentiation.

Expression of nestin may be useful as a marker for selection of a number of progenitor cells from embryoid bodies. The cells in the pancreatic lineages express GATA-4 and HNF3, as well as markers of pancreatic $\beta$ cell fate, including the insulin I, insulin II, islet amyloid polypeptide (IAPP), and the glucose transporter-2 (GLUT 2). Glucagon, a marker for the pancreatic $\alpha$ cell, may also induced in differentiated cells. The pancreatic transcription factor PDX-1 is expressed. These ES cell-derived differentiating cells have been shown to self-assemble into structures resembling pancreatic islets both topologically and functionally (Lumelsky et al. (2001) Science 292(5520):1389-94.

Derivation of hematopoietic lineage cells is also of interest. Hematopoietic stem cells and precursors have been well-characterized, and markers for the selection thereof are well known in the art, e.g. CD34, CD90, c-kit, etc. Co-culture of human ES cells with irradiated bone marrow stromal cell lines in the presence of fetal bovine serum (FBS), but without other exogenous cytokines, leads to differentiation of the human ES cells within a matter of days. A portion of these differentiated cells express CD34, the best-defined marker for early hematopoietic cells (Kaufman and Thomson (2002) J Anat. 200 (Pt 3):243-8). $CD34^+$ and $CD34^+CD38^-$ cells derived from ES cell cultures have a high degree of similarity in the expression of genes associated with hematopoietic differentiation, homing, and engraftment with fresh or cultured bone marrow (Lu et al. (2002) Stem Cells 20(5):428-37.

A "cardiomyocyte precursor" is defined as a cell that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Methods of Treatment

Compositions and methods are provided for treatment of cancer, particularly the killing of cancer stem cells, by administration of a composition of natural killer cells. In some embodiments the cancer stem cells are carcinoma stem cells, including without limitation squamous carcinoma stem cells. In some embodiments the cancer stem cells are oral squamous carcinoma stem cells. Cancers are optionally profiled prior to treatment to determine the presence of cancer stem cells, where such cells may be identified by the presence of markers known in the art, including without limitation expression of CD44, CD133, etc., where the presence of the cancer stem cells, e.g. at 0.1%, 1%, 2%, 5% or more of the tumor mass is indicative that the individual is suited for treatment by the methods of the invention.

The methods of the invention involve an initial depletion of effector cells in the tumor microenvironment, for example by irradiation, chemotherapy, and the like, in a dose that is sufficient to substantially deplete monocytes present in the tumor microenvironment. The dose appropriate for the individual may be determined based on the evaluation of the patient, the drug or radiation therapy that is selected, the size and phenotype of the tumor mass, and the like.

NK cells are then delivered to the tumor site, e.g. by localized injection at the site of cancer or in close proximity to the site of cancer, although systemic administration may find use, e.g. when the cancer is metastatic. In some embodiments the NK cells are autologous. In other embodiments the NK cells are allogeneic. Repeated administration of NK cells to lyse cancer stem cells may be required. The effective dose of NK cells may be at least about $10^5$ cells, at least about $10^6$ cells, at least about $10^7$ cells, or more.

Generally the NK cells for use in the methods of the invention have been selected, e.g. by positive or negative selection, from an appropriate cell source, e.g. peripheral blood monocytes (PBMC), etc. Methods and markers for the enrichment of NK cells are known in the art. For example negative selection may utilize commercially available antibodies that bind to CD3, CD4, CD19, CD66b, glycophorin, etc. Alternatively NK cells may be positively selected for expression of CD56, and/or CD16.

After isolation from the host or a donor, the NK cells are activated, e.g. with an effective dose of IL-2, e.g. at least about 10 units/ml, at least about 100 units/ml, at least about 1000 units/ml or more, which increases the cytotoxic function of NK cells and expands the numbers of NK cells. The IL-2 is optionally combined with one or more of IL12 and IFN-α at a dose effective to enhance cytotoxicity and expansion of the NK cells. Cells are cultured in the cytokines for a period of time sufficient for activation, e.g. at least about 12 hours, at least about 24 hours, at least about 48 hours and not more than about 4 days, usually not more than about 3 days. Prior to use the NK cells may be typically washed free of excess cytokines. The cells are typically resuspended in an pharmaceutically acceptable excipient, and injected into the patient at an intra-tumoral or systemic site, e.g. i.v., sub-cutaneous, intramuscular, etc.

In some embodiments, a sequential procedure is used to treat cancer. An effective dose of IL-2 treated and washed NK cells are brought into contact with the tumor cell population, which has the effect of killing cancer stem cells. NK cells can be further used to differentiate cancer stem cells. For example, an effective dose of NK cells treated with IL-2, anti-CD16, and autologous monocytes or osteoclasts can be administered for differentiation of residual cancer stem cells. The NK cells can be additionally treated with sonicated probiotic bacteria to increase cytokine expression. As a final step the cancer can be treated with a chemotherapeutic agent to eliminate the differentiated tumor cells, e.g. with paclitaxel and NAC.

The methods of the invention may be combined with additional therapy targeted at cancer cells, including, without limitation, a therapeutic dose of a taxane and N-acetylcysteine. Alternative, the combination of a taxane and NAC may be used in the absence of NK cells. Taxanes of interest are described herein and include without limitation paclitaxel. The taxane may be provided at a dose that is conventional for the selected agent or at a dose that is less than a conventional dose, e.g. paclitaxel may be used at a dose of from about 25 mg/m$^2$, 50 mg/m$^2$; 75 mg/m$^2$; 100 mg/m$^2$; 125 mg/m$^2$; 150 mg/m$^2$; 175 mg/m$^2$; 200 m g/m$^2$; 225 mg/m$^2$; and in combination with N-acetylcysteine, which is shown herein to synergize with taxanes to kill cancer stem cells. N-acetylcysteine may be administered in, for example, an oral dose, at a dose of from about 10 mg/kg body weight; 25 mg/kg body weight; 50 mg/kg body weight; 75 mg/kg body weight; 100 mg/kg body weight; 125 mg/kg body weight; 150 mg/kg body weight; 175 mg/kg body weight; 200 mg/kg body weight. Dosing may be repeated twice or more daily, daily, semi-weekly, weekly, and will generally be monitored for reduction of tumor cells.

An effective amount of such agents can readily be determined by routine experimentation, as can the most effective and convenient route of administration and the most appropriate formulation. Various formulations and drug delivery systems are available in the art. (See, e.g., Remington's Pharmaceutical Sciences, supra.)

Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions and the like, for oral ingestion by a subject. The agents may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration.

Compositions formulated for parenteral administration by injection, e.g., by bolus injection or continuous infusion can be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of the compound or agent to be administered, including in water-soluble form.

Suspensions of the active agents may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, the active ingredient may be in powder form for constitution with a suitable vehicle, e.g., sterile pyrogen-free water, before use.

For any composition employed herein, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Dosage ranges appropriate for human subjects can be determined, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The MEC will vary for each agent but can be estimated from, for example, in vitro data, such as the concentration necessary to achieve 50-90% inhibition of activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases, such as oral cancers.

Methods of Transplantation

Ex vivo and in vitro stem cell populations useful as a source of cells may be obtained from any mammalian species, e.g. human, primate, equine, bovine, porcine, canine, feline, etc., particularly human cells. Ex vivo and in vitro differentiated cell populations may include fresh or frozen cells, which may be from a neonate, a juvenile or an adult, and differentiated tissues including skin, muscle, blood, liver, pancreas, lung, intestine, stomach, and other differentiated tissues. Pluripotent cells are optionally deleted from the differentiated cell population prior to introduction into the recipient. The dose of cells will be determined based on the specific nature of the cell, recipient and nature of condition to be treated, and will generally include from about $10^6$-$10^{10}$ cells, which may be provided in suspension, as aggregates, and the like.

To determine the suitability of cell compositions for therapeutic administration, the cells can first be tested in a suitable animal model. At one level, cells are assessed for their ability to survive and maintain their phenotype in vivo. The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

The stem cells may be used for tissue reconstitution or regeneration in a human patient or other subject in need of such treatment. The cells are administered in a manner that permits them to graft or migrate to the intended tissue site and reconstitute or regenerate the functionally deficient area.

The NK cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types, especially endothelial cells.

Cells may be genetically altered in order to introduce genes useful in the differentiated cell, e.g. repair of a genetic defect in an individual, selectable marker, etc. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over a 8-16 h period, and then exchanged into growth medium for 1-2 days. Genetically altered cells are selected using a drug selection agent such as puromycin, G418, or blasticidin, and then recultured.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

For further elaboration of general techniques useful in the practice of this invention, the practitioner can refer to standard textbooks and reviews in cell biology, tissue culture, and embryology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Example 1

Increased Lysis of Stem Cells But Not Their Differentiated Cells by Natural Killer Cells; De-Differentiation or Reprogramming Activates NK Cell Cytotoxicity The aim of this study is to demonstrate the increased lysis of stem cells but not their differentiated counterparts by the NK cells, and to determine whether disturbance in cell differentiation is a cause for increased sensitivity to NK cell mediated cytotoxicity. Increased cytotoxicity and augmented secretion of IFN-γ were both observed when PBMCs or NK cells were co-incubated with primary UCLA oral squamous carcinoma stem cells (UCLA-OSCSCs) when compared to differentiated UCLA oral squamous carcinoma cells (UCLA-OSCCs). In addition, human embryonic stem cells (hESCs) and human dental pulp stem cells (hDPSCs) were also lysed greatly by the NK cells. Moreover, NK cells were found to lyse human Mesenchymal Stem Cells (hMSCs), and human induced pluripotent stem cells (iPSCs) significantly more than their differentiated counterparts or parental lines from which they were derived. It was also found that inhibition of differentiation or reversion of cells to a less differentiated phenotype by blocking NFκB or targeted knock down of COX2 significantly augmented NK cell cytotoxicity and secretion of IFN-γ. Taken together these results demonstrate that stem cells are significant targets of the NK cell cytotoxicity, however, to support differentiation of stem cells, NK cells may be required to lyse a great number of stem cells and/or those which are either defective or incapable of full differentiation in order to lose their cytotoxic function and gain in cytokine secretion capacity (split anergy). Therefore, patients with cancer may benefit from repeated allogeneic NK cell transplantation for specific elimination of cancer stem cells.

Here we demonstrate that blocking NFκB in these cells increased the activation of NK cell cytotoxicity. We also used an immortalized but non tumorigenic oral keratinocytes HOK-16B since they were previously used as a model of dysplasia in a cancer progression model.

In this report we demonstrate that the stage of maturation and differentiation of the cells is predictive of their sensitivity to NK cell lysis. Thus, UCLA-OSCSCs, which are less differentiated oral tumors are significantly more susceptible to NK cell mediated cytotoxicity; however, their differentiated counterparts UCLA-OSCCs are significantly more resistant. In addition, both hESCs and iPSCs as well as a number of other stem cells such as hMSCs and hDPSCs were found to be significantly more susceptible to NK cell mediated cytotoxicity. Based on these results, it is found that NK cells can play a significant role in differentiation of the cells by providing critical cytokines. However, to drive differentiation, NK cells will have to first receive signals from undifferentiated stem cells or those which have disturbed or defective capabilities to differentiate in order to lose cytotoxicity and gain in cytokine producing phenotype. These alterations in NK cell effector function will ultimately aid in driving differentiation of a minor population of surviving healthy as well as transformed cells. In cancer patients since the majority of NK cells have lost cytotoxic activity, they cells may eventually contribute rather than halt the progression of cancer by not only driving the differentiation of tumor cells but more importantly, by allowing the growth and expansion of the pool of cancer stem cells.

Materials and Methods

Cell Lines, Reagents, and Antibodies. RPMI 1640 supplemented with 10% FBS was used for the cultures of human and mouse NK cells and human PBMCs. UCLA-OSCCs and UCLA-OSCSCs were isolated from freshly resected tongue tumors, and were cultured in RPMI 1640 supplemented with 10% FCS. Recombinant IL-2 was obtained from NIH-BRB. The mouse and human NK and monocyte purification kits were obtained from Stem Cell Technologies (Vancouver, Canada). The anti-CD133 and CD44 were obtained from Miltenyi biotec (Auburn, Calif.). Antibody to CD90 was purchased from Pharmingen/BD (San Diego, Calif.). Antibodies for CD16 and B7H1 were purchased from ebiosciences (San Diego, Calif.). EGFR antibody (Erbitox) was purchased from UCLA pharmacy. The antibodies against p65 subunit of NFκB and pSTAT3 were purchased from Santa Cruz (Santa Cruz, Calif.). Blocking antibodies against CD126 were purchased from Biosource (Camarillo, Calif.).

Human Mesenchymal stem cells (hMSCs), human Embryonic Stem cells (hESCs), human Dental Pulp Stem cells (hDPSCs), human induced pluripotent stem cells (hiPSCs). hMSCs were obtained from Poietics, Cambrex Bio Science (Walkerville, Md.) and they were cultured in Mesenchymal Stem Cell Basal Medium (MSCBM) supplemented with Mesenchymal Cell Growth Supplement (MCGS) (Cambrex Bio Science Walkerville, Md.). The MSCs were differentiated into osteoblasts using Osteogenic differentiation media which comprises of Osteogenic Differentiation BulletKit® that contains Basal Medium and one Osteogenic SingleQuot Kit® also purchased from Cambrex Bio Science. (Walkerville, Md.). Human Mesenchymal stem cells were cultured in Mesenchymal Stem Cell Basal Medium (MSCBM) with the growth supplements according to the manufacturer's recommendations. For the induction of osteogenesis, MSC were seeded at a density of ($1 \times 10^4$ cells/well) in Osteogenic media with the recommended supplements. Media was replaced every three days and the cells were used in the experiments when they were 80% confluent.

hDPSCs were isolated as described previously and they were cultured in complete DMEM supplemented with 10% FBS. DPSCs were differentiated using b-glycerophosphate, ascorbic acid and dexamethasone as reported previously. hESC line H9 and hiPSC line hiPSC18 were used in this study. H9 and hiPSC18 were used at passages 45-50. hESC and hiPSC were grown on irradiated mouse embryonic fibroblasts (MEFs) in DMEM/F12 supplemented with 20% Knockout serum replacement (Invitrogen), 1 mM glutamine, 1× nonessential amino acids (NEAA), and 4 ng/ml of bFGF as previously described. 2-mercaptoethanol (1 mM Sigma) and penicillin/streptomycin (Hyclone) were added to growing cultures. For coculture assays, cells were seeded at a density of $10^5$ cells/well on Matrigel (BD Sciences) in conditioned media. Neonatal human dermal fibroblasts (NHDF-iPSC parental fibroblast line from ATCC) were cultured in DMEM supplemented with 10% FBS, 1 mM glutamine, 1×NEAA and penicillin/streptomycin.

Purification of human and mouse NK cells and monocytes. PBMCs from healthy donors were isolated as described before. Briefly, peripheral blood lymphocytes were obtained after Ficoll-hypaque centrifugation and purified NK cells were negatively selected by using an NK cell isolation kit (Stem Cell Technologies, Vancouver, Canada). The purity of NK cell population was found to be greater than 90% based on flow cytometric analysis of anti-CD16 antibody stained cells. The levels of contaminating CD3+ T cells remained low, at 2.4%±1%, similar to that obtained by the non-specific staining using isotype control antibody throughout the experimental procedures. The adherent subpopulation of PBMCs was detached from the tissue culture plates and monocytes were purified using isolation kit obtained from Stem Cell Technologies (Vancouver, Canada). Greater than 95% purity was achieved based on flow cytometric analysis of CD14 antibody stained monocytes. Written informed consents approved by UCLA Institutional Review Board (IRB) were obtained from the blood donors and all the procedures were approved by the UCLA-IRB.

Single cell preparations of mouse splenocytes were used to negatively select for mouse NK cells using mouse NK isolation kit purchased from Stem Cell Technologies (Vancouver, Canada). The purity of mouse NK cells were greater than 90% based on staining with NK1.1 and DX5 antibodies. Murine monocytes were purified from bone marrow using monocyte isolation kit obtained from Stem Cell Technologies (Vancouver, Canada). The purity of monocytes was greater than 90% based on staining with anti-CD14 antibody.

ELISA and Multiplex Cytokine Array kit: Single ELISAs were performed as described previously. Fluorokine MAP cytokine multiplex kits were purchased from R&D Systems (Minneapolis, Minn.) and the procedures were conducted as suggested by the manufacturer. To analyze and obtain the cytokine concentration, a standard curve was generated by either two or three fold dilution of recombinant cytokines provided by the manufacturer. Analysis was performed using the Star Station software.

Surface and DNA Staining and apoptosis assay: Staining was performed by labeling the cells with antibodies as described previously Jewett et al. (1997). *J Immunol* 159 (10): 4815-22.

Western Blot. Treated and untreated cells were lysed in a lysis buffer containing 50 mM Tris-HCL (pH 7.4), 150 mM NaCl, 1% Nonidet P-40 (v/v), 1 mM sodium orthovanadate, 0.5 mM EDTA, 10 mM NaF, 2 mM PMSF, 10 μg/mL leupeptin, and 2 U/mL aprotinin for 15 minutes on ice. The samples were then sonicated for 3 seconds. The cell lysates were centrifuged at 14,000 rpm for 10 minutes and the supernatants were removed and the levels of protein were quantified by the Bradford method. The cell lysates were denatured by boiling in 5×SDS sample buffer. Equal amounts of cell lysates were loaded onto 10% SDS-PAGE and transferred onto Immobilon-P membranes (Millipore, Billerica Mass.). The membranes were blocked with 5% non-fat milk in PBS plus 0.1% Tween-20 for 1 hour. Primary antibodies at the predetermined dilution were added for 1 hour at room temperature. Membranes were then incubated with 1:1000 dilution of horseradish peroxidase-conjugated secondary antibody. Blots were developed by enhanced chemiluminescence (ECL—purchased from Pierce Biotechnology, Rockford, Ill.).

$^{51}$Cr release cytotoxicity assay. The $^{51}$Cr release assay was performed as described previously (Jewett, Wang et al. 2003). Briefly, different numbers of purified NK cells were incubated with $^{51}$Cr-labeled tumor target cells. After a 4 hour incubation period the supernatants were harvested from each sample and counted for released radioactivity using the gamma counter. The percentage specific cytotoxicity was calculated as follows;

$$\% \text{ Cytotoxicity} = \frac{\text{Experimental cpm} - \text{spontaneous cpm}}{\text{Total cpm} - \text{spontaneous cpm}}$$

LU 30/$10^6$ is calculated by using the inverse of the number of effector cells needed to lyse 30% of target cells×100.

Retroviral and lentiviral transduction. UCLA-OSCCs were infected with culture supernatants of NIH 3T3 packaging cells transfected with either IκB$_{(S32A S36A)}$super-repressor or mutant IκBα (IκBαM) or their EGFP control vectors. The retroviral vectors were generated in Dr. Nicholas Cacalano's laboratory. Forty eight hours after infection the UCLA-OSCCs or HOK-16B cells were sorted for high expressing GFP cells and were grown and used in the experiments.

NFκB-Luciferase lentiviral reporter vector was produced by co-transfection of the packaging cell line 293T using Calcium Phosphate precipitation. UCLA-OSCCs and UCLA-OSCSCs were seeded at a density of 2×$10^5$ cells per well in a 6-well culture plate 24 hrs before transduction. The following day, cells were transduced with the NFκB-Luciferase lentiviral reporter vector. To enhance transduction efficiency, the cationic polymer Polybrene was used at a final concentration of 8 μg/ml. After six hours of incubation, medium was re-freshed and transduced cells were incubated for an additional 42 hours. Cells were then harvested, lysed and luciferase activity was measured [RLU/s] using a luminometer. An internal lentiviral vector control constitutively expressing Luciferase was used to normalize values.

Luciferase reporter assay: Transfections were also performed using NFκB Luciferase reporter vector and Lipofectamine 2000 reagent (Invitrogen, CA) in Opti-MEM media (Invitrogen, CA) for 18 hours after which they were adhered to the plate overnight before different immune effectors at 1:1 Effector to target ratios were added. The cells were then lysed with lysis buffer and the relative Luciferase activity was measured using the Luciferase assay reagent kit obtained from Promega (Madison, Wis.).

Alkaline Phosphatase (ALP) staining. Human MSCs were co-cultured with and without untreated and IL-2 treated PBMCs as indicated in the result section. Cells were then washed twice with PBS and incubated with 120 mM of Tris buffer (pH=8.4) containing 0.9 mM Napthol AS-M Phosphate and 1.8 mM Fast Red TR (both purchased from Sigma, MO) for 30 minutes at 37° C. After 30 minute incubation, cells were washed three times with PBS and then fixed with 1 ml cold ethanol (100%) for 30 minutes. The stained cultures were scanned using an Epson scanner 1250.

Statistical analysis: An unpaired, two-tailed student t-test was performed for the statistical analysis. One way ANOVA with a Bonferroni post-test was used to compare the different groups.

Results

Figure 1B:
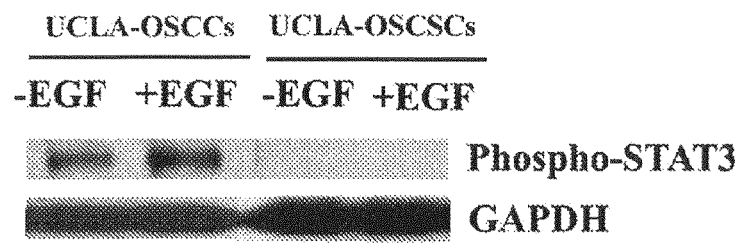
Figure 1C:
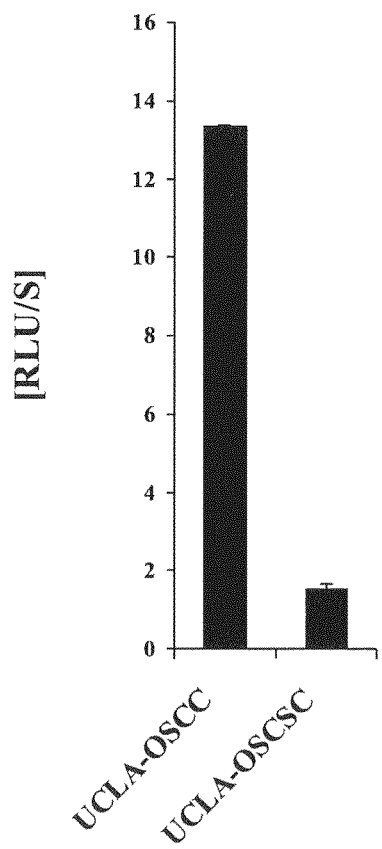

Identification and characterization of patient-derived primary oral squamous cancer stem cells (UCLA-OSCSCs). We screened a number of different primary oral squamous cell carcinomas (OSCC) derived from patients at UCLA, and selected to concentrate on two specific primary tumors based on their phenotypic characteristics and sensitivity to NK cell mediated cytotoxicity. UCLA-OSCCs were found to have higher surface expression of B7H1 and EGF-R and moderate expression of CD44 and no surface expression of CD133 whereas UCLA-OSCSCs expressed no or very low expression of B7H1, EGF-R and very high expression of CD133 and CD44$^{bright}$. No surface expression of MHC-Class II or CD90 could be seen on either tumor type (FIG. 1A). In addition, UCLA-OSCSCs secreted no or very low levels of IL-6, IL-8 and GM-CSF whereas they secreted higher levels of VEGF when compared to UCLA-OSCCs (Tables 1 and 2). Moreover, they did not express phospho-Stat3 when cultured in the presence and absence of EGF (FIG. 1B). More importantly, no or very low NFkB activity could be detected in UCLA-OSCSCs when compared to UCLA-OSCCs (FIG. 1C). Therefore, the profiles of cytokines secreted by UCLA-OSCCs and UCLA-OSCSCs resembled those of vector alone and IκB$_{(S32AS36A)}$ super-repressor transfected HEp2 cells respectively (Table 2). Thus, UCLA-OSCSCs express phenotypic characteristics of oral cancer stem cells. Furthermore, they were smaller in size and proliferated at a much higher rate when compared to UCLA-OSCC cells. We used these two primary oral tumors to study NK cell activation.

Figure 2A:
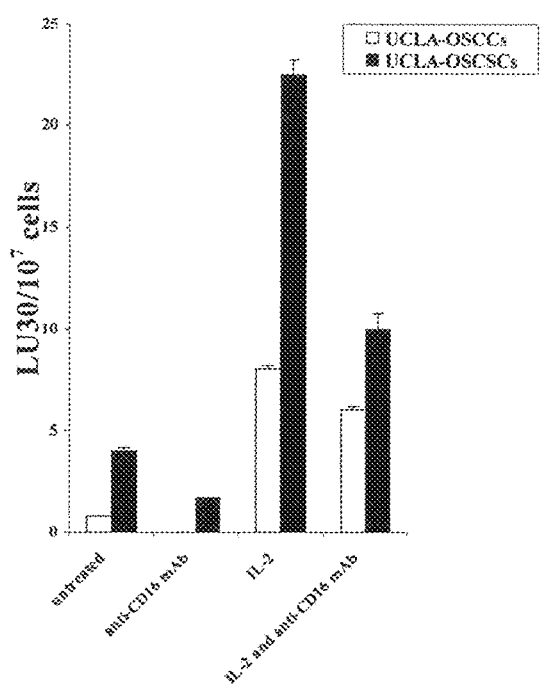
FIGS. 2A-2B Increased NK cell cytotoxicity against UCLA-OSCSCs. PBMCs and NK cells were left untreated or treated with IL-2 (1000 units/ml) or anti-CD16 mAb (3 μg/ml) or a combination of IL-2 (1000 units/ml) and anti-CD16mAb (3 μg/ml) for 12-24 hours before they were added to $^{51}$Cr labeled primary oral tumors. PBMC (FIG. 2A) and NK cell (FIG. 2B) cytotoxicity was determined using a standard $^{51}$Cr release assay and the lytic units $30/10^6$ were determined using inverse number of effectors required to lyse 30% of the tumor cells×100. Differences between untreated, anti-CD16mAb treated or IL-2 and/or anti-CD16mAb treated NK cell killing between UCLA-OSCCs and UCLA-OSCSCs were significant at a p value of <0.05. One of four representative experiments is shown in this figure.
Figure 2B:
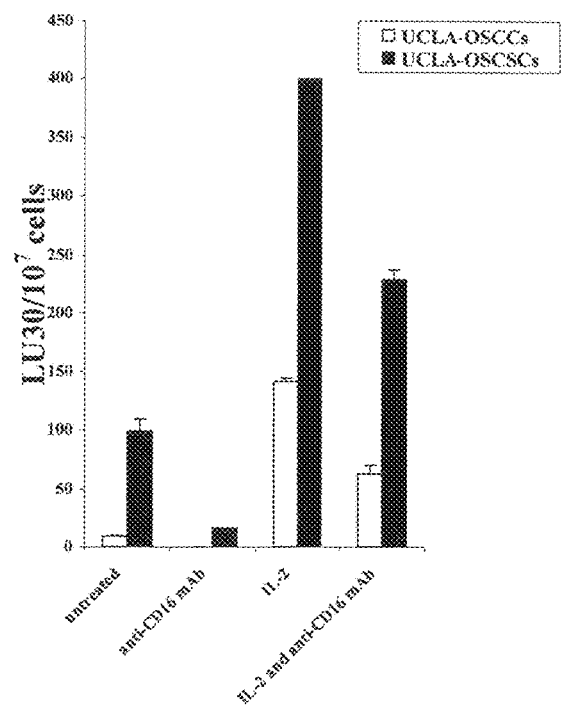

Increased NK cell cytotoxicity against UCLA-OSCSCs but not those of UCLA-OSCCs. We have previously shown that blocking NFκB in HEp2 tumor cells decreased IL-6 and IL-8 secretion substantially and resulted in an increased sensitivity of HEp2 tumor cells to NK cell mediated cytotoxicity. Therefore, using the levels of cytotoxicity, IFN-γ and IL-6 secretion, we could demonstrate a direct correlation between decreased IL-6 and increased IFN-γ secretion in the co-cultures of NK cells with NFκB knock down HEp2 cells and increased susceptibility to IL-2 activated NK cell killing. Induction of NK cell anergy by anti-CD16 antibody abrogated the ability of IL-2 treated NK cells to lyse HEp2 cells, even though the same treatment resulted in a significant induction of IFN-γ secretion in the co-cultures of NK cells with HEp2 cell transfectants. To extend our findings to patient derived oral tumors, UCLA-OSCC and UCLA-OSCSCs were tested for their sensitivity or resistance to NK cell mediated cytotoxicity. The cytotoxic activities of IL-2 treated PBMCs (FIG. 2A) and NK cells (FIG. 2B) were significantly higher against UCLA-OSCSCs cells when compared to UCLA-OSCCs. Untreated PBMCs or NK cells lysed UCLA-OSCSCs tumors significantly more than UCLA-OSCCs (FIG. 2B). However, the levels of lysis by untreated NK cells were considerably lower than that obtained by IL-2 treated PBMCs or NK cells (FIGS. 2A and 2B). Treatment of PBMCs or NK cells with anti-CD16 mAb decreased cytotoxicity significantly against both tumor types, however, the levels of lysis by the NK cells remained higher against UCLA-OSCSCs in all the NK samples tested (FIG. 2). IL-2 treated NK cells co-cultured with UCLA-OSCSCs oral tumor cells exhibited higher expression of CD69 activation antigen when compared to those co-cultured with UCLA-OSCC oral tumors.

Increased induction of IFN-γ was paralleled with a decreased secretion of IL-6 in co-cultures of NK cells with UCLA-OSCSCs oral tumors. Untreated and IL-2 treated NK cells were co-cultured with UCLA-OSCC and UCLA-OSCSCs and the induction of a number of key cytokines, including those which were correlated with NK resistant tumor phenotype, were determined in the supernatants recovered from the co-cultures of the immune effectors with oral tumors after an overnight incubation. In the presence of untreated NK cells co-cultured with UCLA-OSCC, synergistic induction of GM-CSF, IL-6 and IL-8 could be observed since much lower levels of these cytokines were induced either in the presence of immune effectors alone or tumor cells alone (Table 2). The levels of above-mentioned cytokines were considerably lower in the co-cultures of untreated NK cells with UCLA-OSCSCs (Table 2). VEGF secretion was significantly higher in UCLA-OSCSCs, the levels exceeded that of the baseline levels produced by the tumor cells alone when untreated NK cells were co-cultured with UCLA-OSCC cells and not that of UCLA-OSCSCs (Table 2). Increased GM-CSF secretion in the presence of UCLA-OSCCs as compared to UCLA-OSCSCs was more evident in untreated NK cells (Table 2).

NK cell sensitivity of tumors correlated with an increased IFN-γ secretion in the presence of lower IL-6 and IL-8 secretion in IL-2 activated NK cells co-cultured with UCLA-OSCSCs (Table 2). Indeed, when ratios of IL-6 to IFN-γ were considered a direct correlation between sensitivity to NK cell mediated killing and decreased ratios of IL-6 to IFN-γ could be seen (Table 2). Finally, both cell lines exhibited lower amounts of VEGF secretion in the presence of IL-2 treated NK cells, indicating the ability of IL-2 treated NK cells to exert significant inhibitory effect on VEGF secretion. However, the residual levels remained higher in the co-cultures of IL-2 treated NK cells with UCLA-OSCC than UCLA-OSCSCs when compared to the baseline secretion by the tumors alone (Table 2). Thus, several important cytokine profiles were identified for NK sensitive and resistant oral tumors after their co-culture with NK cells.

Figure 3A:
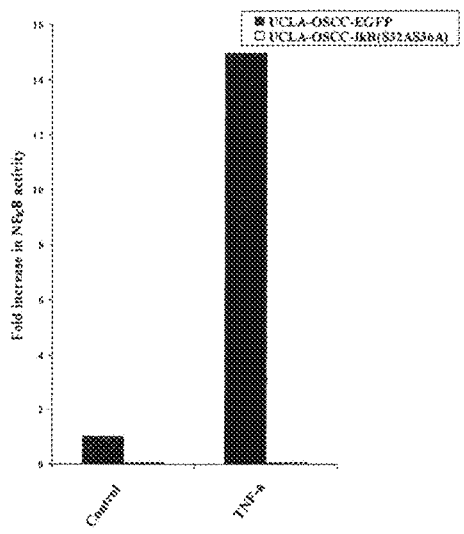
FIGS. 3A-3J Increased cytotoxicity, decreased secretion of IL-6 and increased secretion of IFN-γ in co-cultures of NK cells with NFκB knock down UCLA-OSCCs and HOK-16B cells. IκB$_{(S32AS36A)}$ transduced UCLA-OSCCs (FIG. 3A) and IκBαM transduced HOK-16B cells (FIG. 3B) and their EGFP transduced controls were transfected with 8 μg of NFκB Luciferase reporter vector and treated with and without TNF-α (20 ng/ml) for 18 hours. The relative Luciferase activity was then determined in the lysates according to the manufacturer's recommendation and fold induction in luciferase activity was determined relative to untreated cells. IκB$_{(S32AS36A)}$ transduced UCLA-OSCCs (FIG. 3C) and IκBαM transduced HOK-16B cells (FIG. 3D) and their EGFP transduced controls were cultured at $2\times10^5$ cells/ml, and after an overnight incubation the supernatants were collected and the levels of secreted IL-6 were determined using ELISA specific for IL-6. IκB$_{(S32AS36A)}$ transduced UCLA-OSCCs and IκBαM transduced HOK-16B cells and their EGFP transduced controls were co-cultured with untreated or IL-2 (1000 u/ml) treated NK cells at 1:1 effector to target ratio. After an overnight incubation the supernatants from the co-cultures of UCLA-OSCCs and HOK-16B cells with NK cells were collected and the levels of secreted IL-6 (FIGS. 3E and 3F), and IFN-γ (FIGS. 3G and 3H) were determined by specific ELISAs for each cytokine. NK cells were left untreated or treated with IL-2 for 12-24 hours before they were added to IκB$_{(S32A S36A)}$ transduced UCLA-OSCCs and IκBαM transduced HOK-16B cells and their EGFP transduced controls. Differences between EGFP transduced and those with either IκB$_{(S32A S36A)}$ transduced UCLA-OSCCs or IκBαM transduced HOK-16B cells were significant for IL-2 treated NK cells at a p value of <0.05. IκB$_{(S32A S36A)}$ transduced UCLA-OSCCs and IκBαM transduced HOK-16B cells and their EGFP transduced controls were $^{51}$Cr labeled before they were co-cultured with untreated or IL-2 (1000 u/ml) treated NK cells. After 4 hours of incubation at 37 C cytotoxicity of NK cells were assessed using a standard $^{51}$Cr release assay (FIGS. 3I and 3J). lytic unit 30/10$^6$ cells were determined using inverse number of effectors required to lyse 30% of the tumor cells×100. Differences between IκB$_{(S32A S36A)}$ transduced UCLA-OSCCs or IκBαM transduced HOK-16B cells and those with EGFP transduced were significant in IL-2 treated PBMCs at a p value of <0.05. One of three representative experiments is shown in this figure.
Figure 3B:
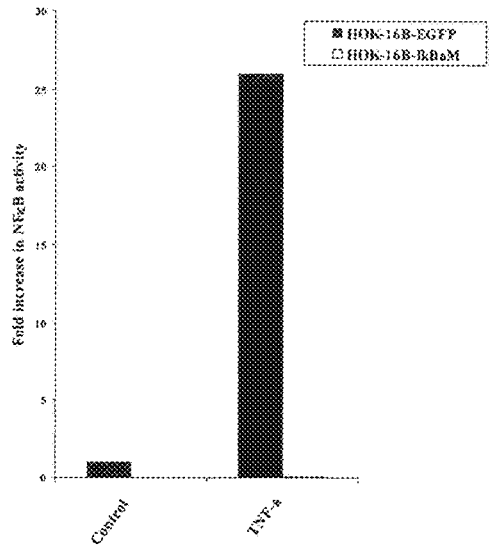

Blocking NFκB in UCLA-OSCCs and HOK-16B oral epithelial cells lowered IL-6 to IFN-γ ratios and increased their sensitivity to NK cell mediated cytotoxicity. As indicated previously UCLA-OSCCs and HOK-16B oral keratinocytes represent an oral cancer progression model since HOK-16B are immortalized but non-tumorigenic, and thus could represent a model of dysplastic keratinocytes. HOK-16B and UCLA-OSCCs were transduced with EGFP alone or IκBαM or IκB$_{(S32AS36A)}$ super-repressor retroviral constructs and sorted for high GFP expressing cells using flow cytometry. The inhibition of NFκB by the IκBαM or IκB$_{(S32AS36A)}$ super-repressor retroviral vector in UCLA-OSCC and HOK-16B was confirmed by measuring NFκB activity using luciferase reporter assay (FIGS. 3A and 3B). IκBαM or IκB$_{(S32AS36A)}$ super-repressor transduced UCLA-OSCC (FIG. 3C) and HOK-16B (FIG. 3D) tumor cells secreted substantially lower levels of IL-6 when compared to EGFP transduced UCLA-OSCCs and HOK-16B cells. Thus, transduction of UCLA-OSCCs and HOK-16B with IκBαM or IκB$_{(S32AS36A)}$ super-repressor constructs exhibited the same functional profiles as those observed in transfected HEp2 oral tumor cells with IκB$_{(S32AS36A)}$ construct. Similar to HEp 2-cell transfectants, UCLA-OSCCs and HOK-16B cells transduced with IκBαM or IκB$_{(S32AS36A)}$ super-repressor constructs did not exhibit elevated levels of cell death when assessed by flow cytometric analysis of Annexin V and PI stained cells. In addition, there was a significant decrease in the surface expression of ICAM-1 in IFN-γ treated IκB$_{(S32AS36A)}$ transduced UCLA-OSCCs (83% decrease) and HOK-16B cells (78% decrease) when compared to EGFP alone transduced cells. These results also indicated that IL-6 secretion in oral tumor cells is regulated by the function of NFκB.

Untreated or IL-2 treated NK cells were added to EGFP or IκB$_{(S32A,S36A)}$ transduced UCLA-OSCCs and IκBαM transduced HOK-16B oral keratinocytes and the levels of IL-6 and IFN-γ secretion were determined in the co-cultures with the NK cells after an overnight incubation. IL-2 activated NK cells secreted lower levels of IL-6 when co-cultured with IκB$_{(S32A,S36A)}$ transduced UCLA-OSCCs (FIG. 3E) and IκBαM HOK-16B (FIG. 3F) cells as compared to EGFP transduced oral keratinocytes. In contrast, higher induction of IFN-γ secretion could be observed in supernatants recovered from the co-cultures of NK cells with IκB$_{(S32A,S36A)}$ transduced UCLA-OSCCs (FIG. 3G) and IκBαM transduced HOK-16B (FIG. 3H) oral keratinocytes as compared to EGFP transduced oral tumors. Similar NK cell response patterns were obtained when NFκB was inhibited in HEp2 cells. Finally, IL-2 treated NK cells lysed NFkB knock down OSCCs (FIG. 3I) and HOK-16B (FIG. 3J) cells significantly more than EGFP transfected cells.

Figure 7A:
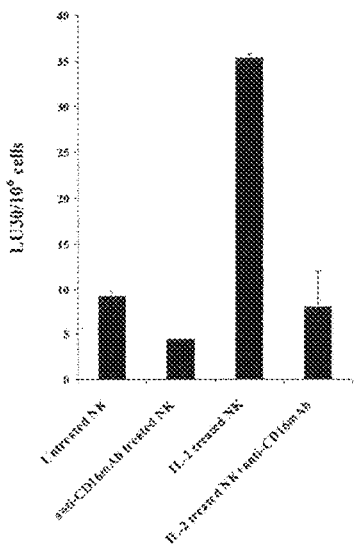
Figure 7B:
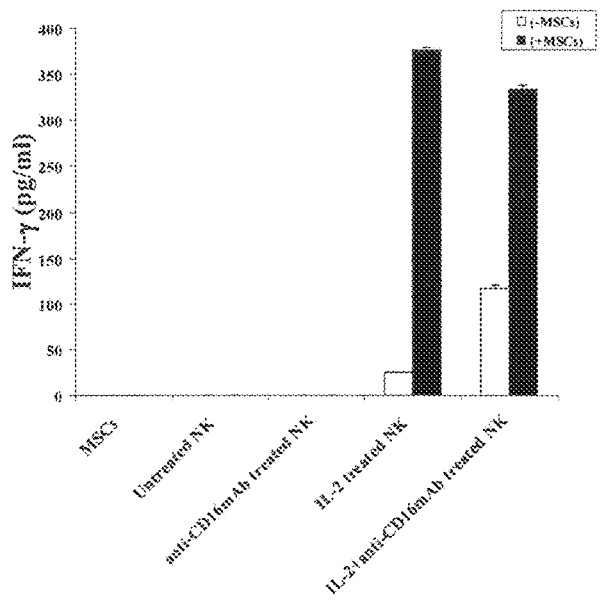
Figure 7C:
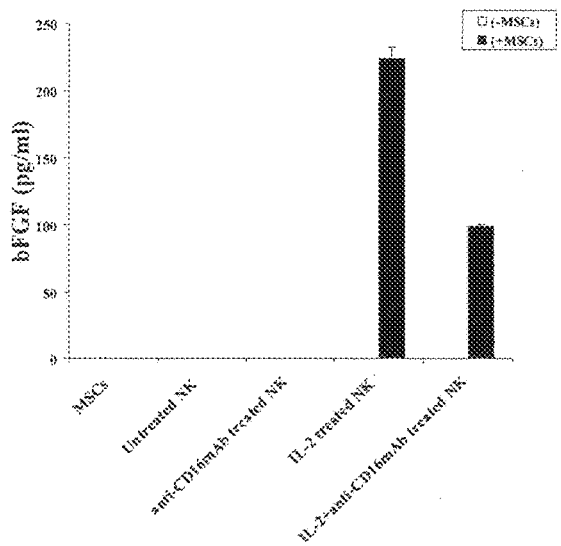

Significant lysis of Embryonic Stem Cells (hESCs), Induced Pluripotent Stem Cells (iPS), Dental Pulp Stem Cells (DPSCs), and Mesenchymal Stem Cells (MSCs) by untreated or IL-2 treated NK cells. Highly purified human NK cells were cultured with and without IL-2 for 12-24 hours before they were added to $^{51}$Cr labeled hESCs (FIG. 4A), iPSCs (FIG. 5A), DPSCs (FIG. 6A) and MSCs (FIG. 7A). Addition of untreated NK cells had lower cytotoxicity against different populations of stem cells whereas activation with IL-2 increased cytotoxicity against all stem cell populations significantly ($p<0.05$) (FIGS. 4A-7A). Therefore, human stem cells are greatly lysed by the NK cells.

Lysis of hESCs, iPSCs, DPSCs, and MSCs by untreated and IL-2 treated NK cells is inhibited by anti-CD16 antibody treatment, however, the same treatment induced significant secretion of IFN-γ by the NK cells in the presence and absence of stem cells. As shown in a number of previous studies anti-CD16 mAb treatment induced anergy in a great majority of the NK cells as well as it induced death in a subset of NK cells, thereby inhibiting NK cell cytotoxicity against different populations of stem cells ($p<0.05$) (FIGS. 4A-7A). Addition of the combination of IL-2 and anti-CD16 treatment also induced anergy and NK cell death and inhibited NK cell cytotoxicity against stem cells when compared to IL-2 activated NK cells ($p<0.05$) (FIGS. 4A-7A). Untreated or anti-CD16 mAb treated NK cells did not secrete IFN-γ when co-cultured with any of the stem cell populations, however, both IL-2 treated and IL-2 in combination with anti-CD16 mAb treated NK cells in the presence and absence of stem cells secreted significant levels of IFN-γ ($p<0.05$) (FIGS. 4B-7B). Indeed, stem cells triggered significant secretion of IFN-γ from IL-2 treated NK cells when compared to IL-2 treated NK cells in the absence of stem cells. In addition, there was a synergistic induction of IFN-γ secretion in IL-2 and anti-CD16 mAb treated NK cells in the absence of stem cells, and the levels either remained the same or exceeded those in the absence of stem cells when IL-2 and anti-CD16mAb treated NK cells were cultured with stem cells (FIGS. 4B-7B). There was a direct correlation between secretion of bFGF by stem cells and cytotoxicity by IL-2 and IL-2+anti-CD16 treated NK cells (FIGS. 4C-7C).

Lysis of MSCs by untreated and IL-2 treated NK cells is inhibited by monocytes, however, the addition of monocytes induced significant secretion of IFN-γ by the NK cells in the presence and absence of stem cells. Monocytes were purified from PBMCs and irradiated as indicated in the Material and Methods section. MSCs were co-cultured with irradiated monocytes for 24-48 hours before they were labeled with $^{51}$Cr and used in the cytotoxicity assays against NK cells. NK cells were left untreated or pre-treated with anti-CD16 antibody and/or IL-2 for 24-48 hours before they were used in the cytotoxicity assays against MSCs. The addition of monocytes to MSCs significantly protected the MSCs (FIG. 7D) from NK cell mediated cytotoxicity ($p<0.05$). Significant inhibition of NK cell cytotoxicity by monocytes could be observed against untreated and IL-2 treated NK samples ($p<0.05$) (FIG. 7D). Monocytes also increased the levels of alkaline phosphatase staining in MSCs and prevented decrease in alkaline phosphatase expression induced by IL-2 activated NK cells. Untreated or anti-CD16 antibody treated irradiated monocytes did not mediate cytotoxicity against MSCs. Overall, these experiments indicated that monocytes protect MSCs against NK cell mediated lysis.

As expected IL-2 treated NK cells secreted moderate amounts of IFN-γ which were synergistically increased when co-cultured in the presence of MSCs ($p<0.05$) (FIG. 7E). The addition of anti-CD16 mAb in combination with IL-2 to NK cells in the absence of MSCs increased secretion of IFN-γ when compared to IL-2 alone treated NK cells in the absence of MSCs. IFN-γ secreted levels remained similar between IL-2 alone and IL-2 and anti-CD16 mAb treated NK cells cultured with MSCs (FIG. 7E). Monocytes added to IL-2 or IL-2 and anti-CD16 antibody treated NK cells in the absence of MSCs or those in the presence of MSCs, synergistically increased the levels of secreted IFN-γ ($p<0.05$) (FIG. 7E). However, the highest increase in IFN-γ release was seen when monocytes were added to IL-2 or IL-2 and anti-CD16 mAb treated NK cells with MSCs (FIG. 7E). These results indicated that monocytes increased IFN-γ in co-cultures with MSCs, and further synergized with IL-2 or IL-2 and anti-CD16 mAb treated NK samples to increase the release of IFN-γ in the co-cultures of NKs and MSCs. Similar results were obtained when NK cells were co-cultured with monocytes and DPSCs.

Figure 8A:
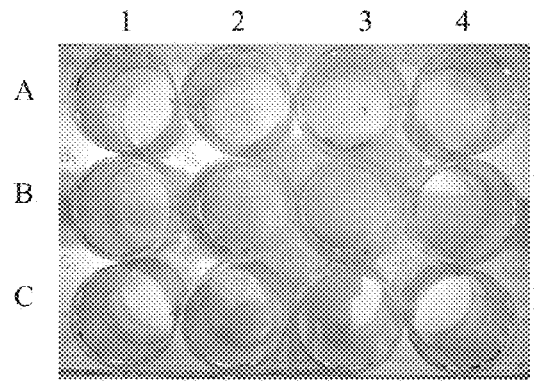
FIGS. 8A-8I MSCs are significantly more sensitive to lysis by IL-2 treated NK cells than their differentiated counterparts and they trigger significant release of IFN-γ by IL-2 activated NK cells. MSCs were seeded at 3 to 4×10$^5$ cells per well in Stem cell medium in the presence and absence of untreated PBMCs or IL-2 (1000 u/ml) treated PBMCs (PBMC to Stem cell ratio 10:1). After 2 days of co-cultures, Alkaline Phosphatase staining was performed. A1 to C1 (triplicates of MSCs in the absence of PBMCs), A2 to C2 (MSC in the presence of untreated PBMCs), A3 to C3 (MSC in the presence of IL-2 treated PBMCs), A4 (naïve PBMCs alone), B4 (IL-2 treated PBMCs alone) (FIG. 8A). The ALP stain densities for each well were determined using photoshop software (FIG. 8B). MSCs were cultured in differentiation medium for 1 week and differentiated Osteoblasts were then seeded at 3 to $4 \times 10^5$ cells per well in differentiation medium in the presence and absence of untreated PBMCs and IL-2 (1000 u/ml) treated PBMCs (PBMC to Stem cell ratio 10:1). After 2 days of co-cultures Alkaline Phosphatase staining was performed. A1 to C1 (triplicates of Ostoblastic cells in the absence of PBMCs), A2 to C2 (Ostoblastic cells in the presence of untreated PBMCs), A3 to C3 (Ostoblastic cells in the presence of IL-2 treated PBMCs), A4 (untreated PBMCs alone), B4 (IL-2 treated PBMCs alone) (FIG. 8C). The ALP stain densities for each well were determined using photoshop software (FIG. 8D). Stem cells and Osteoblasts were cultured with and without untreated PBMCs as described above and after two days of incubation the supernatants were removed and subjected to specific ELISA for VEGF (FIG. 8E). Undifferentiated MSCs and those differentiated to osteoblasts were cultured in the absence and presence of different concentrations of HEMA as indicated in the figure and the levels of cell death were determined by flow cytometric analysis of PI stained MSCs and osteoblasts after an overnight incubation (FIG. 8F). NK cells ($1 \times 10^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled MSCs or osteoblasts, and NK cell cytotoxicity was determined using a standard 4 hour $^{51}$Cr release assay, and the lytic units $30/10^6$ were determined using inverse number of NK cells required to lyse 30% of the MSCs or osteoblasts×100 (FIG. 8G). Undifferentiated MSCs and those differentiated to osteoblasts at ($1 \times 10^5$/ml) were cultured in the absence and presence of untreated NK cells or IL-2 treated NK cells at 1:1 ratio and after two days of incubation the supernatants were removed and subjected to specific ELISA for IFN-γ (FIG. 8H). MSCs at ($1 \times 10^5$/ml) were either cultured with untreated NK cells or IL-2 treated NK cells alone (1:1; MSC:NK) or with untreated NK and IL-2 treated NK cells with monocytes at (1:1:1; MSC:NK:monocytes). After an overnight incubation, the cells were washed and B7H1 surface expression was determined on MSC gated populations. Isotype control antibodies were used as controls (FIG. 8I). MSCs were left untreated or treated with IFN-γ (500 u/ml). After an overnight incubation, MSCs were washed and the B7H1 surface expression was determined on MSC.
Figure 8C:
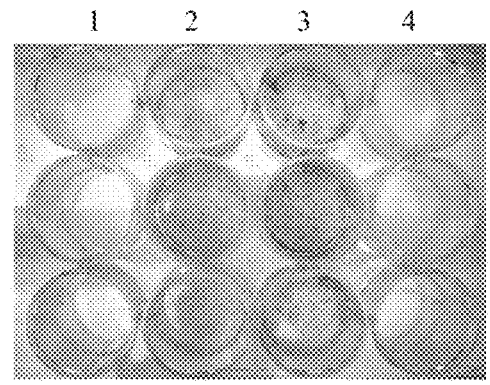
Figure 8B:
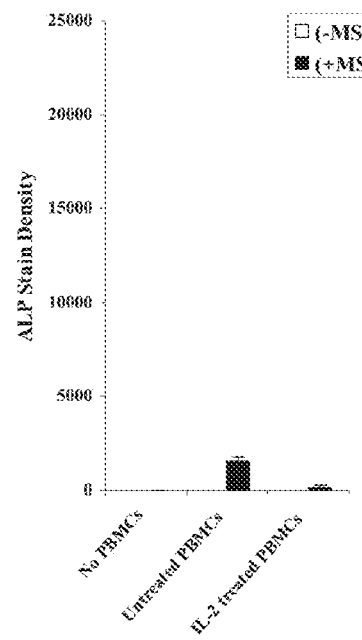
Figure 8D:
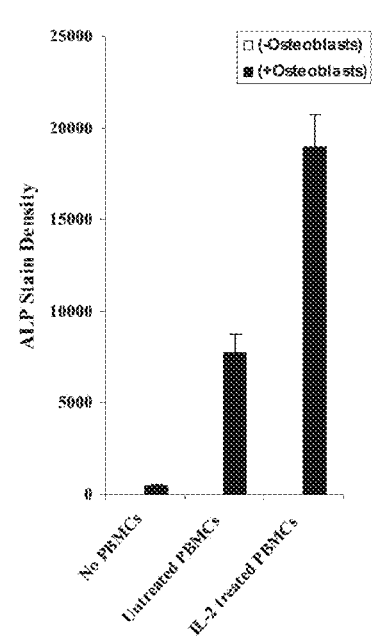
Figure 8:
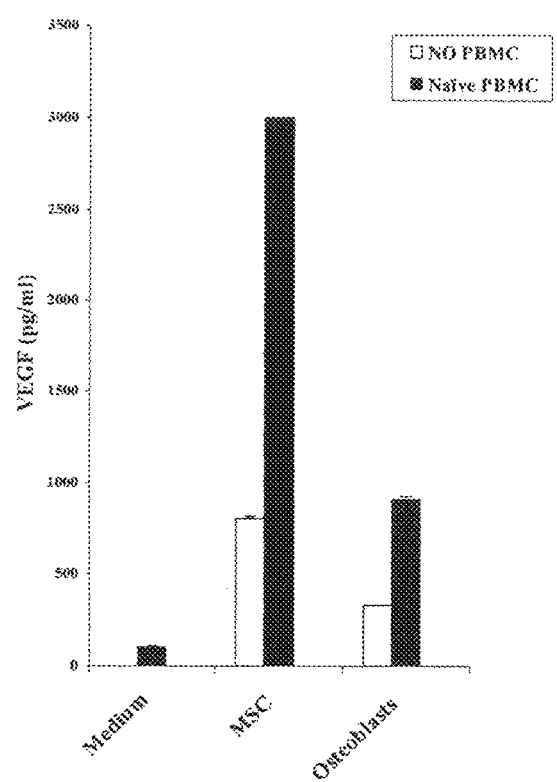

MSCs are significantly more sensitive to lysis by IL-2 treated NK cells than their differentiated counterparts and they trigger significant release of IFN-γ by IL-2 activated NKs. To determine whether differentiation decreases sensitivity of stem cells to NK cell mediated cytotoxicity we chose to concentrate on MSCs. To assess whether differentiation of MSCs similar to oral tumors decreases sensitivity of these cells to NK cell mediated cytotoxicity we determined NK cell cytotoxicity against MSCs and their differentiated osteoblasts using un-fractionated PBMCs as well as NK cells. MSCs were cultured in the absence and presence of untreated and IL-2 treated PBMCs at 10:1 PBMC to MSC ratio and the levels of ALP staining were determined after 2 days of incubation. The addition of untreated PBMCs to MSCs triggered some differentiation of MSCs as assessed by Alkaline Phosphatase (ALP) staining (FIGS. 8A and 8B). No significant staining with ALP can be seen by either the PBMCs or MSCs alone (FIGS. 8A and 8B). Treatment of PBMCs with IL-2 and their subsequent co-culture with MSCs lysed the cells and prevented induction of ALP, therefore, no or very low detection of ALP could be observed (FIGS. 8A and 8B). The co-culture of differentiated osteoblasts with PBMCs was performed as described above with MSCs. As shown in FIGS. 8C and 8D both the untreated and IL-2 treated PBMCs triggered significant increase in ALP staining in osteoblasts. IL-2 treated PBMCs triggered much higher levels of ALP staining when compared to untreated PBMCs (FIGS. 8C and 8D). The levels of ALP staining in osteoblasts were substantially lower in the absence of PBMCs and no significant ALP staining can be seen in untreated or IL-2 treated PBMCs in the absence of osteoblasts (FIGS. 8C and 8D). These results indicated that stem cells were sensitive to lysis by IL-2 treated PBMCs whereas their differentiated counterparts were more resistant and unlike stem cells they were able to resist death and further upregulate ALP when cultured with IL-2 treated PBMCs. In addition, when the levels of VEGF secretion were determined higher induction of VEGF secretion by MSCs could be observed when compared to osteoblasts (FIG. 8E).

Figure 8F:
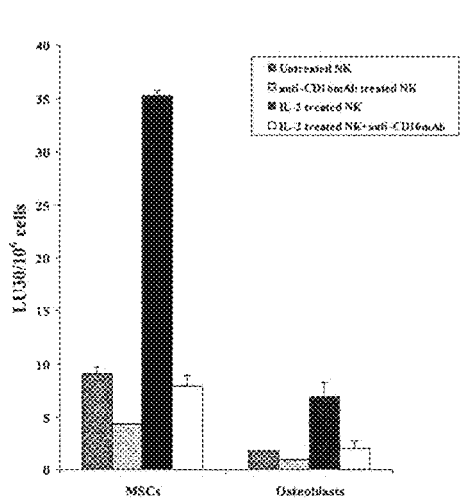
Figure 8G:
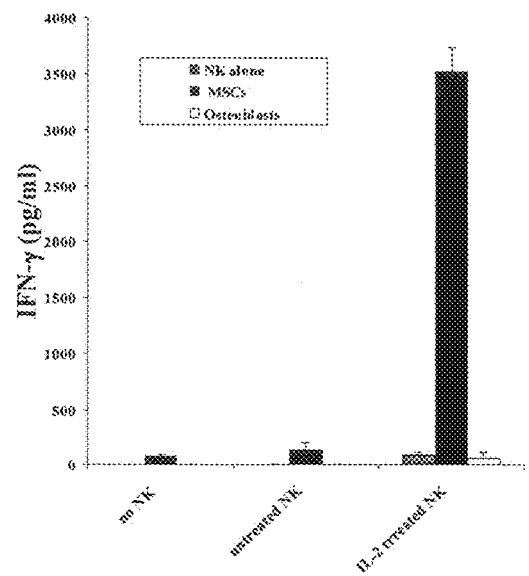
Figure 8H:
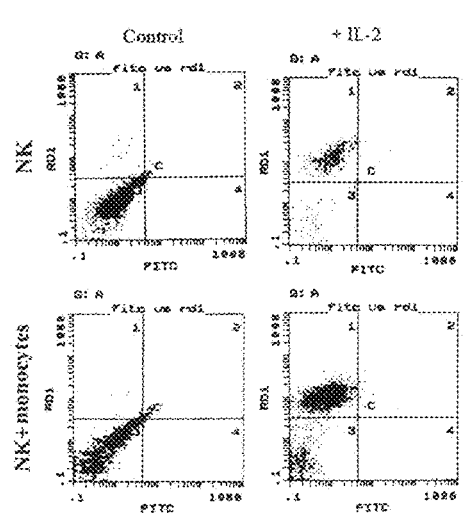
Figure 8I:
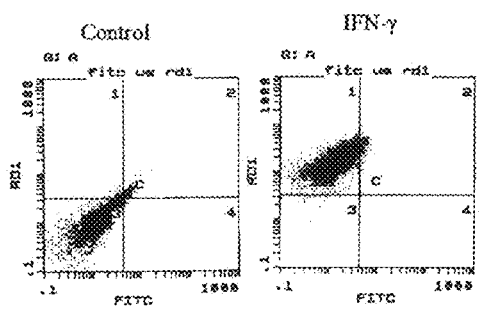

To further demonstrate the resistance of osteoblasts to cell death, MSCs and those differentiated to osteoblasts were also cultured in the absence and presence of different concentrations of HEMA and the levels of cell death were determined after an overnight incubation. Shown in FIG. 8F, HEMA induced significant cell death in undifferentiated MSCs when compared to differentiated osteoblasts. In addition, undifferentiated MSCs were significantly more sensitive to lysis by IL-2 treated NK cells when compared to their differentiated counterparts (FIG. 8G), and triggered significant secretion of IFN-γ in co-cultures with IL-2 treated NK cells (FIG. 8H). Moreover, when MSCs were cultured with NK cells alone or NK cells with monocytes significant induction of B7H1 surface expression could be observed in surviving MSCs (FIG. 8I). We have recently reported that monocytes protect stem cells from NK cell mediated lysis. Accordingly, significantly more surviving MSCs was observed in co-cultures with NK cells and monocytes than with NK cells alone. Monocytes alone were not able to elevate B7H1 expression on the surface of MSCs. The intensity of NK cell induced B7H1 expression on MSCs were similar to that induced by treatment of MSCs with IFN-γ (FIG. 8J). Thus, these results suggested that sensitivity of MSCs to cell death and to NK cell mediated cytotoxicity correlated with the degree of differentiation of these cells. Moreover, NK cells may contribute to differentiation and resistance of MSCs by increased induction of key resistance factors such as B7H1.

Figure 9:
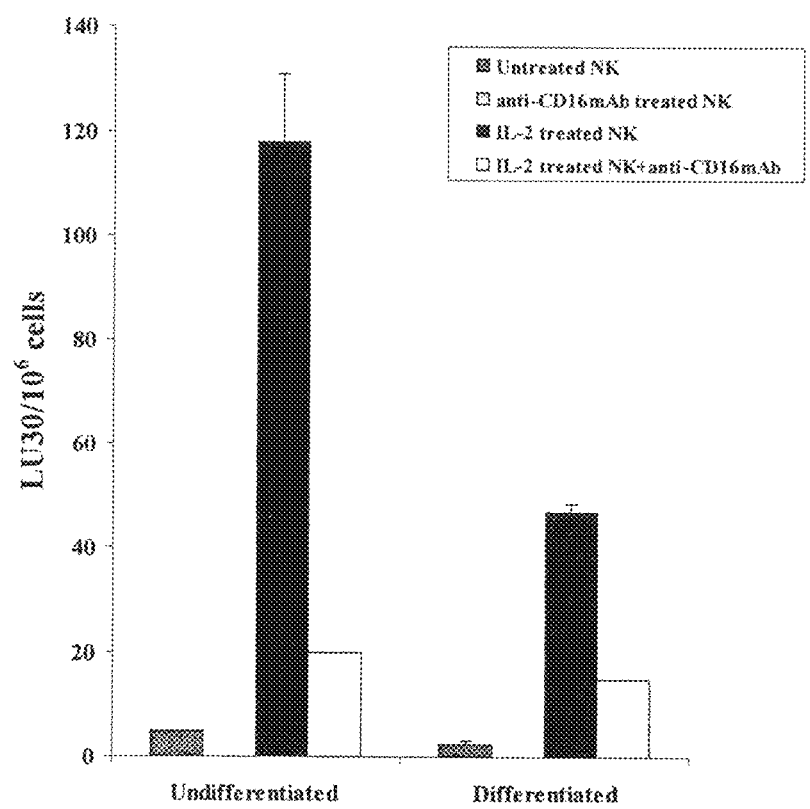
FIG. 9 Undifferentiated DPSCs are significantly more sensitive to lysis by IL-2 treated NK cells than their differentiated counterparts. NK cells ($1 \times 10^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled undifferentiated and differentiated DPSCs and NK cell cytotoxicity was determined using a standard 4 hour $^{51}$Cr release assay. Lytic units $30/10^6$ were determined using inverse number of NK cells required to lyse 30% of the DPSCs×100. Passage 8 differentiated and undifferentiated DPSCs were used.

Differentiated DPSCs are more resistant to NK cell mediated cytotoxicity. DPSCs were differentiated by the addition of β-glycerophosphate, ascorbic acid and dexamethasone as reported previously, and NK cell cytotoxicity were determined against both the differentiated and undifferentiated DPSCs. As shown in FIG. 9 significantly less NK cell cytotoxicity could be obtained against differentiated DPSCs by untreated, IL-2 treated and IL-2 plus anti-CD16 mAb treated NK cells when compared to undifferentiated DPSCs. In addition, significantly less NK cell cytotoxicity could be seen against passage 8 when compared to passage 3 undifferentiated DPSCs. Therefore, a stepwise decrease in NK cell cytotoxicity could be observed depending on the stage of the differentiation of DPSCs.

Figure 10:
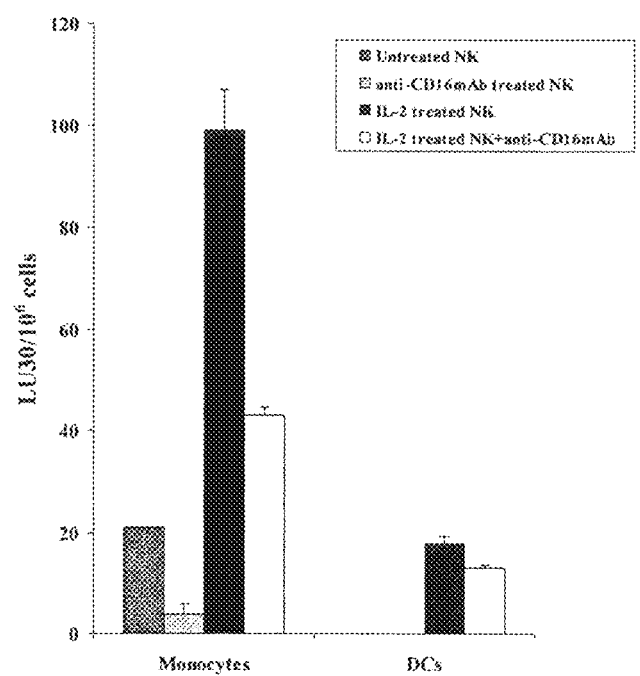
FIG. 10 Monocytes are significantly more sensitive to NK cell mediated cytotoxicity than DCs. NK cells ($1 \times 10^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled autologous monocytes or $^{51}$Cr labeled autologous DCs, and NK cell cytotoxicity were determined using a standard 4 hour $^{51}$Cr release assay and the lytic units $30/10^6$ were determined using inverse number of NK cells required to lyse 30% of the monocytes or DCs×100. One of four representative experiments is shown in this figure.

Decreased sensitivity of dendritic cells to NK cell mediated lysis. To demonstrate that resistance of NK cell mediated cytotoxicity by increased differentiation of stem cells is not restricted to only certain types of cells, we used monocytes and their differentiated counterpart dendritic cells to determine sensitivity to NK cell mediated lysis. We have recently shown that monocytes have exquisite sensitivity to NK cell mediated lysis. As shown in FIG. 10 monocytes were significantly more sensitive to NK cell mediated cytotoxicity than DCs, their differentiated counterparts.

Figure 11:
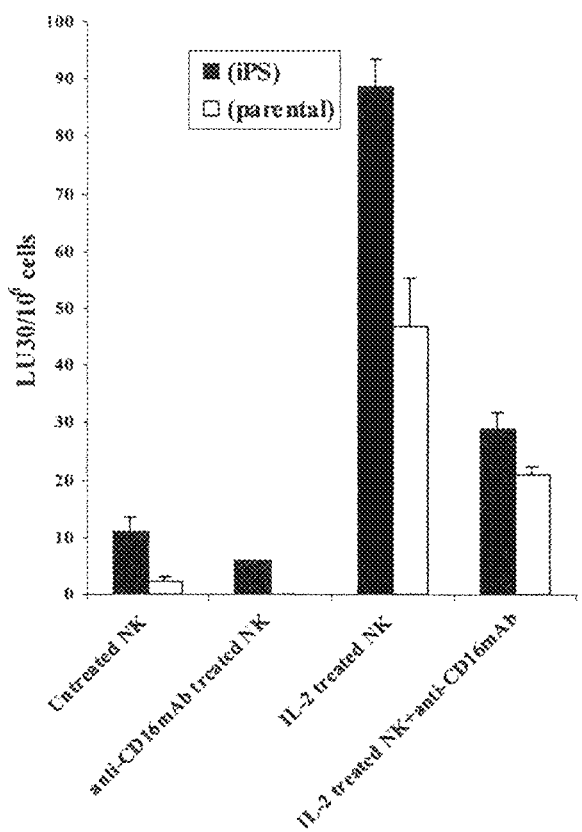
FIG. 11 IPS cells are more susceptible to NK cell mediated cytotoxicity than their parental line. NK cells ($1 \times 10^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled iPS cells or $^{51}$Cr labeled parental cells from which the iPS cells were derived, and NK cell cytotoxicity were determined using a standard 4 hour $^{51}$Cr release assay and the lytic units $30/10^6$ were determined using inverse number of NK cells required to lyse 30% of the iPS or parental cells×100.

IPS cells are more susceptible to NK cell mediated cytotoxicity than their parental line. Since more differentiated cells were less sensitive to NK cell mediated lysis, we aimed at characterizing the sensitivity of iPS cells as well as the parental line from which they were derived to NK cell mediated lysis. As shown in FIG. 11 untreated or IL-2 treated NK cells lysed iPS cells significantly more than the parental line. Treatment of NK cells with anti-CD16 mAb or a combination of IL-2 and anti-CD16 mAb decreased cytotoxicity mediated by the NK cells (FIG. 11). Therefore taken together the results shown thus far suggest that any attempt in reprogramming or de-differentiating the cells may result in increased sensitivity of the cells to NK cell mediated lysis. We, therefore, performed additional experiments using mice which had targeted knock down of COX2 gene in myeloid subsets to determine whether blocking COX2 which is shown to be elevated in many tumors and is important in differentiation of the cells can elevate sensitivity to NK cell mediated lysis.

Figure 12A:
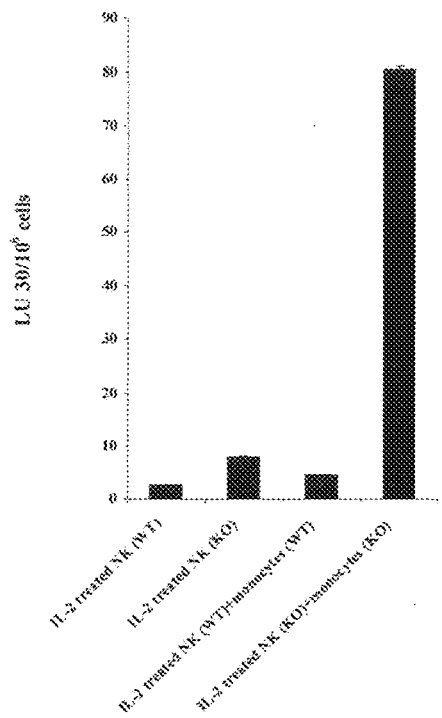
FIGS. 12A-12B Targeted inhibition of COX2 in bone marrow monocytes increased NK cell cytotoxicity and secretion of IFN-γ by IL-2 treated NK cells. Purified NK cells and monocytes were obtained from spleens and bone marrows of 3 pooled control mice and those with targeted knock down of COX2 gene in myeloid cells respectively (n=3). Purified NK cells and monocytes from control mice and those with targeted knock down of COX2 gene in myeloid cells were then cultured with and without IL-2 (1000 u/ml) at 1:1 NK:monocyte ratios for 6 days before they were added to $^{51}$Cr labeled YAC cells, and NK cell cytotoxicity was determined in 4 hours $^{51}$Cr release assay. The lytic units $30/10^6$ were determined using inverse number of NK cells required to lyse 30% of the YAC cells×100 (FIG. 12A). NK cells were cultured as described in FIG. 11A and after 6 days of incubation the supernatants were removed and IFN-γ secretion were measured in the supernatants using a specific ELISA (FIG. 12B). One of five representative experiments is shown in this figure.
Figure 12B:
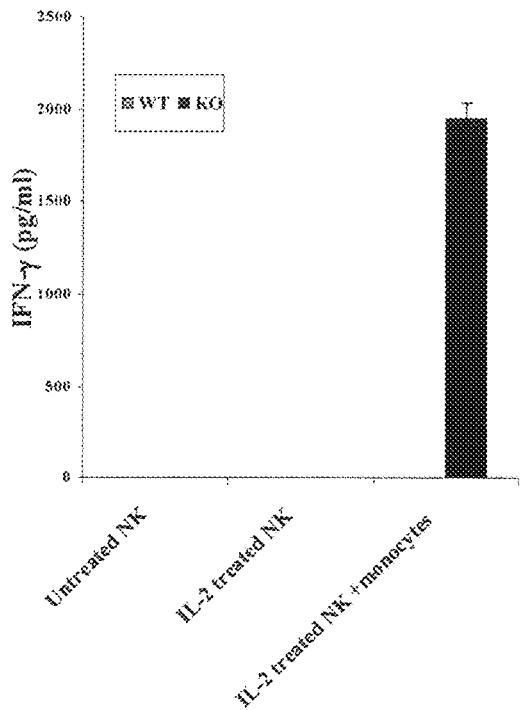

Targeted inhibition of COX2 in bone marrow derived monocytes from LysMCre+/− mice increased cytotoxicity and secretion of IFN-γ by IL-2 treated NK cells. Purified NK cells obtained from spleens of control mice and those with targeted knock down of COX2 gene in myeloid cells were cultured with and without bone marrow derived purified monocytes for 6 days before they were added to $^{51}$Cr YAC cells and cytotoxicity were determined in 4 hours $^{51}$Cr release assay. As shown in FIG. 12A NK cells purified from Cox-2flox/flox LysMCre/+ mice and cultured with autologous COX2−/− monocytes lysed YAC cells significantly more, whereas NK cells from control mice (Cox-2flox/flox LysM+/+) cultured with autologous COX2+/+ monocytes had very little cytotoxicity. Similarly, NK cells purified from Cox-2flox/flox LysMCre/+ mice and cultured with autologous COX2−/− monocytes secreted higher levels of IFN-γ when compared to NK cells from control mice (Cox-2flox/flox LysM+/+) cultured with autologous COX2+/+ monocytes (FIG. 12B).

We have characterized the interaction of a number of oral tumors and a transformed but non-tumorigenic oral keratinocyte line with NK cells and identified several important profiles that could distinguish between differentiated NK resistant oral tumors from undifferentiated NK sensitive tumor stem cells. The results also indicated that the level of NK cell cytotoxicity may vary depending on the expression and function of NFκB in tumors. Thus, increased NFκB appears to be an important factor of differentiation, survival and function of primary oral tumors during their interaction with NK cells.

Increased NK cell cytotoxicity and augmented secretion of IFN-γ were observed when NK cells were co-incubated with UCLA-OSCSCs which released significantly lower levels of GM-CSF, IL-6 and IL-8 and demonstrated decreased expression of phospho-Stat3, B7H1 and EGFR, and much lower constitutive NFκB activity when compared to differentiated UCLA-OSCCs. More importantly, UCLA-OSCSCs expressed oral stem cell marker CD133 and CD44$^{bright}$. Addition of untreated fresh NK cells to UCLA-OSCCs, which were unable to lyse the tumor cells, synergistically contributed to the elevation of the above mentioned cytokines in the co-cultures of NK cells with UCLA-OSCCs. In contrast, untreated NK cells, which lysed UCLA-OSCSCs, were either unable to increase or moderately increased the secretion of resistant factors in the co-cultures of NK cells with UCLA-OSCSCs. Untreated NK cells increased the secretion of VEGF in NK-UCLA-OSCC co-cultures whereas a decrease in VEGF secretion was observed in NK-UCLA-OSCSCs co-cultures when compared to those secreted by the tumors alone. Although the majority of secreted cytokines tested were elevated in UCLA-OSCCs when compared to UCLA-OSCSCs, the levels of VEGF secretion were higher in UCLA-OSCSCs when compared to UCLA-OSCCs. This observation is in agreement with the previously published results where decreased expression of VEGF was seen during the progression of head and neck tumors.

Increase in IFN-γ secretion correlated with a decrease in secretion of IL-6 in the co-cultures of NK cells with UCLA-OSCSCs when compared to UCLA-OSCCs. Furthermore, the potent function of IL-2 activated NK cells could also be seen in regards to suppression of VEGF secretion in tumor cells. Therefore, from these results a specific profile for NK resistant oral tumors emerged which demonstrated increased GM-CSF, IL-6 and IL-8 secretion in the context of decreased IFN-γ secretion during their interaction with the NK cells. In contrast, co-cultures of cancer stem cells with NK cells demonstrated increased IFN-γ in the context of lower GM-CSF, IL-6 and IL-8 secretion.

Many aggressive and metastatic tumor cells exhibit constitutively elevated NFκB activity. Similar to HEp2 cells blocking NFκB in UCLA-OSCCs and HOK-16B cells increased IFN-γ secretion and augmented the cytotoxic function of IL-2 activated NK cells against these cells (FIG. 6). Inhibition of NFκB in UCLA-OSCCs and HOK-16B was confirmed by several observations. First, the synergistic induction of ICAM-1 by TNF-α and IFN-γ treatment, which was previously shown to be due to increased function of NFκB, was greatly abrogated when UCLA-OSCCs and HOK-16B cells were transduced with IκB super-repressor. Second, significant decrease in IL-6 secretion could be observed in both cells and in the co-cultures of immune effectors with UCLA-OSCCs and HOK-16B cells transduced with IκB super-repressor. Lastly, decreased binding of NFκB was observed using luciferase reporter assay in NFκB knock down cells. Therefore, the profiles of NFκB knock down cells resembled those of undifferentiated UCLA-OSCSCs cells based on the parameters tested.

It appears that NFκB in primary oral keratinocytes may serve as the master molecular switch between IL-6 and IFN-γ secretion in the co-cultures of NK cells with tumors. IL-6 is secreted constitutively by oral squamous cell carcinomas and it is found to be elevated in oral cancer patients. IL-6 is known to interfere with IFN-γ signaling by the induction of Th2 differentiation via activation of NFAT which subsequently inhibits Th1 polarization. IL-6 is also known to induce Stat3 activation. Since blocking Stat3 function in tumor cells is also known to activate adaptive immunity (Morrison, Park et al. 2003; Wang, Niu et al. 2004) it may be that IL-6 induced Stat3 is in part responsible for the induction of NK cell inactivation and cell death in the co-cultures of NK cells and either HEp2 cells or UCLA-1 or HOK-16B tumors.

Since UCLA-OSCSCs were significantly more susceptible to NK cell mediated cytotoxicity we hypothesized that stem cells in general may also be more susceptible to NK cell mediated cytotoxicity. Indeed, we have recently demonstrated the exquisite sensitivity of mesenchymal stem cells (MSCs) and Dental Pulp Stem Cells (DPSCs) to NK cell mediated cytotoxicity. In addition, we show in this paper that NK cells lyse hESCs and iPS cells significantly. Taken together these results indicated that undifferentiated cells are targets of NK cell cytotoxicity. However, once NK cells lyse a proportion of sensitive targets they lose their cytotoxic function and gain in cytokine secretion capacity (split anergy) which could then support the differentiation of the cells not lysed by the NK cells. Indeed, similar to NK cells cultured with the undifferentiated sensitive tumors and stem cells, the treatment of NK cells with IL-2 and anti-CD16 mAb resulted in the loss of cytotoxicity, gain in IFN-γ secretion and down modulation of CD16 surface receptors. Loss of cytotoxicity and gain in cytokine secretion was also seen when NK cells were cultured with MSCs and DPSCs in the presence of monocytes.

In vivo physiological relevance of above-mentioned observations could be observed in a subpopulation of NK cells in peripheral blood, uterine and liver NK cells which express low or no CD16 receptors, have decreased capacity to mediate cytotoxicity and is capable of secreting significant amounts of cytokines. In addition, 70% of NK cells become CD16 dim or negative immediately after an allogeneic or autologous bone marrow transplantation. Since NK cells lose their cytotoxic function and gain in cytokine secretion phenotype and down modulate CD16 receptors after their interaction with tumor cells or the stem cells, it is tempting to speculate that in vivo identified CD16-NK cells and in vitro tumor induced CD16-NK cells have similar developmental pathways since they have similar if not identical functional properties.

Figure 13:
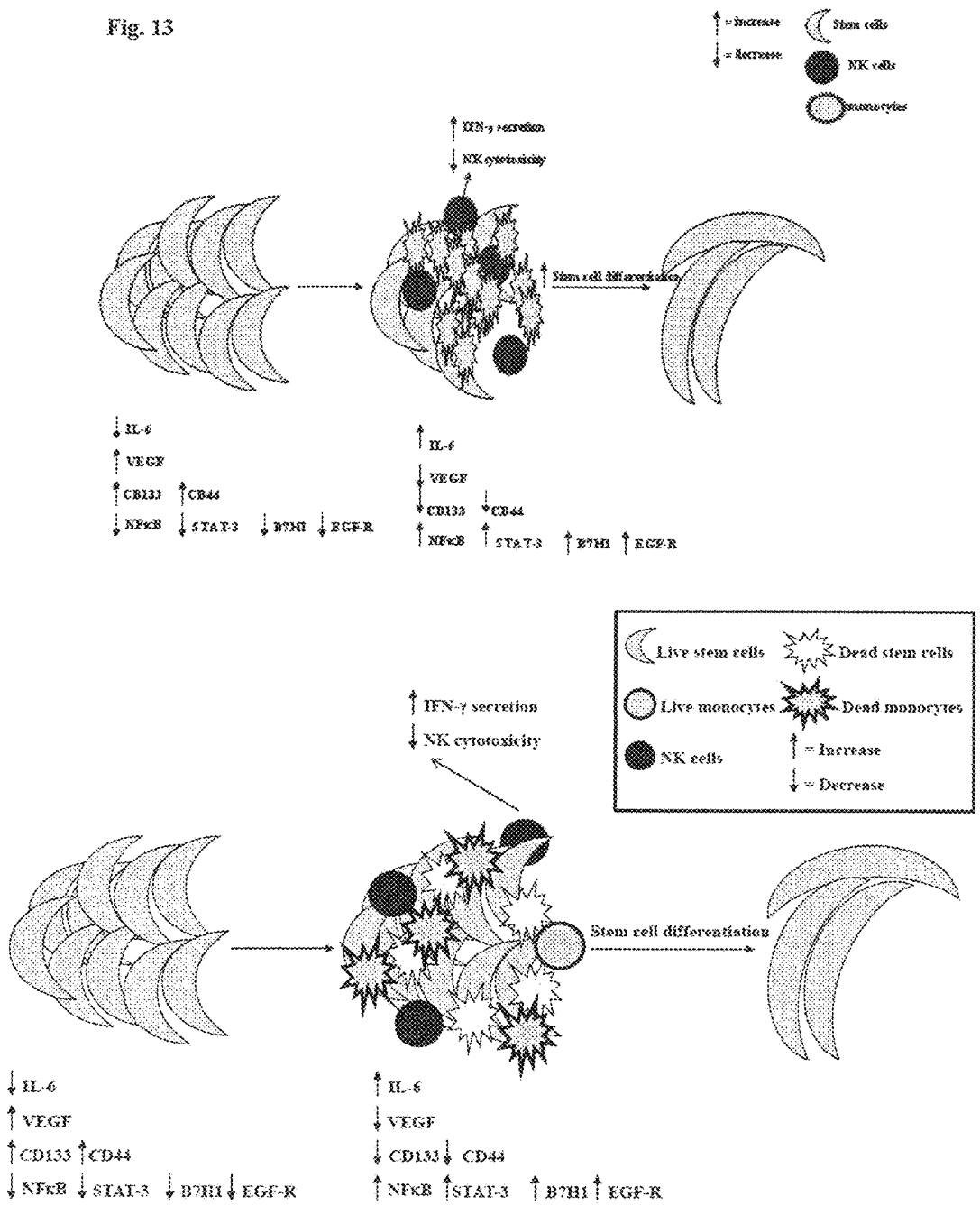
FIG. 13 Schematic representation of hypothetical model of oral cancer stem cell differentiation by NK cells and monocytes. Interaction of cancer stem cells or primary stem cells with monocytes and NK cells results in the loss of NK cell cytotoxicity due partly to the induction of resistance of cancer stem cells by monocytes and indirectly by monocytes serving as targets of NK cells, thus serving as a shield which protects the stem cells from lysis by the NK cells. Loss of NK cell cytotoxicity by monocytes and gain in secretion of IFN-γ results in a significant induction of transcription factors, cytokines and growth factors in stem cells and differentiation of stem cells.

Since undifferentiated cells are targets of NK cells, it is logical that NFκB knock down cells are found to be more susceptible to NK cell mediated cytotoxicity since this process may revert the cells to a relatively less differentiated state and be the cause of activation of NK cells. Indeed, any disturbance in the process of differentiation should provide sensitivity to NK cells since this process is important for modifying the phenotype of NK cells to cytokine secreting cells in order to support differentiation of the remaining competent cells. In this regard knocking COX2 in monocytes may also result in reversion or de-differentiation of the monocytes and the activation of NK cell cytotoxicity. Thus, the degree of differentiation may be predictive of the susceptibility of the cells to NK cell mediated cytotoxicity. In this regard we have also found higher sensitivity of iPS cells to NK cell mediated lysis when compared to parental line from which they were derived. In addition, MSCs not only become resistant to NK cell mediated cytotoxicity after differentiation, but also their level of differentiation increases when they are cultured with the NK cells. As shown here co-culture of NK, monocytes and stem cells are found to result in decreased lysis of stem cells, increased secretion of IFN-γ by the NK cells and elevation in B7H1 surface expression (FIGS. 7D and 7E and). Thus, stem cells which survive should exhibit differentiation markers such as increase in NFκB and STAT3 and augmented secretion of GM-CSF, IL-6 and IL-8 after interaction with NK cells and monocytes (FIG. 13).

Based on the results presented herein, NK cells may have two significant functions: one that relates to the removal of stem cells that are either defective or disturbed or in general more in numbers than are needed for the regeneration of damaged tissue. Therefore, the first task is to select stem cells that are competent and are able to achieve the highest ability to differentiate to required cells. The second important task for NK cells is to support the differentiation of the selected cells after altering their phenotype to cytokine secreting cells. This process will not only remove cells that are either infected or transformed, but also it will ensure the regeneration of damaged or defective tissues. Therefore, processes in which suboptimal differentiation and regeneration of the tissues are achieved, a chronic inflammatory process may be established causing continual tissue damage and recruitment of stem cells and NK cells.

The inability of patient NK cells to kill cancer stem cells due to flooding of NK cells by proliferating cancer stem cells and conversion of NK cells to cytokine secreting cells may be one mechanism by which cancer may progress and metastasize. Therefore, there should be two distinct strategies by the NK cells to eliminate tumors, one that targets stem cells and the other that targets differentiated cells. This can be achieved in oral cancer patients by the use of EGFR antibody since this antibody targets the differentiated oral tumors whereas stem cells should be eliminated by the NK cells. However, since a great majority of patient NK cells have modified their phenotype to support differentiation of the cells, they may not be effective in eliminating the cancer stem cells. Therefore, cancer stem cells may accumulate and eventually result in the demise of the patient. These patients can benefit from repeated allogeneic NK cell transplantation for elimination of cancer stem cells.

TABLE 1

UCLA-OSCSCs similar to HEp2-IkB$_{(S32AS36A)}$ tumor cells secreted no or lower levels of GM-CSF, IL-6 and IL-8.

|  | GM-CSF pg/ml (MFI*) | IL-6 pg/ml (MFI) | IL-8 pg/ml (MFI) |
|---|---|---|---|
| HEp2-vec | 0 ± 0 (30) | 20.6 ± 1 (565) | 685 ± 20 (1390) |
| HEp2-IkB$_{(S32AS36A)}$ | 0 ± 0 (29) | 1.5 ± 0 (67) | 17 ± 0 (453) |
| UCLA-OSCCs | 19.8 ± 2 (79) | 58.4 ± 3 (1554) | 906.3 ± 50 (7583) |
| UCLA-OSCSCs | 0 ± 0 (32) | 0 ± 0 (11) | 245.2 ± 12 (3247) |

HEp2-vec, HEp2-IkB$_{(S32AS36A)}$, UCLA-OSCCs, and UCLA-OSCSCs were cultured at 1 × 10$^5$ cells/ml and the constitutive levels of secreted GM-CSF, IL-6, and IL-8 were determined using multiplex ELISA array kit. The concentrations of secreted cytokines were determined using the standard curve for each cytokine.
*Mean fluorescence intensity (MFI).
One of three representative experiments is shown.

TABLE 2

Increased ratios of IL-6 to IFN-γ secretion in NK resistant UCLA-OSCCs when compared to NK sensitive UCLA-OSCSCs

| Tumor cells | +/−Immune cells | GM-CSF pg/ml | IL-8 pg/ml | VEGF pg/ml | IL-6 pg/ml | IFN-γ pg/ml | Ratio IL-6/IFN-γ |
|---|---|---|---|---|---|---|---|
| UCLA-OSCCs | −NK | 20 | 438.4 | 620.4 | 126 | 0.8 | — |
| UCLA-OSCCs | +NK (−IL-2) | 148.8 | 723.2 | 784 | 215 | 1 | 215 |
| UCLA-OSCCs | +NK (+IL-2) | 565.8 | 282.2 | 145.5 | 179 | 820 | 0.22 |
| UCLA-OSCSCs | −NK | 0.1 | 23.3 | 1745 | 13 | 1 | — |
| UCLA-OSCSCs | +NK (−IL-2) | 25 | 66.7 | 1256 | 65 | 1 | 12.5 |
| UCLA-OSCSCs | +NK (+IL-2) | 1068.9 | 12.5 | 158 | 12 | 1730.6 | 0.007 |
| No tumors | +NK (−IL-2) | 0.8 | 0 | 0.4 | 11 | 0.6 | 18 |
| No tumors | +NK (+IL-2) | 403.2 | 3.14 | 8.6 | 13 | 290 | 0.44 |

NK cells (1 × 10$^6$/ml) were left untreated or treated with IL-2 (1000 units/ml) for 12-24 hours before NK cells (1 × 10$^5$/ml) were added to primary oral tumors at an effector to target ratio of 1:1. Tumor cells were each cultured alone or in combination with NK cells as indicated in the table and the supernatants were removed from the cultures after an overnight incubation. The levels of cytokine secretion were determined using antibody coated multiplex microbead immunoassay. For simplification of the table standard deviations are not included and they ranged from 0% to a maximum of 5% of the amount obtained for each cytokine. One of three representative experiments is shown.

Example 2

Increased NK Cell Cytotoxicity Against UCLA-OSCSCs But Not Those of UCLA-OSCCs

Figure 14:
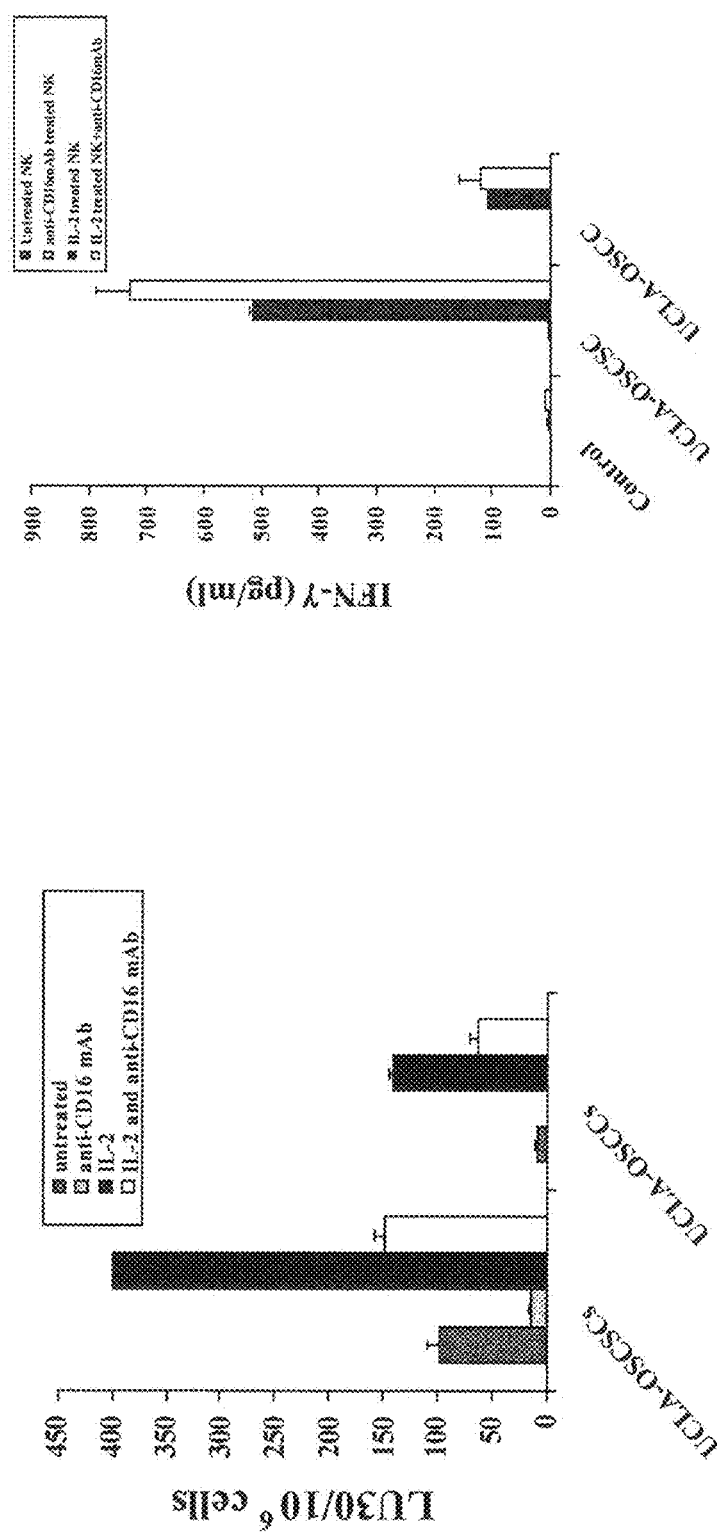
FIG. 14. Treatment of PBMCs or NK cells with anti-CD16 mAb decreased cytotoxicity significantly against both tumor types.

UCLA-OSCC and UCLA-OSCSCs were tested for their sensitivity or resistance to NK cell mediated cytotoxicity. The cytotoxic activities of IL-2 treated PBMCs (FIG. 14A) and NK cells (FIG. 14B) were significantly higher against UCLA-OSCSCs cells when compared to UCLA-OSCCs. Untreated PBMCs or NK cells lysed UCLA-OSCSCs tumors significantly more than UCLA-OSCCs (FIG. 14B). However, the levels of lysis by untreated NK cells were considerably lower than that obtained by IL-2 treated PBMCs or NK cells (FIGS. 14A and 14B). Treatment of PBMCs or NK cells with anti-CD16 mAb decreased cytotoxicity significantly against both tumor types, however, the levels of lysis by the NK cells remained higher against UCLA-OSCSCs in all the NK samples tested (FIG. 14). IL-2 treated NK cells co-cultured with UCLA-OSCSCs oral tumor cells exhibited higher expression of CD69 activation antigen when compared to those co-cultured with UCLA-OSCC oral tumors.

Figure 15:
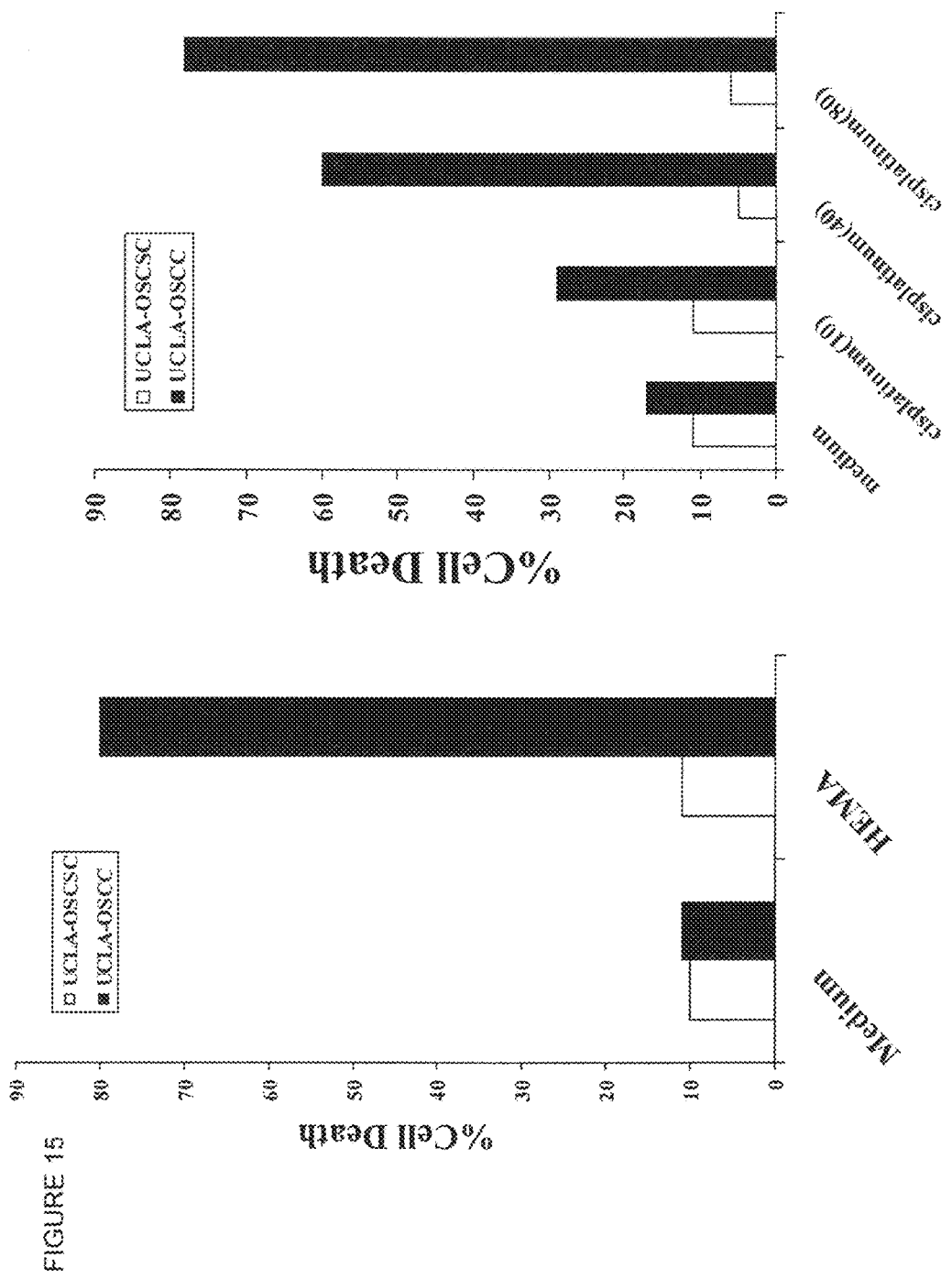
FIG. 15. Resistance of Cancer stem cells to HEMA and cisplatinum mediated cell death.

OSCSCs and OSCCs were treated with HEMA (1:600) and the chemotherapeutic drug cisplatinum at 10 μg/ml, 40 μg/ml and 80 μg/ml. After an overnight incubation the levels of cell death in each tumor type was determined using propidium iodide staining. As shown in FIG. 15 both HEMA and cisplatinum lysed OSCCs significantly; however, OSCSC were significantly more resistant to toxicity mediated by these drugs.

Figure 16:
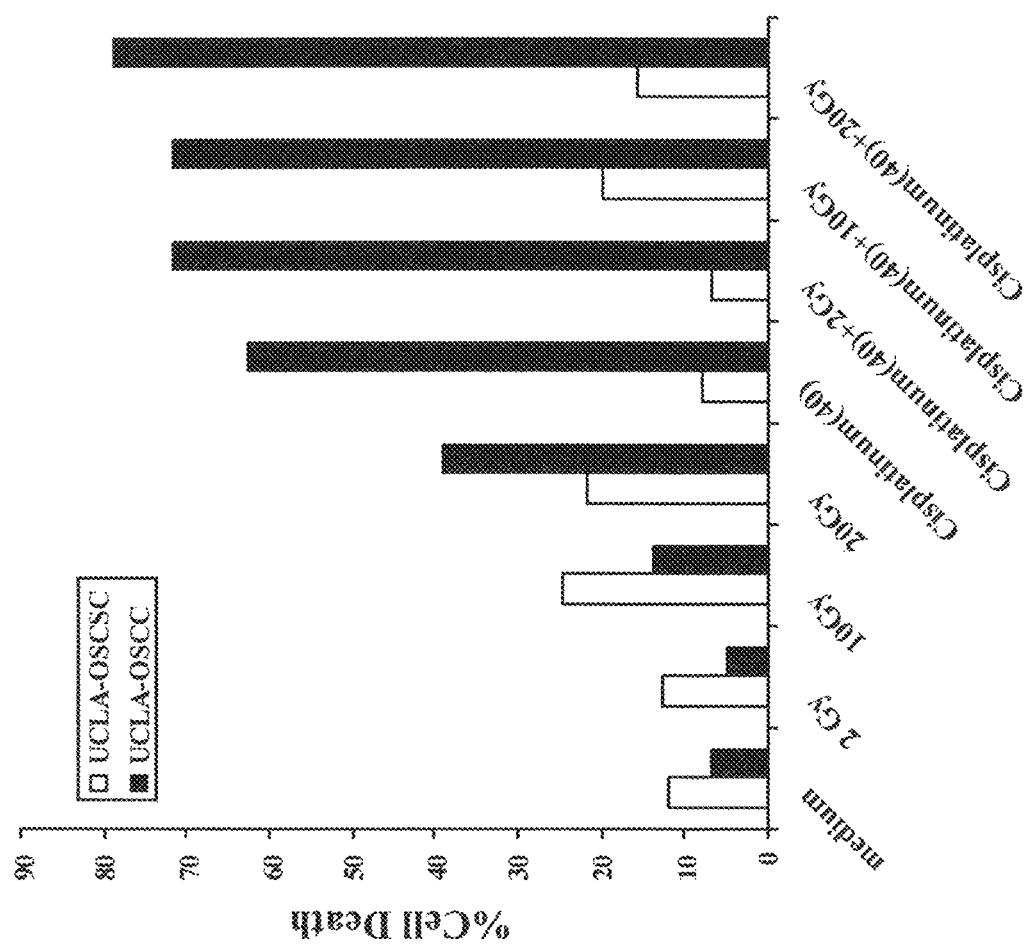
FIG. 16. Resistance of Cancer stem cells to radiation and cisplatinum treatment.

OSCSCs and OSCCs were irradiated at 2 Gy, 10 Gy and 20 Gy and left untreated or treated with chemotherapeutic drug cisplatinum at 40 μg/ml. After an overnight incubation the levels of cell death in each tumor type was determined using propidium iodide staining. As shown in FIG. 16 both radiation and cisplatinum treatment lysed OSCCs significantly; however, OSCSC were significantly more resistant to toxicity mediated by radiation and cisplatinum.

Figure 17:
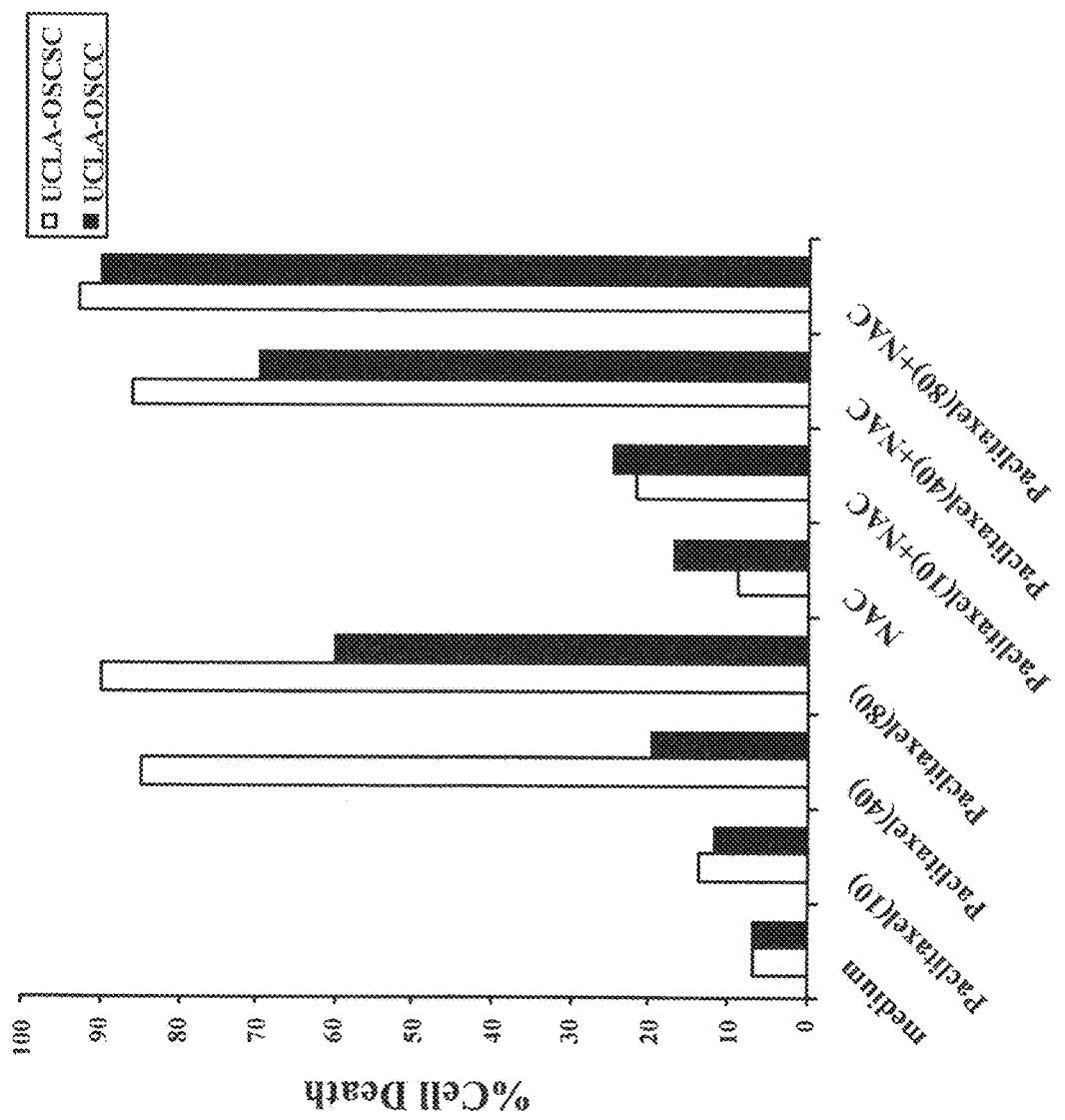
FIG. 17. Lysis of cancer stem cells by the combination of NAC and Paclitaxel and Paclitaxel alone.

OSCSC and OSCCs were treated with Paclitaxel at 10 μg/ml, 40 μg/ml and 80 μg/ml in the presence and absence of NAC (20 mM) and after an overnight incubation the levels of cell death were determined using propidium iodide staining. As shown in FIG. 17 paclitaxel lysed both cell types. In addition, NAC synergized with paclitaxel to lyse cancer stem cells. Therefore, to eliminate cancer stem cells two potential treatments will be effective. 1—using NK cells as an immunotherapeutic strategy and 2—the use of Paclitaxel in combination with NAC.

Example 3

Significant Lysis of Embryonic Stem Cells (hESCs), Induced Pluripotent Stem Cells (iPS), Dental Pulp Stem Cells (DPSCs), and Mesenchymal Stem Cells (MSCs) by Untreated or IL-2 Treated NK Cells Highly purified human NK cells were cultured with and without IL-2 for 12-24 hours before they were added to $^{51}$Cr labeled hESCs (FIG. 18A), iPSCs (FIG. 18B), DPSCs (FIG.

18C) and MSCs (FIG. 18D). Addition of untreated NK cells had lower cytotoxicity against different populations of stem cells whereas activation with IL-2 increased cytotoxicity against all stem cell populations significantly ($p<0.05$). Therefore, human stem cells are greatly lysed by the NK cells.

Lysis of hESCs, iPSCs, DPSCs, and MSCs by untreated and IL-2 treated NK cells is inhibited by anti-CD16 antibody treatment, however, the same treatment induced significant secretion of IFN-γ by the NK cells in the presence and absence of stem cells.

As shown in a number of previous studies anti-CD16 mAb treatment induced anergy in a great majority of the NK cells as well as it induced death in a subset of NK cells, thereby inhibiting NK cell cytotoxicity against different populations of stem cells ($p<0.05$). Addition of the combination of IL-2 and anti-CD16 treatment also induced anergy and NK cell death and inhibited NK cell cytotoxicity against stem cells when compared to IL-2 activated NK cells ($p<0.05$). Untreated or anti-CD16 mAb treated NK cells did not secrete IFN-γ when co-cultured with any of the stem cell populations, however, both IL-2 treated and IL-2 in combination with anti-CD16 mAb treated NK cells in the presence and absence of stem cells secreted significant levels of IFN-γ ($p<0.05$) (FIGS. 19A-19D). Indeed, stem cells triggered significant secretion of IFN-γ from IL-2 treated NK cells when compared to IL-2 treated NK cells in the absence of stem cells. In addition, there was a synergistic induction of IFN-γ secretion in IL-2 and anti-CD16 mAb treated NK cells in the absence of stem cells, and the levels either remained the same or exceeded those in the absence of stem cells when IL-2 and anti-CD16mAb treated NK cells were cultured with stem cells (FIGS. 19A-19D). There was a direct correlation between secretion of bFGF by stem cells and cytotoxicity by IL-2 and IL-2+anti-CD16 treated NK cells.

Lysis of MSCs by untreated and IL-2 treated NK cells is inhibited by monocytes, however, the addition of monocytes induced significant secretion of IFN-γ by the NK cells in the presence and absence of stem cells. Monocytes were purified from PBMCs and irradiated as indicated in the Material and Methods section. MSCs were co-cultured with irradiated monocytes for 24-48 hours before they were labeled with $^{51}$Cr and used in the cytotoxicity assays against NK cells. NK cells were left untreated or pre-treated with anti-CD16 antibody and/or IL-2 for 24-48 hours before they were used in the cytotoxicity assays against MSCs. The addition of monocytes to MSCs significantly protected the MSCs from NK cell mediated cytotoxicity ($p<0.05$). Significant inhibition of NK cell cytotoxicity by monocytes could be observed against untreated and IL-2 treated NK samples ($p<0.05$). Monocytes also increased the levels of alkaline phosphatase staining in MSCs and prevented decrease in alkaline phosphatase expression induced by IL-2 activated NK cells. Untreated or anti-CD16 antibody treated irradiated monocytes did not mediate cytotoxicity against MSCs. Overall, these experiments indicated that monocytes protect MSCs against NK cell mediated lysis.

Figure 20A:
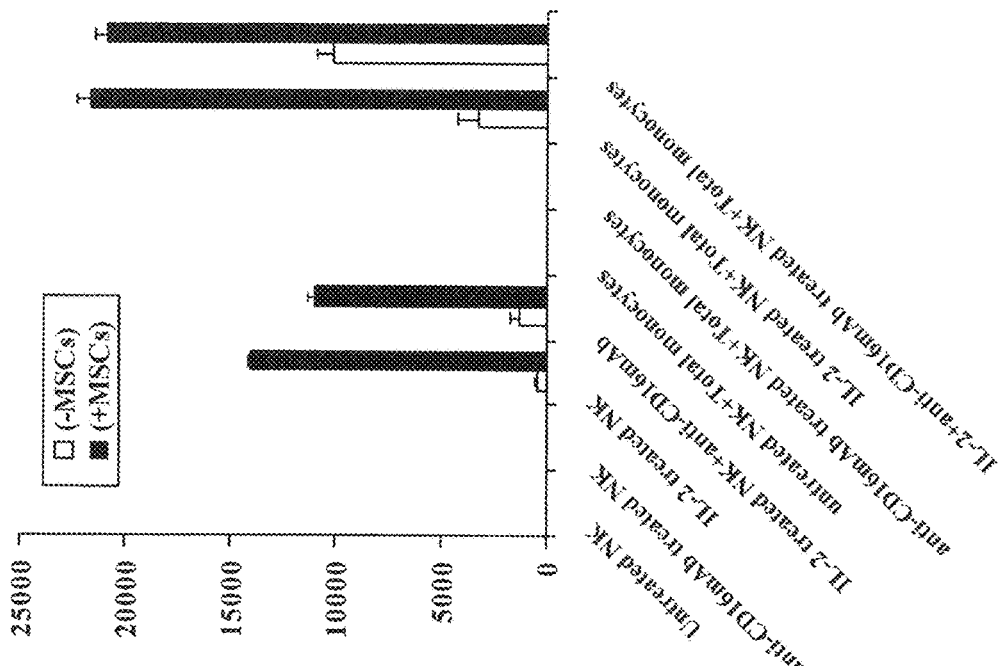
FIGS. 20A-20B. IL-2 treated NK cells secreted moderate amounts of IFN-γ which were synergistically increased when co-cultured in the presence of MSCs.
Figure 20B:
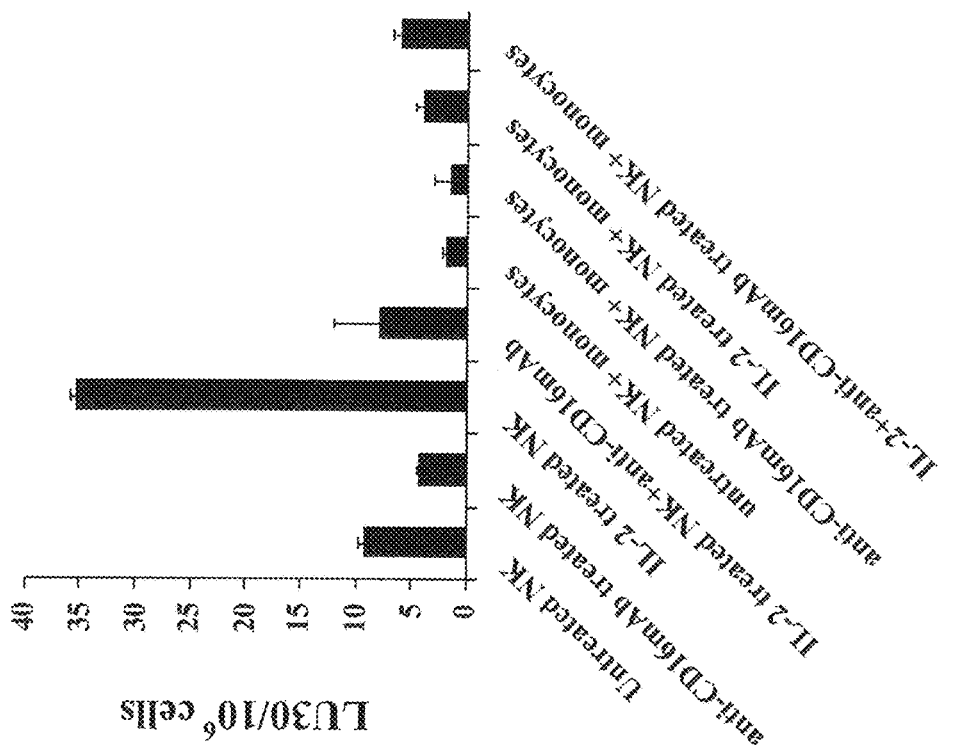

As expected IL-2 treated NK cells secreted moderate amounts of IFN-γ which were synergistically increased when co-cultured in the presence of MSCs ($p<0.05$) (FIGS. 20A-B). The addition of anti-CD16 mAb in combination with IL-2 to NK cells in the absence of MSCs increased secretion of IFN-γ when compared to IL-2 alone treated NK cells in the absence of MSCs. IFN-γ secreted levels remained similar between IL-2 alone and IL-2 and anti-CD16 mAb treated NK cells cultured with MSCs. Monocytes added to IL-2 or IL-2 and anti-CD16 antibody treated NK cells in the absence of MSCs or those in the presence of MSCs, synergistically increased the levels of secreted IFN-γ ($p<0.05$). However, the highest increase in IFN-γ release was seen when monocytes were added to IL-2 or IL-2 and anti-CD16 mAb treated NK cells with MSCs. These results indicated that monocytes increased IFN-γ in co-cultures with MSCs, and further synergized with IL-2 or IL-2 and anti-CD16 mAb treated NK samples to increase the release of IFN-γ in the co-cultures of NKs and MSCs. Similar results were obtained when NK cells were co-cultured with monocytes and DPSCs.

Differentiated DPSCs are more resistant to NK cell mediated cytotoxicity. DPSCs were differentiated to odontoblasts by the addition of b-glycerophosphate, ascorbic acid and dexamethasone as reported previously, and NK cell cytotoxicity were determined against both the differentiated and undifferentiated DPSCs. As shown in FIG. 21, significantly less NK cell cytotoxicity as well as IFN-γ secretion could be obtained against differentiated DPSCs by untreated, IL-2 treated and IL-2 plus anti-CD16 mAb treated NK cells when compared to undifferentiated DPSCs. In addition, significantly less NK cell cytotoxicity could be seen against passage 10 undifferentiated DPSCs when compared to passage 3 undifferentiated DPSCs. Therefore, a stepwise decrease in NK cell cytotoxicity could be observed depending on the stage of the differentiation of DPSCs.

Figure 22B:
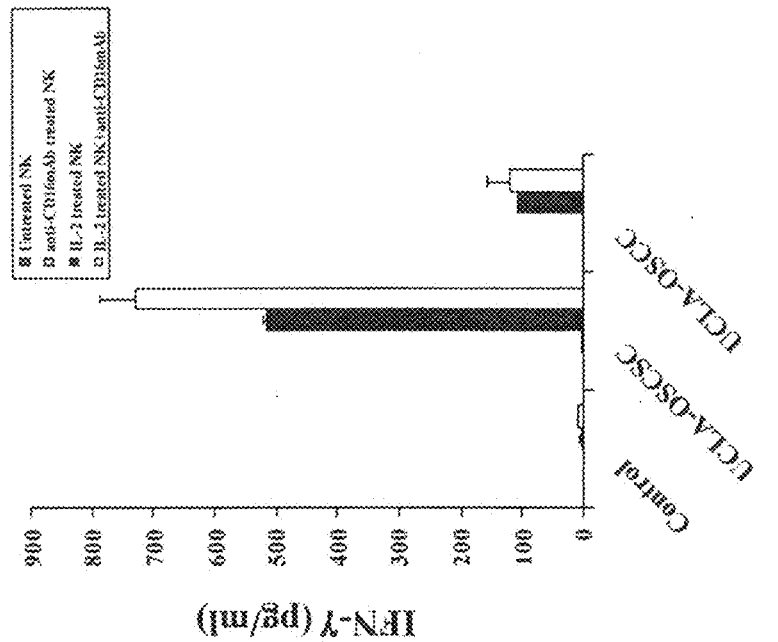
FIGS. 22A-22B. Increased NK cell cytotoxicity against UCLA-OSCSCs but not those of UCLA-OSCCs.
Figure 22A:
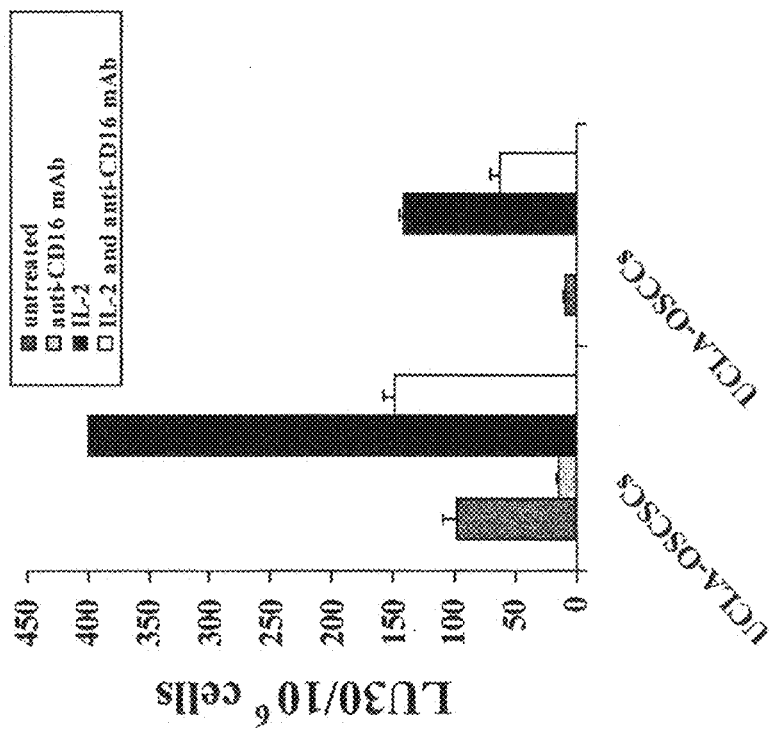

Increased NK cell cytotoxicity against UCLA-OSCSCs but not those of UCLA-OSCCs. UCLA-OSCC and UCLA-OSCSCs were tested for their sensitivity or resistance to NK cell mediated cytotoxicity. The cytotoxic activities of IL-2 treated PBMCs (FIG. 22A) and NK cells (FIG. 22B) were significantly higher against UCLA-OSCSCs cells when compared to UCLA-OSCCs. Untreated PBMCs or NK cells lysed UCLA-OSCSCs tumors significantly more than UCLA-OSCCs. However, the levels of lysis by untreated NK cells were considerably lower than that obtained by IL-2 treated PBMCs or NK cells. Treatment of PBMCs or NK cells with anti-CD16 mAb decreased cytotoxicity significantly against both tumor types, however, the levels of lysis by the NK cells remained higher against UCLA-OSCSCs in all the NK samples tested. IL-2 treated NK cells co-cultured with UCLA-OSCSCs oral tumor cells exhibited higher expression of CD69 activation antigen when compared to those co-cultured with UCLA-OSCC oral tumors.

Figure 23A:
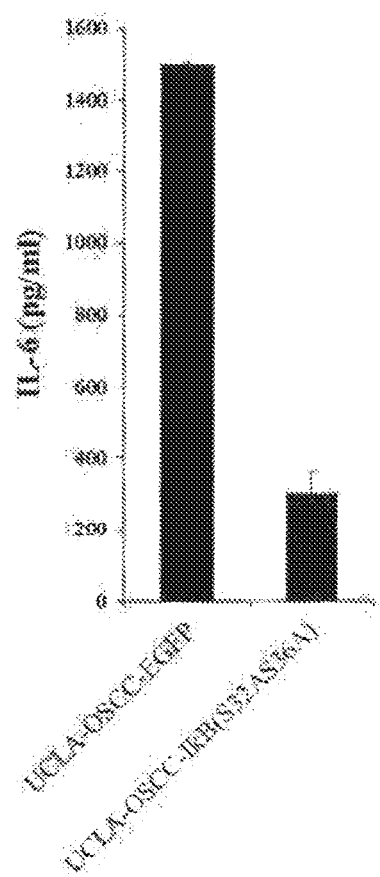
Figure 23B:
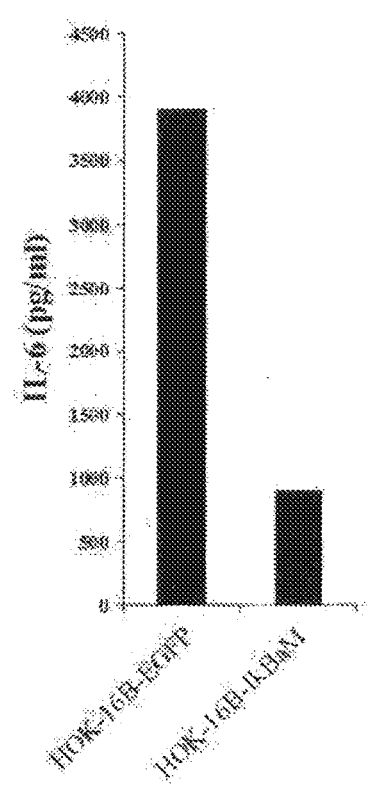
Figure 23C:
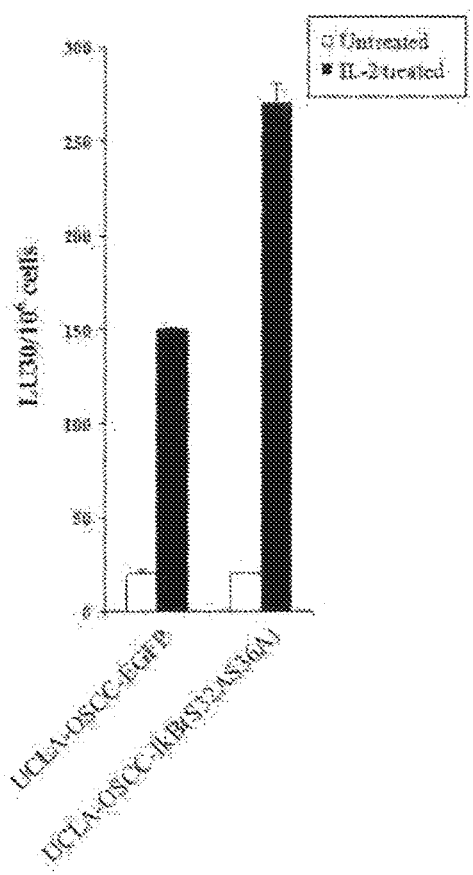
Figure 23D:
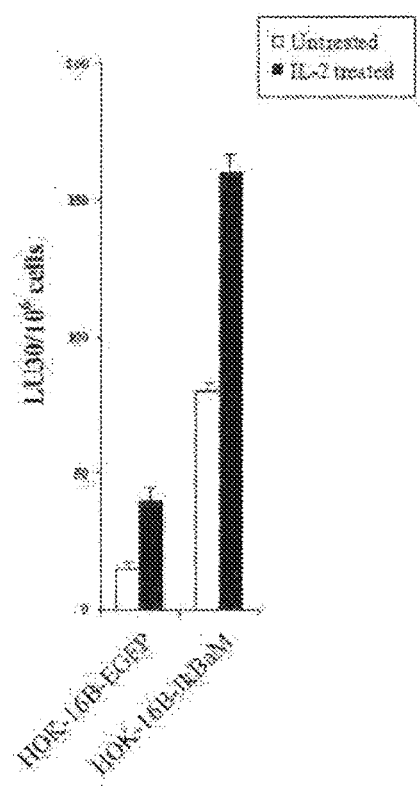

Blocking NFκB in UCLA-OSCCs and HOK-16B oral epithelial cells lowered IL-6 to IFN-γ ratios and increased their sensitivity to NK cell mediated cytotoxicity. Immortalized but non-tumorigenic oral keratinocytes (HOK-16B) or UCLA-OSCCs were transduced with EGFP alone, IκBαM or IκB$_{(S32AS36A)}$super-repressor retroviral vectors and sorted for high GFP expressing cells using flow cytometry. The inhibition of NFκB by the IκBαM or IκB$_{(S32AS36A)}$ super-repressor retroviral vectors in HOK-16B or UCLA-OSCC was confirmed by measuring NFκB activity using luciferase reporter assay (data not shown). IκBαM or IκB$_{(S32AS36A)}$super-repressor transduced HOK-16B (FIG. 23A) or UCLA-OSCC (FIG. 23B) cells secreted substantially lower levels of IL-6 when compared to EGFP transduced cells. NFkB knock down UCLA-OSCCs and HOK-16B cells did not exhibit elevated levels of cell death when assessed by flow cytometric analysis of Annexin V and PI stained cells. IL-2 treated NK cells lysed NFkB knock down OSCCs (FIG. 23C) and HOK-16B (FIG. 23D) cells significantly more than EGFP transfected cells. In addition, IL-2 activated NK cells secreted lower levels of IL-6 but higher amounts of IFN-γ in supernatants obtained from the co-cultures of NK cells with NFkB knock down UCLA-OSCCs (FIG. 23E) and HOK-16B (FIG. 23F) cells as compared to EGFP transduced cells. Similar NK cell response patterns were obtained when NFκB was inhibited in HEp2 cells.

Figure 24B:
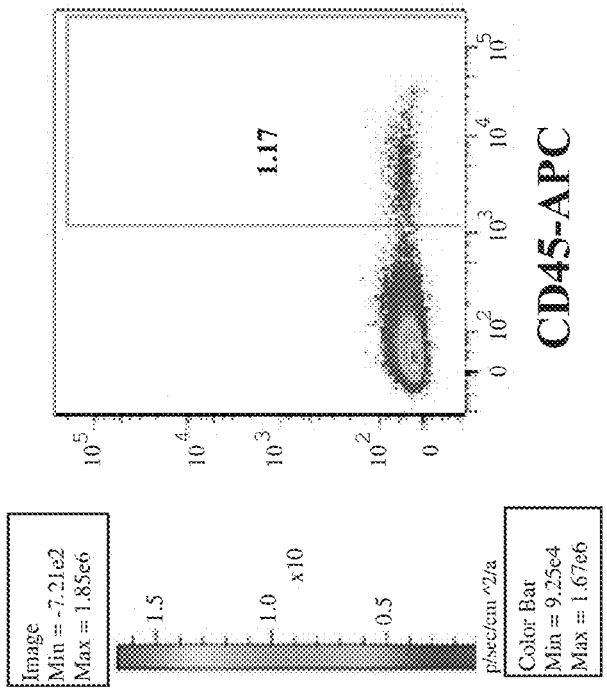
FIGS. 24A-24B. Bioluminescent tracking of engrafted HESC in RAG2-/-gc-/- Mice.
Figure 24A:
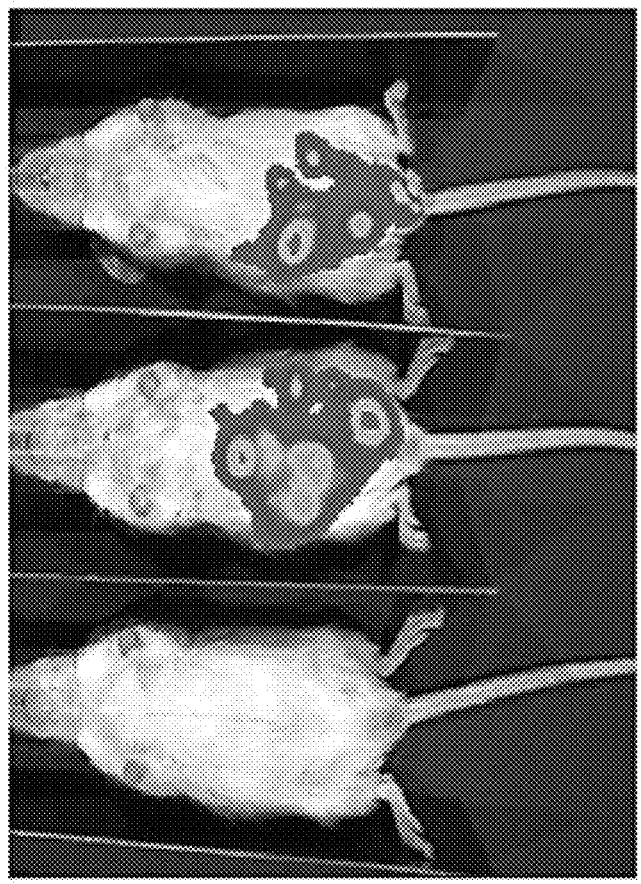

Bioluminescent tracking of engrafted HESC in RAG2$^{-/-}$ γc$^{-/-}$ Mice. Human ES cells (HESC; Hues9) transduced with lentiviral luciferase GFP for 24 hours were transplanted intrahepatically into neonatal RAG2-/-γc-/- mice followed by imaging (IVIS 200) at 4, 6 and 8 weeks (FIG. 24A). Mice were also monitored for teratoma formation. Human CD34+ CD38- cells (50,000 per mouse) from a patient with poor risk AML were transplanted intrahepatically into neonatal RAG2-/-γc-/- mice leading to FACS detectable human CD45 (X-axis) engraftment within 8 weeks of transplantation (FIG. 24B).

Example 4

Figure 25:
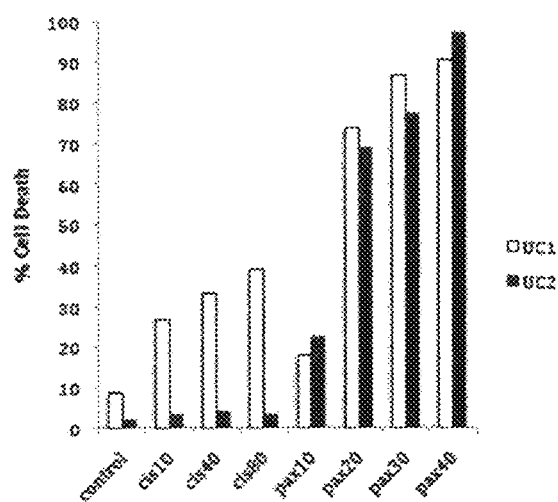
FIG. 25. Dose dependent effect of cisplatin and Paclitaxel on two oral tumors.
Figure 26:
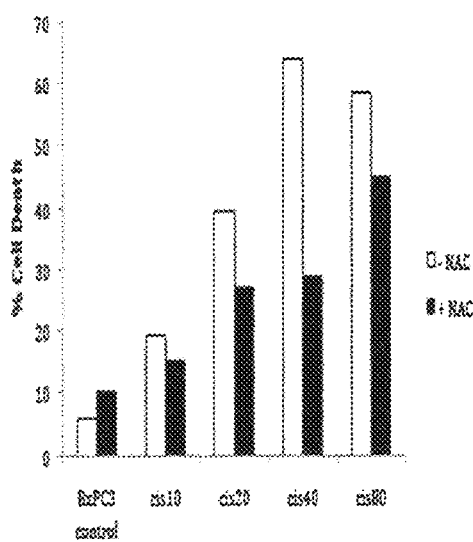
FIG. 26. Dose dependent increase in cisplatin mediated killing of pancreatic cells.

Effect of NK Cells and the Combination of NAC and Paclitaxel on Oral, Pancreatic, Lung, Prostate and Breast Tumors Dose dependent effect of cisplatin and Paclitaxel on two oral tumors (UC-1 is OSCCs, differentiated oral tumor whereas UC2 is OSCSCs, stem-like oral tumors). Cisplatin has increased effect on differentiated OSCCs whereas it does not kill OSCSCs. Paclitaxel affects both cell types similarly (FIG. 25). Dose dependent increase in cisplatin mediated killing of pancreatic cells (BXPC3). NAC inhibits cisplatin mediated killing of pancreatic cells (BXPC3) (FIG. 26).

Figure 27:
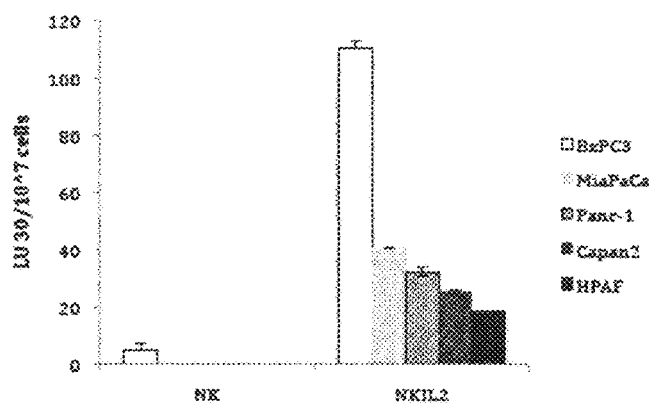
FIG. 27. BxPC3 is less differentiated, and a more stem-like pancreatic tumor line based on surface analysis, and more sensitive to NK cell mediated cytotoxicity.

BxPC3 is less differentiated, and a more stem-like pancreatic tumor line based on surface analysis, and more sensitive to NK cell mediated cytotoxicity as reported previously for oral tumors (Tseng et al, 2010) whereas HPAF is more of a differentiated pancreatic cell type and much more resistant to NK cell mediated cytotoxicity. The two cell types were selected from 5 pancreatic cell lines based on the highest and the lowest sensitivity to NK cell mediated lysis (FIG. 27).

Figure 28A:
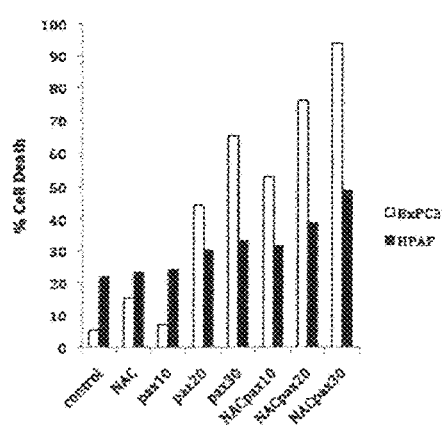
FIGS. 28A-28B. Dose dependent synergistic induction of cell death by NAC and Paclitaxel in BXPC3 pancreatic cells.
Figure 28B:
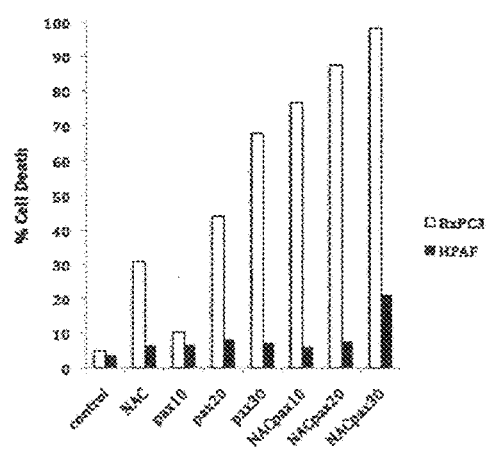
Figure 29:
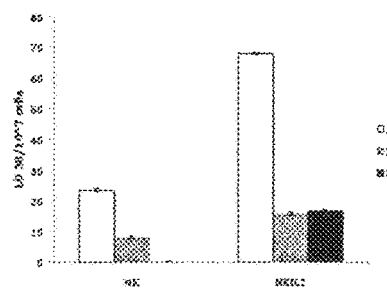
FIG. 29. The cytotoxic function of purified NK cells were assessed against lung tumors (A549), Breast tumors (MCF7) and Prostate tumors (PC3).

Dose dependent synergistic induction of cell death by NAC and Paclitaxel in BXPC3 pancreatic cells, please note HPAF is more resistant to Paclitaxel and NAC mediated cell death than BXPC3 (FIGS. 28A-28B).

Figure 30:
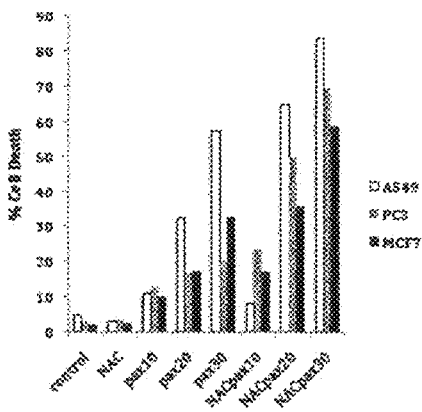
FIG. 30. Dose dependent synergistic effect of NAC and Paclitaxel on lung (A549), prostate (PC3) and breast (MCF7) tumors.

The cytotoxic function of purified NK cells were assessed against lung tumors (A549), Breast tumors (MCF7) and Prostate tumors (PC3). A549 was found to be more sensitive to both untreated and IL-2 treated NK cell mediated cytotoxicity than MCF7 or PC3. Dose dependent synergistic effect of NAC and Paclitaxel on lung (A549), prostate (PC3) and breast (MCF7) tumors (FIG. 30).

Figure 31:
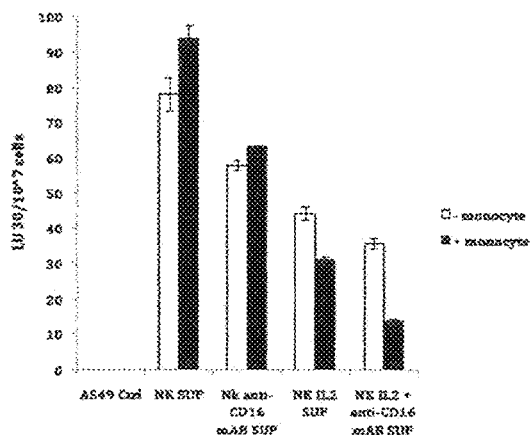
FIG. 31. A549 lung tumors were cultured with supernatants removed from untreated NK, anti-CD16 mAb treated NKs, IL-2 treated NKs and IL2 in combination of anti-CD16mAb treated NK cells in the presence and absence of monocytes.

A549 lung tumors were cultured with supernatants removed from untreated NK, anti-CD16 mAb treated NKs, IL-2 treated NKs and IL2 in combination of anti-CD16mAb treated NK cells in the presence and absence of monocytes. NK treatments were carried out for 24 hours before the supernatants were removed and used to treat A549 lung tumors for 5 days. As shown in the figure treatment of A549 with supernatants from the anergized NK cells (IL-2+ anti-CD16mAb) for 5 days caused the most resistant to NK cell mediated lysis when exposed to IL-2 treated NK cells. Please note the killing of A549 without the NK supernatants are not shown in this figure. Anti-CD16mAb or IL-2 treated NK cell supernatants also caused resistance in A549 cells when compared to A549 treated with supernatants removed from untreated NK cells. Therefore, these results indicated that anergized NK cells are important for the differentiation and resistance of lung tumors. (FIG. 31)

Figure 32:
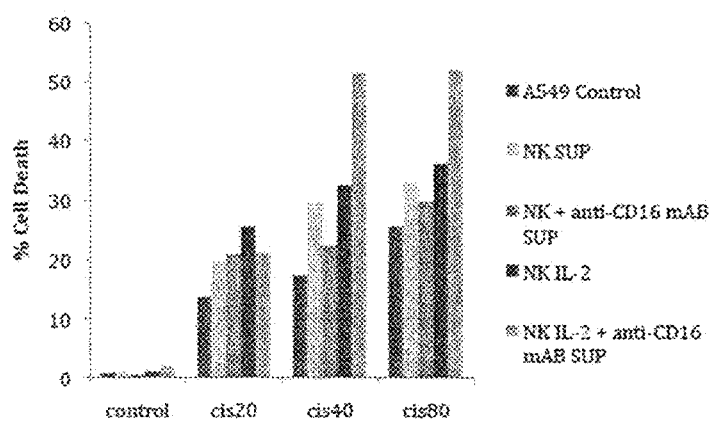
FIG. 32. A549 lung tumors were cultured with supernatants removed from untreated NK, anti-CD16 mAb treated NKs, IL-2 treated NKs and IL2 in combination of anti-CD16mAb treated NK cells in the presence and absence of monocytes.

Similarly, A549 lung tumors were cultured with supernatants removed from untreated NK, anti-CD16 mAb treated NKs, IL-2 treated NKs and IL2 in combination of anti-CD16mAb treated NK cells in the presence and absence of monocytes. NK treatments were carried out for 24 hours before the supernatants were removed and used to treat A549 lung tumors for 5 days. All the NK supernatant treated lung tumors were then washed and treated with different concentrations of Cisplatin as shown in the figure and incubated overnight before they were stained with propidium iodide to determine cell death in each sample. As shown in the figure treatment of A549 with supernatants from the anergized NK cells (IL-2+anti-CD16mAb) for 5 days and then exposed to Cisplatin resulted in the highest induction of cell death by Cisplatin. Untreated NK sup or those treated with anti-CD16mAb or IL-2 treated NK cell supernatants also caused low to moderate increases in cisplatin mediated death of A549 cells when compared to A549 with media alone without NK cell supernatants. Therefore, these results indicated that anergized NK cell supernatant can not only differentiate the lung cells and cause resistance against NK cell mediated cytotoxicity but it can also make the lung tumors more sensitive to chemotherapeutic drugs such as cisplatin mediated cells death. (FIG. 32)

Example 5

Natural Killer Cells Halt Inflammation by Inducing Stem Cell Differentiation, Resistance to NK Cell Cytotoxicity and Prevention of Cytokine and Chemokine Secretion We demonstrate that anergized NK cells induce differentiation of healthy Dental pulp Stem Cells (DPSCs) or transformed Oral Squamous Cancer Stem Cells (OSCSCs) resulting in their resistance to NK cell mediated cytotoxicity and inhibition of the release of inflammatory mediators.

We determined that the stage of maturation and differentiation of the healthy untransformed stem cells, as well as transformed tumorigenic cancer stem cells, is predictive of their sensitivity to NK cell lysis. We further demonstrated that NK cells play a significant role in differentiation of the cells by providing critical signals via secreted cytokines as well as direct cell-cell contact. In addition, we have shown previously that monocytes, a subset of Myeloid Derived Suppressor Cells (MDSCs), induce significant split anergy in NK cells. Such alterations in NK cell effector function aid in driving differentiation of surviving, healthy, as well as transformed stem cells. In cancer patients with advanced disease since the number and function (both the cytotoxic and cytokine secretion) of NK cells may be compromised by the growth and expansion of cancer stem cells, they may not be effective in eliminating and/or differentiating cancer stem cells, thus resulting in the progression of cancer. We demonstrate that anergized NK cells contribute to the differentiation and resistance to NK cell mediated cytotoxicity of transformed stem cells by secreting key cytokines. More importantly, we also demonstrate that NK differentiated stem cells not only resist lysis by the NK cells but also they do not trigger secretion of cytokines or chemokines, potentially contributing to the cessation of inflammation. This will allow the repair of the tissues during normal wound healing whereas during tumorigenesis they may aid in decreasing growth, invasion and metastasis of tumors, while allowing survival of a selected tumor population.

Materials and Methods

Cell Lines, Reagents, and Antibodies. RPMI 1640 supplemented with 10% Fetal Bovine Serum (FBS) (Gemini Bio-Products, CA) was used for the cultures of human NK cells and monocytes. OSCCs and stem-like OSCSCs were isolated from the tongue tumors of the patients at UCLA and cultured in RPMI 1640 supplemented with 10% FBS (Gemini Bio-Products, CA), 1.4% antibiotic antimycotic, 1% sodium pyruvate, 1.4% non-essential amino acids, 1% L-glutamine, 0.2% gentamicin (Gemini Bio-Products, CA) and 0.15% sodium bicarbonate (Fisher Scientific, PA). The primary tumor cells are tested and authenticated regularly in our laboratory. DPSCs from patients were isolated from the third molars after tooth extraction at UCLA and they were cultured in DMEM complete medium supplemented with 2% FBS and 1% penicillin and streptomycin (Gemini Bio-Products, CA) and used with autologous NK cells.

Recombinant IL-2 was obtained from NIH-BRB. Recombinant TNF-α and IFN-γ were obtained from Biolegend (San Diego, Calif.). Antibodies to CD16 were purchased from Biolegend (San Diego, Calif.). Anti-MHC class I were prepared in our laboratory and 1:100 dilution was found to be the optimal concentration to use. PE conjugated anti-CD54 and anti-CD44, were obtained from Biolegend (San Diego, Calif.). Monoclonal antibodies to TNF-α were prepared in our laboratory from ascites of mice injected with TNF-α hybridomas, after which the antibodies were purified and specificity determined by both ELISA and functional assays against recombinant TNF-α. Polyclonal IFN-γ antibodies were prepared in rabbits, purified and specificity determined with ELISA and functional assays against rIFN-γ. 1:100 dilution of anti-TNF-α and anti-IFN-γ antibodies were found to be the optimal concentration to block rTNF-α and rIFN-γ function. The human NK purification kits were obtained from Stem Cell Technologies (Vancouver, Canada). Propidium iodide is purchased from Sigma Aldrich (Buffalo, N.Y.).

Purification of NK cells. PBMCs from healthy donors were isolated as described before. Briefly, peripheral blood lymphocytes were obtained after Ficoll-hypaque centrifugation and purified NK cells were negatively selected by using an NK cell isolation kit (Stem Cell Technologies, Vancouver, Canada). The purity of NK cell population was found to be greater than 90% based on flow cytometric analysis of anti-CD16 antibody stained cells. The levels of contaminating CD3+ T cells remained low, at 2.4%±1%, similar to that obtained by the non-specific staining using isotype control antibody throughout the experimental procedures. Written informed consents approved by UCLA Institutional Review Board (IRB) were obtained from the blood donors and all the procedures were approved by the UCLA-IRB.

ELISA and Multiplex assays: Single ELISAs were performed as described previously. Fluorokine MAP cytokine multiplex kits were purchased from R&D Systems (Minneapolis, Minn.) and the procedures were conducted as suggested by the manufacturer. To analyze and obtain the cytokine and chemokine concentration, a standard curve was generated by either two or three fold dilution of recombinant cytokines provided by the manufacturer. Analysis was performed using the Star Station software.

Surface Staining and cell death assays. Staining was performed by labeling the cells with PE conjugated antibodies or propidium iodide as described previously.

$^{51}$Cr release cytotoxicity assay. The $^{51}$Cr release assay was performed as described previously. Briefly, different numbers of purified NK cells were incubated with $^{51}$Cr-labeled tumor target cells. After a 4 hour incubation period the supernatants were harvested from each sample and counted for released radioactivity using the gamma counter. The percentage specific cytotoxicity was calculated as follows:

$$\% \text{ Cytotoxicity} = \frac{\text{Experimental cpm} - \text{spontaneous cpm}}{\text{Total cpm} - \text{spontaneous cpm}}$$

LU 30/10$^6$ is calculated by using the inverse of the number of effector cells needed to lyse 30% of tumor target cells× 100.

Stem cell differentiation with NK cell supernatant. Human NK cells were purified from healthy donor's PBMCs as described above. NK cells were left untreated or treated with anti-CD16mAb (3 ug/ml), IL-2 (1000 units/ml) or a combination or IL-2 (1000 units/ml) and anti-CD16mAb (3 ug/ml) for 18-24 hours before the supernatants were removed and used in differentiation experiments. The amounts of IFN-γ produced by the activated NK cells were assessed with IFN-γ ELISA (Biolegend, CA). Differentiation of OSCSCs was conducted with gradual daily addition of increasing amounts of NK cell supernatant. On average a total of 1000 pg of IFN-γ containing supernatants obtained from IL-2+anti-CD16mAb treated NK cells was added for 5 days to induce differentiation and resistance of OSCSCs to NK cell mediated cytotoxicity. DPSCs required on average a total of 3600 pg of IFN-γ containing supernatants obtained from IL-2+anti-CD16mAb treated NK cells during a 5 day treatment to promote differentiation and resistance to NK cell mediated cytotoxicity. Afterwards, target cells were rinsed with 1×PBS, detached and used for experiments.

Statistical analysis. An unpaired, two-tailed student t-test was performed for the statistical analysis. One way ANOVA with a Bonferroni post-test was used to compare the different groups.

Results

Resistance of differentiated but not stem-like tumors to NK cell mediated cytotoxicity. To determine whether NK cells target cancer stem cells and not their differentiated counterparts, NK cells were left untreated or treated with anti-CD16 antibody and/or IL-2 for 18-24 hours before they were used in cytotoxicity assays against OSCSCs and OSCCs. As shown previously, NK cells mediated much higher lysis of stem like OSCSCs when compared to differentiated OSCCs (P=0.002). OSCSCs were found to express a number of stem cell markers and they were CD133$^+$CD44$^+$CD326$^+$CD26$^+$CD338$^+$CD166$^{dim}$. Both untreated and IL-2 treated NK cells mediated higher lysis of OSCSCs when compared to OSCCs in $^{51}$Cr release assay (P=0.02), and IL-2 treated NK cells secreted higher levels of IFN-γ in co-culture with OSCSCs when compared to OSCCs (P=0.008). Anti-CD16 mAb treatment inhibited NK cell cytotoxicity against both OSCSCs and OSCCs; however it did not induce any appreciable secretion of IFN-γ. The addition of the combination of IL-2 and anti-CD16 mAb treatment although inhibited NK cell cytotoxicity significantly against OSCSCs and OSCCs when compared to IL-2 activated NK cells alone (P<0.05), it induced much higher release of IFN-γ when cultured in the presence and absence of OSCSCs. The levels of IFN-γ secretion remained much less in the co-cultures of IL-2 and/or anti-CD16 mAb treated NK cells with OSCCs when compared to those cultured with OSCSCs (P<0.05) correlating with the decreased cytotoxicity by IL-2 treated NK cells against OSCCs. Therefore, anti-CD16 mAb in combination with IL-2 induced split anergy in NK cells resulting in a great loss of cytotoxicity but significant gain in secretion of IFN-γ against oral stem-like tumors. Similar results to those obtained with OSCSCs and OSCCs were also obtained with healthy untransformed primary Dental Pulp Stem Cells (DPSCs) and their differentiated counterpart. Noteworthy, IL-2 treated NK cells mediated much higher lysis of undifferentiated DPSCs when compared to differentiated DPSCs and the addition of the combination of IL-2 and anti-CD16 mAb treatment although inhibited NK cell cytotoxicity against undifferentiated and differentiated DPSCs, it induced higher release of IFN-γ.

Figure 33A:
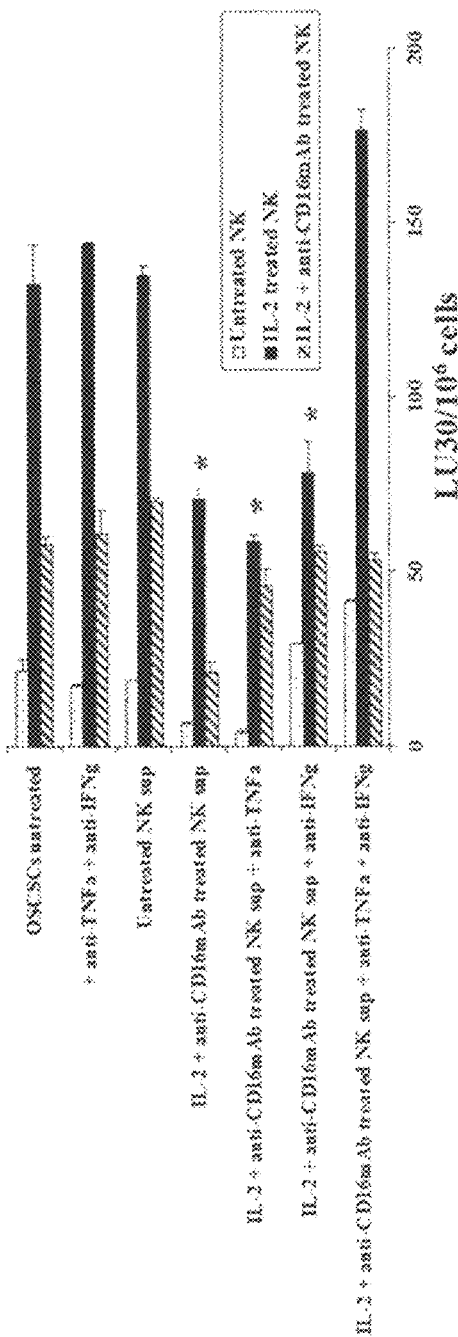
FIGS. 33A-33B Induction of resistance to NK cell mediated lysis of OSCSCs treated with IL-2+anti-CD16mAb NK cells supernatant is mediated by the combination of IFN-γ and TNF-α and not each cytokine alone. Highly purified NK cells were left untreated or treated with the combination of IL-2 (1000 units/ml) and anti-CD16 mAb (3 µg/ml) for 24 hours, after which the supernatants were removed and used for the treatment of OSCSCs. Untreated OSCSCs and those treated with anti-TNF-α (1:100) and anti-IFN-γ (1:100) in the absence of NK supernatants were also used as controls. Same amounts of supernatants from untreated NK cells and those cultured with IL-2+anti-CD16mAb treated NK cells in the presence and absence of anti-TNF-α (1:100) and/or anti-IFN-γ (1:100) were used to treat OSCSCs for a period of 4 days to induce differentiation. Differences between untreated OSCSCs and those stimulated with IL-2+anti-CD16mAb treated NK supernatants with or without the addition of either anti-TNF-α or anti-IFN-γ alone were significant at a p value of <0.05 (*) (FIG. 33A). OSCSCs were treated as described in FIG. 1A for a period of 4 days before they were washed extensively and cultured in medium in the absence of NK supernatants for 2 days. Differences between untreated OSCSCs and those stimulated with IL-2+anti-CD16mAb treated NK supernatants with or without the addition of anti-IFN-γ alone were significant at a p value of <0.05 (*) (FIG. 33B). The cytotoxicity against untreated OSCSCs and those treated with anti-TNF-α and anti-IFN-γ in the absence of NK supernatants, and OSCSCs cultured with either untreated NK supernatants or those cultured with the supernatants from IL-2+anti-CD16mAb treated NK cells in the presence and absence of antibodies to TNF-α and IFN-γ were assessed using untreated, IL-2 treated and the combination of IL-2 and anti-CD16mAb treated freshly isolated NK cells using a standard 4 hour $^{51}$Cr release assay. Percent cytotoxicity was obtained at different effector to target ratio, and the lytic units 30/10$^6$ cells were determined using inverse number of NK cells required to lyse 30% of the tumor cells×100.

Supernatants from the combination of IL-2 and anti-CD16 mAb treated NK cells induced resistance of OSCSCs to NK cell mediated cytotoxicity. To determine whether supernatants from split anergized NK cells are capable of inducing differentiation in OSCSCs, NK cells were left untreated or treated with anti-CD16 antibody and IL-2 for 18-24 hours before their supernatants were removed and added to OSCSCs. In addition, we determined the period of time which was required for the NK differentiated tumors to regain sensitivity to NK cell mediated cytotoxicity after the removal of NK supernatants. Treatment of OSCSCs with IL-2+anti-CD16mAb treated NK cell supernatants, but not untreated NK supernatants, decreased NK cell mediated cytotoxicity significantly by freshly isolated untreated or IL-2 treated NK cells (P=0.02) (FIG. 33A). Resistance of OSCSCs to NK cell mediated cytotoxicity could also be observed after their treatment with supernatants from IL-2 treated NK cells, however, the levels of resistance were significantly less when compared to those induced by IL-2+ anti-CD16mAb treated NK cell supernatants correlating with the degree of differentiation based on the surface receptor expression.

Figure 33B:
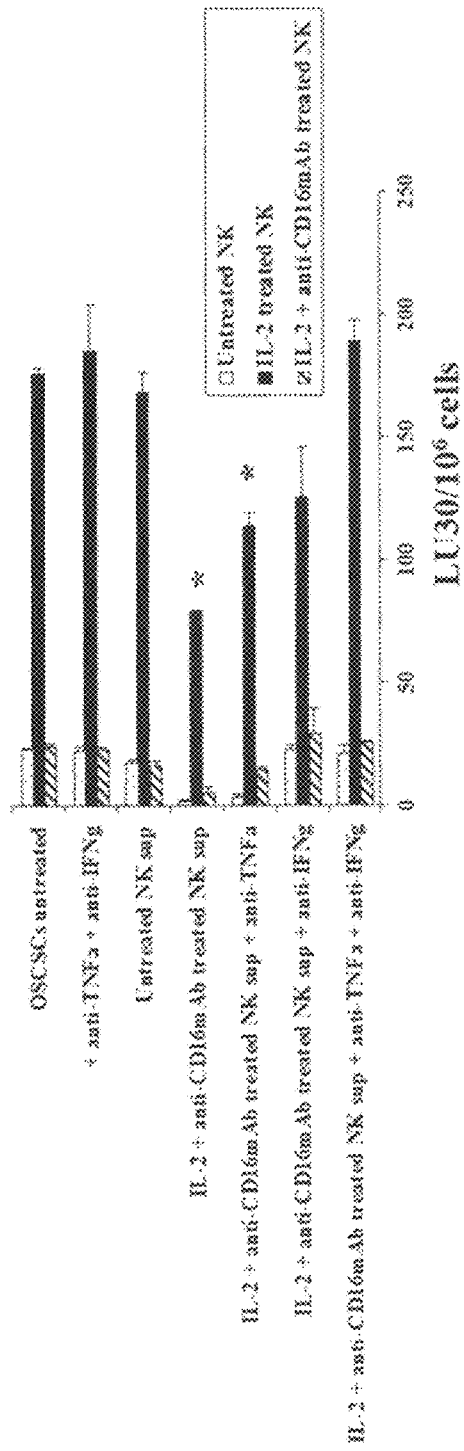

To examine the mechanisms by which OSCSCs become resistant by anergized NK cells, we determined NK cell mediated cytotoxicity when OSCSCs were treated with supernatants of NK cells treated with anti-CD16mAb and IL-2 in the presence and absence of each of IFN-γ and TNF-α antibodies alone or their combination. As shown in FIG. 33A the addition of each of the IFN-γ and TNF-α antibody alone had a slight inhibitory effect on the induction of resistance of OSCSCs, however, the combination of anti-IFN-γ and anti-TNF-α abrogated the resistance of treated OSCSCs completely (FIG. 33A). The inhibition of OSCSCs resistance to NK cell mediated cytotoxicity by the combination of anti-IFN-γ and anti-TNF-α antibodies could be observed when untreated, IL-2 treated or IL-2+anti-CD16mAb treated NK cells (FIG. 33A) were used to assess cytotoxicity. Treatment of OSCSCs with the combination of anti-TNF-α and anti-IFN-γ in the absence of NK supernatants had no effect on NK cell cytotoxicity (FIG. 33A). Similar results to those shown above was also obtained when the supernatants of NK cells were removed from the OSCSCs and they were cultured in media for 2-6 days before they were used in cytotoxicity assay against NK cells. The levels of resistance of OSCSCs to NK cell mediated cytotoxicity were gradually decreased from day 0 to day 2 (FIG. 33B) and to day 6, on day 0 demonstrating the highest resistance, followed by day 2 in which the levels of resistance still remained substantial and by day 6 only 10%-20% resistance could be observed. At day 12 post supernatant removal no differences between IL-2+anti-CD16 mAb supernatant treated OSCSCs and those cultured with supernatants from untreated NK cells. Similar results to those seen with OSCSCs were also observed for DPSCs.

Figure 4A:
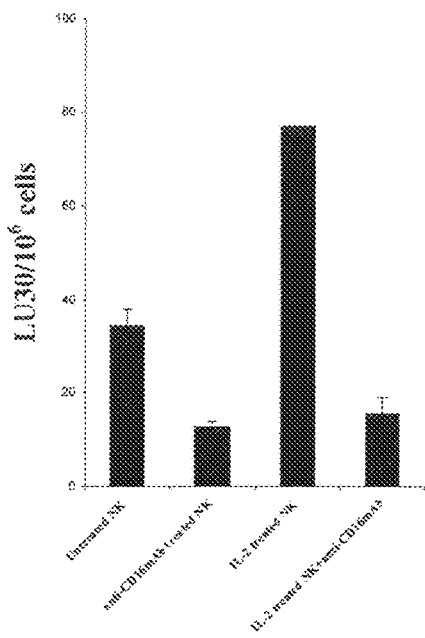
FIGS. 4A-4C Lysis of hESCs by untreated and IL-2 treated NK cells is inhibited by anti-CD16 antibody treatment, however, the same treatment induced significant secretion of IFN-γ by the NK cells. NK cells (1×10$^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled hESCs. NK cell cytotoxicity was determined using a standard 4 hour $^{51}$Cr release assay, and the lytic units 30/10$^6$ were determined using inverse number of NK cells required to lyse 30% of the hESCs×100 (FIG. 4A). NK cells were treated as described in FIG. 4A and each NK sample at (1×10$^5$/ml) were either cultured in the absence of hESCs or added to hESCs at an NK to hESC ratio of 1:1. After an overnight culture, supernatants were removed from the cultures and the levels of IFN-γ (FIG. 4B), and bFGF (FIG. 4C) secretion were determined using specific ELISAs. One of three representative experiments is shown in this figure.
Figure 4B:
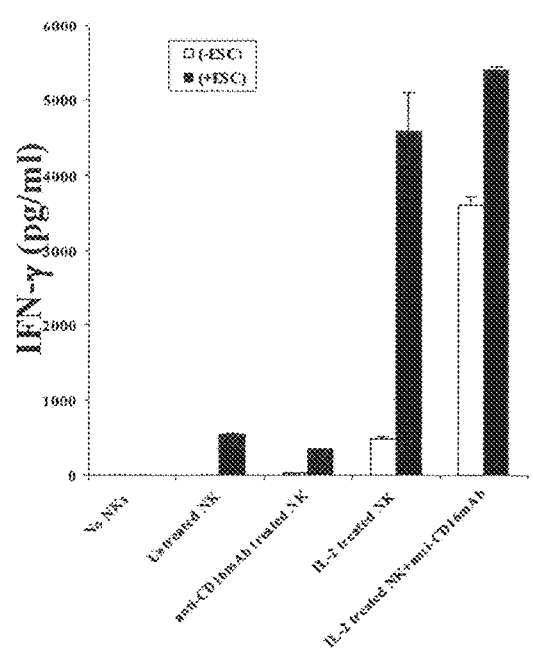
Figure 4C:
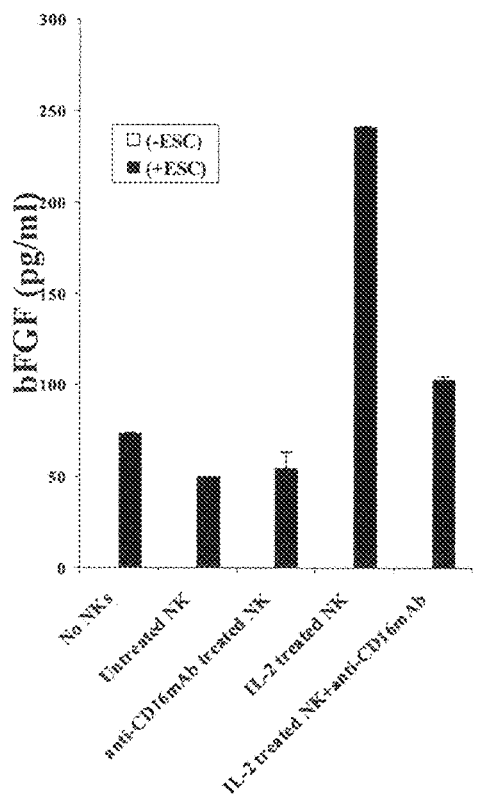
Figure 5A:
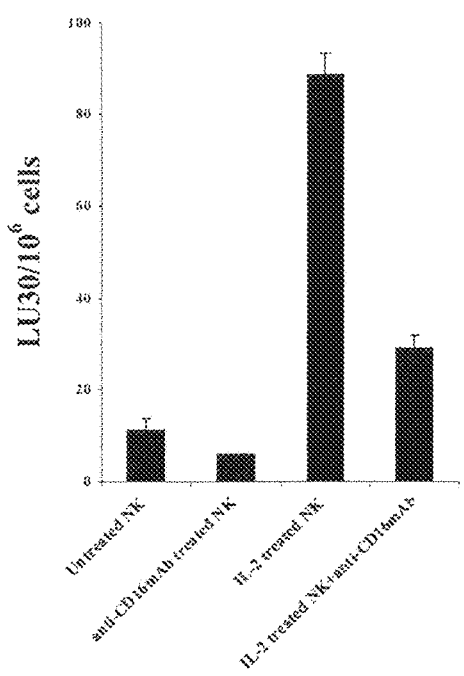
FIGS. 5A-5C Lysis of iPS cells by untreated and IL-2 treated NK cells is inhibited by anti-CD16 antibody treatment, however, the same treatment induced significant secretion of IFN-γ by the NK cells. NK cells (1×10$^6$/ml) were left untreated or treated with IL-2 (1000 units/ml), or anti-CD16 mAb (3 µg/ml) or a combination of IL-2 (1000 units/ml) and anti-CD16mAb (3 µg/ml) for 12-24 hours before they were added to $^{51}$Cr labeled iPS cells and NK cell cytotoxicity was determined using a standard 4 hour $^{51}$Cr release assay, and the lytic units 30/10$^6$ were determined using inverse number of NK cells required to lyse 30% of the iPS cells×100 (FIG. 5A). NK cells were treated as described in FIG. 5A and each NK sample at (1×10$^5$/ml) were either cultured in the absence of iPS cells or added to iPS cells at an NK to iPS ratio of 1:1. After an overnight culture, supernatants were removed from the cultures and the levels of IFN-γ (FIG. 5B), and bFGF (FIG. 5C) secretion were determined using specific ELISAs. One of two representative experiments is shown in this figure.
Figure 5B:
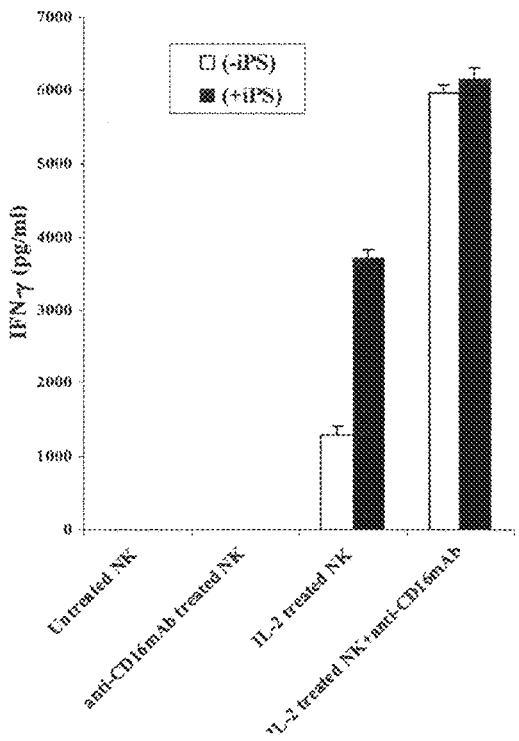
Figure 5C:
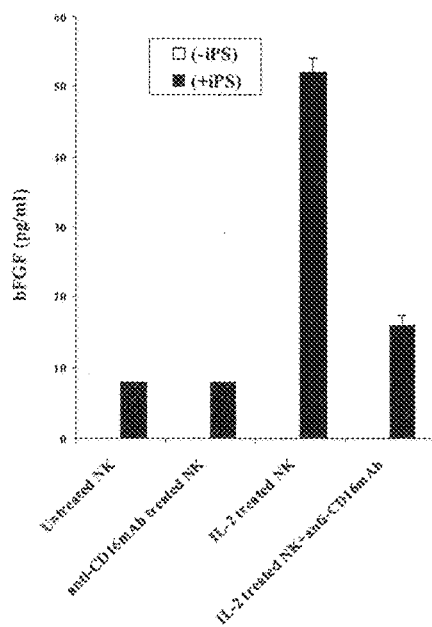

Induction of resistance to NK lysis in OSCSCs by supernatants from IL-2 and anti-CD16mAb treated NK cells correlated with the increased expression of CD54 and MHC class I. We then compared NK cell resistance induced by the supernatants from IL-2+ anti-CD16mAb treated NK cells in OSCSCs to expression of key cell surface receptors before and after removal of NK supernatants. Among many surface receptors tested, B7H1, CD44, CD54 and MHC class I expression were found to correlate significantly with the differentiation and resistance of OSCSCs to NK cell mediated cytotoxicity. However, in this report we focused on only CD54 and MHC class I. As shown in FIG. 34A the levels of CD54 and MHC class I increased substantially on OSCSCs in the presence of IL-2+anti-CD16mAb treated NK cell supernatants. Supernatants from untreated NK cells did not have significant effect on surface expression of OSCSCs (FIG. 34A). The addition of a combination of anti-TNF-α and anti-IFN-γ antibodies at the initiation of OSCSCs treatment with IL-2+anti-CD16mAb treated NK supernatants prevented the up-regulation of CD54 and MHC class I on OSCSCs. The effect of anti-IFN-γ mAb in the absence of anti-TNF-α antibody, however, was more dominant for surface receptor modulation than cytotoxicity or cell growth, since its addition abrogated the increase in CD54 and MHC class I on OSCSCs. Similar results to those shown above were also obtained when the NK supernatants were removed from the OSCSCs on day 0 and they were replaced by media from day 0 to day 6 (FIGS. 34A-4C). The levels of MHC class I and CD54 surface receptors gradually decreased from day 0 to day 2 and to day 6 post removal of NK cell supernatants. At day 12 post NK supernatant removal only 1.5-2 fold increase in MHC class I and 1-1.2 fold increase in CD54 expression could be observed on OSCSCs cultured with supernatants from IL-2+anti-CD16 mAb treated NK cells. Thus, there was a time dependent decrease in the ratios for MHC class I and CD54 surface receptor expression between IL-2+anti-CD16mAb NK supernatant treated OSCSCs versus those cultured with supernatants from untreated NK cells or OSCSCs in the absence of any treatment (FIGS. 34B and 34C). Similar results to those seen with OSCSCs were also observed for DPSCs.

Figures 35A, 35B, 35C:
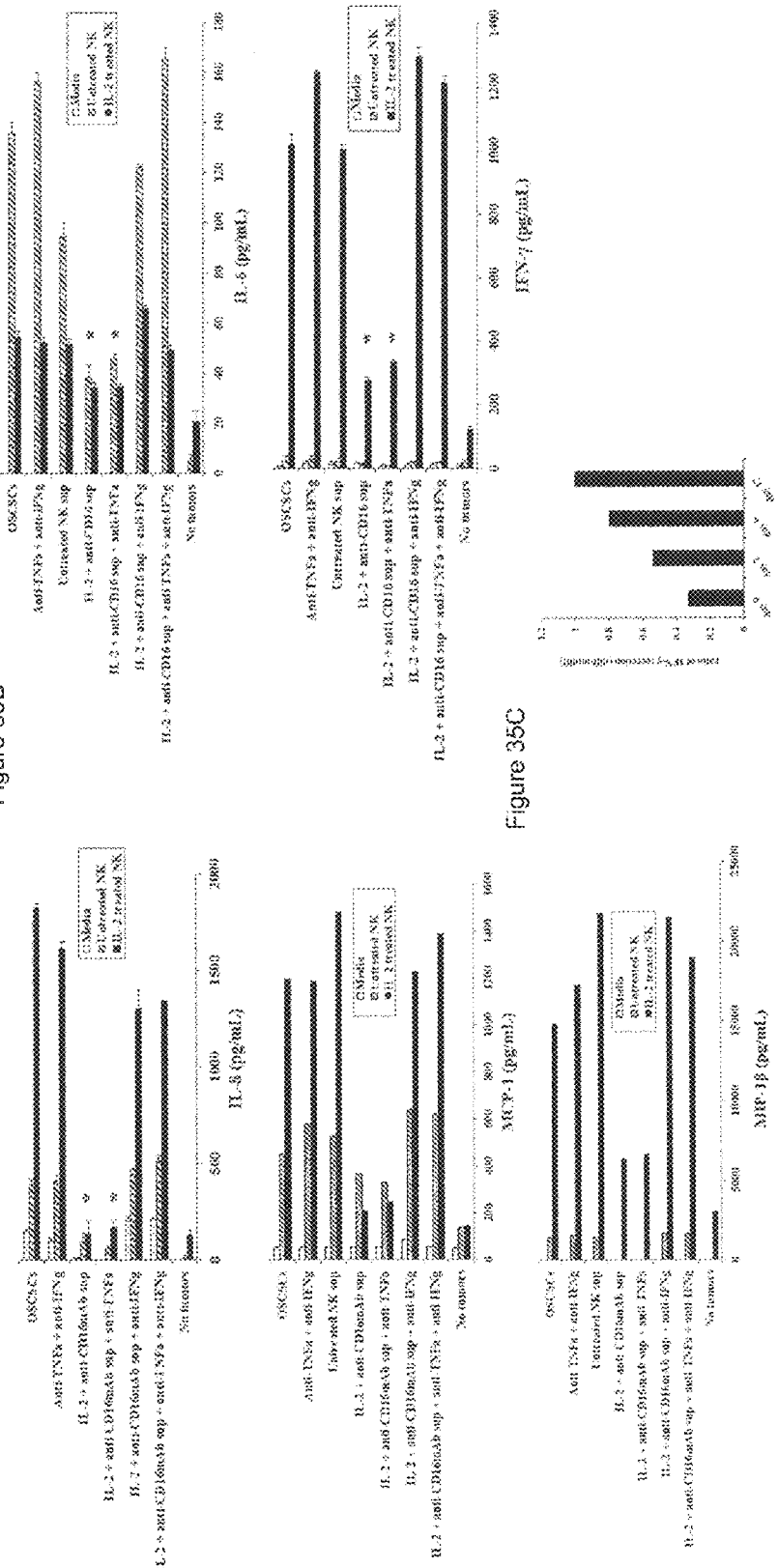
FIGS. 35A-35C OSCSCs cultured with supernatants from IL-2 and anti-CD16mAb treated NK cells significantly inhibited the production of IL-6 and IFN-γ cytokines and IL-8, MCP-1 and MIP-1β chemokines by NK cells. Freshly isolated NK cells were left untreated or treated with IL-2 (1000 units/ml) and/or anti-CD16mAb (3 µg/ml) for 18 hours. Afterwards, NK cells were added to OSCSCs treated with NK cell supernatants as described in FIG. 1A at an effector to target ratio of 0.5 to 1. After an overnight incubation, the supernatants were removed from the co-cultures and the levels of IL-8, MCP-1, MIP-1β chemokines (FIG. 35A), and IL-6 and IFN-γ cytokine (FIG. 35B), secretions were determined using specific ELISAs as well as in a multiplexed format using Luminex technology. Identical results for cytokines and chemokine secretion were obtained using either single or the multiplexed format. Differences between untreated OSCSCs and those stimulated with IL-2+anti-CD16mAb treated OSCSCs with or without the addition of anti-TNF-α were significant at a p value of <0.05 (*). The ratios of IFN-γ production by IL-2 treated NK cells at day 0, 2, 6 and 12 were determined by comparing the amounts of IFN-γ secreted in the co-cultures of NK cells with differentiated OSCSCs with the supernatants from IL-2+anti-CD16 mAb treated NK cells with those secreted in the co-cultures of NK cells with untreated OSCSCs (FIG. 35C).

Treatment of OSCSCs by supernatants from IL-2 and anti-CD16mAb treated NK cells severely inhibited secretion of cytokines and chemokines by the NK cells. We next determined whether decrease in NK cytotoxicity correlates with a decrease in cytokine and chemokine secretion in cultures of OSCSCs treated with supernatants from split anergized NK cells. In addition, we determined the period of time which was required for the NK differentiated tumors to regain sensitivity to NK cells and increase cytokine and chemokine secretion after the removal of NK supernatants. Treatment of OSCSCs with IL-2+anti-CD16mAb treated NK cell supernatants, but not unstimulated NK supernatants, significantly decreased secretion of chemokines IL-8 (p=0.001), MCP-1 and MIP1β (FIG. 35A) and cytokines IL-6 (p=0.01) and IFN-γ (p=0.0009) (FIG. 35B) by freshly isolated untreated and IL-2 treated NK cells. To examine the mechanisms by which NK supernatant treated OSCSCs decrease cytokine secretion by NK cells, we determined secretion in the presence and absence of each of IFN-γ and TNF-α antibodies alone or their combination. As shown in FIG. 35 the addition of TNF-α antibody in the absence of anti-IFN-γ to OSCSCs treated with IL-2+anti-CD16mAb NK supernatants had no or low effect on the increase in secretion of cytokines and chemokine. In contrast, the addition of anti-IFN-γ in the absence of anti-TNF-α increased the levels of IL-8, MCP-1, MIP-1β, IL-6 and IFN-γ in the co-cultures of NK cells with IL-2+anti-CD16mAb treated OSCSCs to the levels when OSCSCs treated with the unstimulated NK supernatants were cultured with NK cells. The increase in the secretion of cytokines and chemokines in the co-cultures of NK cells with IL-2+anti-CD16mAb treated OSCSCs were also observed when they were cultured in the presence of both anti-TNF-α and anti-IFN-γ antibodies. Similar results to those shown above were also obtained when the supernatants of IL-2+anti-CD16mAb treated NK cells were removed from the OSCSCs and were replaced by media from day 0-6. The levels of cytokines gradually rose from day 0-6 and by day 12 no differences could be seen between OSCSCs treated with the supernatants from IL-2+anti-CD16mAb stimulated NK cells and those cultured with untreated OSCSCs (FIG. 35C). As the levels of CD54 and MHC class I gradually decreased from day 0-12, the levels of IFN-γ secretion in the co-cultures of NK cells with IL-2+ anti-CD16mAb NK supernatant differentiated OSCSCs gradually rose to the same levels obtained in the co-cultures of NK cells with OSCSCs cultured with supernatants from untreated NK cells (FIG. 35C). Thus, there was a time dependent decrease in the expression of CD54 and MHC class I which correlated with restoration of cytokine secretion in co-cultures of NK cells with IL-2+anti-CD16mAb NK supernatant differentiated OSCSCs when NK supernatants were removed and replaced with media from day 0-12. Similar results to those seen with OSCSCs were also observed for DPSCs.

Figure 36B:
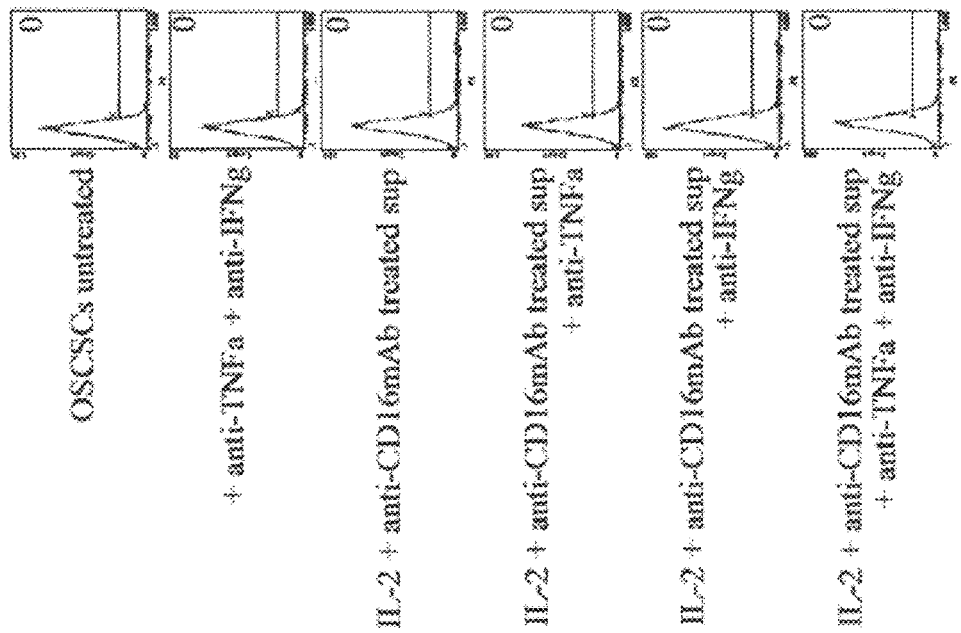
FIGS. 36A-36B Decreased proliferation of OSCSCs after treatment with supernatants from IL-2 and anti-CD16mAb treated NK cells. OSCSCs were treated with supernatants from IL-2 and anti-CD16mAb treated NK cells for 4 days after which treated OSCSCs were washed and cultured in media for an additional 2, 6 and 12 days. The ratios of tumor growth were determined by comparing the number of IL-2+anti-CD16mAb treated NK supernatant differentiated OSCSCs with undifferentiated and untreated OSCSCs at each time point (FIG. 36A). The viability of cells was assessed using propidium iodide staining followed by flow cytometric analysis (FIG. 36B).
Figure 36A:
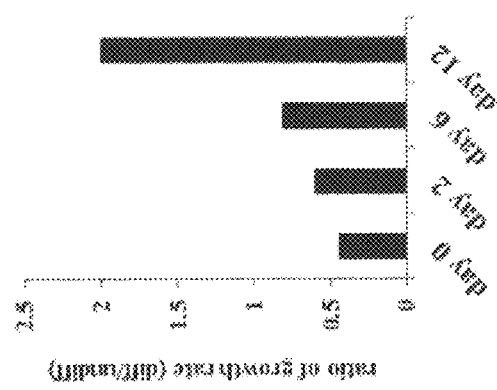

Treatment of OSCSCs by supernatants from IL-2 and anti-CD16mAb treated NK cells inhibited proliferation of OSCSCs. To determine growth dynamics of OSCSCs after treatment with the NK supernatants, the numbers of OSCSCs were counted after treatment with the NK cell supernatants by microscopic evaluation, and the levels of cell death were determined by staining with propidium iodide followed by flow cytometric analysis. As shown in FIG. 36A there was a decrease in the numbers of OSCSCs after their treatment with IL-2 and anti-CD16mAb treated NK cell supernatants when compared to untreated OSCSCs or those cultured with untreated NK cell supernatants. In addition, the decrease in the rate of cell growth was completely inhibited in the presence of the combination of anti-IFN-γ and anti-TNF-α antibodies and not each antibody alone. Interestingly, at day 12 of post supernatant removal the rate of growth in OSCSCs treated with supernatants from IL-2+ anti-CD16mAb treated NK cells increased 2 fold when compared to OSCSCs cultured either with untreated NK cell supernatants or untreated OSCSCs. Moreover, when the viability of OSCSCs were determined after the addition of supernatants from the IL-2+anti-CD16 mAb treated NK cells, no significant cell death in the OSCSCs were seen at day 0 (FIG. 36B) or at days 2-12 after supernatant removal.

We provide evidence that conditioned or anergized NK cells have the ability to induce differentiation of cancer stem cells and limit inflammation through the release of TNF-α and IFN-γ. Similar results to those observed with supernatants were also obtained when fixed IL-2+ anti-CD16mAb treated NK cells were used to differentiate OSCSCs. In addition, monensin treated and fixed NK cells lost the ability to induce resistance and differentiation of OSCSCs. Although supernatants or fixed NK cells treated with IL-2 in the absence of anti-CD16mAb had some effect on resistance of stem cells, the magnitude of resistance was significantly less when compared to those induced by IL2 with anti-CD16mAb treated NK cells.

An important observations is that the differentiation of OSCSCs by anergized NK cells inhibited greatly the secretion of cytokines and chemokines in the cultures of NK cells with differentiated tumors. This observation is of great significance since it indicates that cellular differentiation is an important step in inhibition and prevention of inflammation. Indeed, the levels of cytokines and chemokines secreted in the co-cultures of NK cells with anergized NK supernatant differentiated OSCSCs was in general similar or slightly higher than those secreted by the NK cells in the absence of tumors. Another intriguing observation in our previous studies is inhibition of bFGF in stem cells by anergized NK cells. Since bFGF is important for the maintenance of stemness in a variety of cell types, inhibition of bFGF by anergized NK cells may be one of the mechanisms by which NK cells prevent growth and proliferation of stem cells and promote their differentiation.

There was a gradual and time dependent decrease in the expression of both MHC class I and CD54 which correlated with the increased cell growth and restoration of NK cell cytotoxicity and cytokine secretion in cultures of NK cells with differentiated OSCSCs from days 0-12 post NK supernatant removal. These experiments indicated that for the OSCSCs to remain differentiated, a continuous exposure to cytokines are necessary since after their removal, the cells revert to their undifferentiated phenotype and become sensitive to NK cell mediated cytotoxicity, and trigger the release of cytokines and chemokines. These results may explain the mechanisms underlying chronic auto-immune inflammation in which the patients suffer from bouts of exacerbation and remission. Such plasticity in differentiated tumors may explain the need for continuous presence of immune cells in the tumor microenvironment for the inhibition of tumor invasion and metastasis. Indeed, patients which have tumors with infiltrating immune cells have a better prognosis than those which lack infiltration of immune effectors.

Lack of NK cytotoxic function against differentiated tumors may be due to the release of immunosuppressive cytokines such as TGF-β and IL-10 which regulate cytotoxicity as well as TNF-α and IFN-γ release. Our recent studies indicated that IL-10 is an important regulator which limits NK cell mediated tumor differentiation through inhibition of IFN-γ secretion during monocyte mediated induction of NK anergy.

It is interesting to note that anergized NK differentiated OSCSCs express higher levels of CD54, however, they are not/less susceptible to NK cell mediated cytotoxicity even though the increase in CD54 expression on tumors is shown to increase NK cell mediated cytotoxicity. It is clear from these experiments that CD54 binding and function in cytotoxicity may be limited depending on the differentiation status of the tumors.

OSCSCs do not secrete IL-6, however, the levels of IL-6 secretion are significantly elevated in the cultures of untreated NK but not IL-2 treated NK cells with OSCSCs. This increase could be due to the elevated IL-6 release by the untreated NK cells, or OSCSCs or both. Untreated or IL-2 treated NK cells fail to trigger IL-6 secretion by NK differentiated OSCSCs.

Induction of split anergy in NK cells is an important NK cell conditioning step responsible for the differentiation of cells during pathological processes. In tumors, since the generation and maintenance of cancer stem cells is chronically high, the majority of NK cells including those of the circulating NK cells, may become conditioned to support differentiation of the cells and as such the phenotype of NK cells in tumor microenvironment as well as in the peripheral blood may resemble that of the anergic NK cells. Therefore, our results show two very important functions for the NK cells. One function of NK cells is to limit the number of stem cells and second to support differentiation of the stem cells. In respect to the oral squamous cell carcinomas since the majority of immune effectors are found at the connective tissue area (FIG. 37), NK cells may first encounter and interact with either the other immune effectors or the effectors of connective tissue such as fibroblasts. NK cells may alternatively first encounter the basal epithelial stem cells in which case by eliminating the stem cells, they too can become anergized. By eliminating a subset of stem cells or other immune inflammatory cells or effectors of connective tissue NK cells could then be in a position to support differentiation of remaining cells since they will be conditioned to lose cytotoxicity and induce cytokine and growth factor secretion. In addition, lack of significant infiltration of NK cells in the tumor nest and the localization of NK cells in the immune rich compartment which surrounds the tumor in other tumor types, also provides the means for the induction of split anergy in NK cells primarily by other immune effectors in the tumor microenvironment. Such mechanisms of NK cell conditioning by Myeloid Derived Suppressor Cells (MDSCs) may explain why the cytotoxic function of NK cells are greatly reduced in the tumor microenvironment as well as in circulating NK cells.

There are two strategies to eliminate tumors, one which targets stem cells and the other which targets differentiated cells, which strategies can be usefully combined. Since cancer stem cells are resistant to chemotherapeutic drugs but sensitive to NK cell mediated killing, while differentiated oral tumors are more resistant to NK cell mediated killing but more susceptible to chemotherapeutic drugs, a combination of these two therapies is effective for the elimination of tumors. In addition, since a great majority of patients' NK cells have modified their phenotype to support differentiation of the cells, they may not be effective in eliminating cancer stem cells. Therefore, these patients benefit from repeated allogeneic NK cell transplantation for elimination of cancer stem cells. Depletion of NK anergizing effectors such as MDSCs in the tumor microenvironment before allogeneic NK cell transplantation may also provide such strategy.

The benefit of such a combination approach is the ability of chemotherapeutic drugs to target the differentiated tumors in addition to the lack of differentiated tumors to metastasize. Our recent in vivo data indicated that pancreatic cancer stem cells have the ability to grow faster and metastasize, whereas their differentiated tumors grew slower and remained localized for a long period of time without metastasizing.

Example 6

Osteoclasts as Key Subsets of Immune Effectors Modulating the Function of Natural Killer Cells;

The aim of this study is to establish osteoclasts as key immune effectors capable of modulating the function of Natural Killer (NK) cells and to determine the effect of nitrogen-containing bisphosphonates Zometa and Alendronate and non-nitrogen containing Etidronate in maintaining a pro-inflammatory microenvironment during interaction with NK cells. Bisphosphonates, particularly those of Zolendronic acid and Alendronate trigger significant levels of pro-inflammatory cytokines and chemokines from osteoclasts, and the levels synergistically rises when cultured with NK cells. Nitrogen containing bisphosphonates mediate significant dose dependent release of pro-inflammatory cytokines IL-6, TNF-α, and IL-1β whereas they inhibit the anti-inflammatory IL-10 secretion by osteoclasts. The profiles of 27 cytokines, chemokines and growth factors released from osteoclasts were significantly different from Dendritic (DC) cells and M1 macrophages but resembled those of untreated monocytes and M2 macrophages. The surface expression of CD14, CD33, CD54, CD44, CD11b, MHC class I and II and B7H1 were significantly increased when osteoclasts were treated with Bisphosphonates. All three bisphosphonates decreased pit formation by osteoclasts. Treatment of osteoclasts with Zometa and much less with Alendronate was capable of inhibiting NK cell cytotoxicity whereas it induced significant secretion of cytokines and chemokines in the cultures of NK cells with osteoclasts. NK cells were able to lyse osteoclasts much more than their precursor cell monocytes and this correlated with the decreased expression of MHC class I and CD54 expression on osteoclasts. These results suggest that zometa treated osteoclasts may remain viable in the microenvironment for a prolonged period of time during interaction with NK cells providing continuous secretion of pro-inflammatory cytokines and chemokines in the absence of anti-inflammatory cytokine IL-10 resulting in the chronicity of inflammation.

Natural killer (NK) cells participate in the clearance of virus-infected and transformed cells, as well as healthy stem cells. The function and role of NK cells in bone remodeling are not well understood. IFN-γ, produced by both NK cells and Th1 lymphocytes, has been shown to inhibit osteoclastogenesis in vitro However, the in vivo effects of IFN-γ on bone tissue are less clear since often provide a contrasting effect when compared to in vitro studies. TNF-α, another key cytokine produced by NK cells, can increase RANKL expression and RANKL dependent osteoclastogenesis. NK cells have also been identified within inflamed synovial fluid and express RANKL and M-CSF which during their interaction with monocytes can trigger the formation of osteoclasts in a process that is RANKL and M-CSF dependent.

As indicated above the role of osteoclasts in bone remodeling and regulation is well established, in contrast, their role as a member of the immune repertoire with a significant role in regulation of both innate and adaptive immune cell function have not been elucidated and is the subject of this paper. Although the role of monocytes and Dendritic cells in the regulation of NK cell function have received considerable attention previously, no or very few reports have shown the effect of osteoclasts on the function of NK cells. In this paper we demonstrate that osteoclasts are potent activators of NK cell function and, indeed, their effect is more potent than monocytes in regulating cytotoxicity and secretion of cytokines and chemokines. In addition, bisphosphonate treated osteoclasts modulate the function of NK cells in such a way which may establish chronic inflammation leading to the pathologies observed in ONJ patients.

Materials and Methods:

Cell Lines, Reagents, and Antibodies. Alpha-MEM medium (Life Technologies, CA) supplemented with 10% FBS and penicillin-streptomycin (Gemini Bio-Products, CA) was used to culture human osteoclasts. Human M-CSF (Biolegend, CA) and soluble RANKL (PeproTech, NJ) were dissolved in alpha-MEM and stored at −20° C. Zometa, Alendronate and Etidronate were purchased from UCLA Ronald Reagan Pharmacy. Fluorescent Zometa analogs were synthesized via a linker strategy (Hokugo et al. 2013). PE conjugated IgG1 and 2b, PE-CD14, PE-CD11b, PE-CD124, PE-B7H1, PE-CD15, PE-CD33, PE-CD44, PE-CD54, PE-MHC-I and PE-MHC-II were all purchased from Biolegend, CA.

Purification of peripheral blood monocytes and generation of osteoclasts. Written informed consents approved by UCLA Institutional Review Board (IRB) were obtained from healthy blood donors and all the procedures were approved by the UCLA-IRB. Peripheral blood mononuclear cells (PBMCs) were obtained after Ficoll-hypaque centrifugation. PBMCs were cultured onto the tissue culture plate for 1 hour after which the adherent subpopulation of PBMCs was detached from the tissue culture plates and the monocytes were purified using isolation kits obtained from Stem Cell Technologies (Vancouver, Canada). Greater than 95% purity was achieved for each subset based on flow cytometric analysis of CD14. Monocytes were cultured in alpha-MEM medium containing 25 ng/mL M-CSF and Rank Ligand (25 ng/mL). Medium was refreshed every 3 days with alpha-MEM containing M-CSF (25 ng/mL) and RANKL (25 ng/mL) for 21 days.

Purification of human NK cells. PBMCs from healthy donors were isolated as described before. Briefly, peripheral blood lymphocytes were obtained after Ficoll-hypaque centrifugation and purified NK cells were negatively selected by using an NK cell isolation kit (Stem Cell Technologies, Vancouver, Canada). The purity of NK cell population was found to be greater than 90% based on flow cytometric analysis of anti-CD16 antibody stained cells. The levels of contaminating CD3+ T cells remained low, at 2.4%±1%, similar to that obtained by the non-specific staining using isotype control antibody throughout the experimental procedures.

TRAP staining. Osteoclasts were detached from tissue culture plate and seeded in 96-well plate at $3\times10^4$ cells/well for 18-24 hours. Afterwards the cells were rinsed twice with 1× PBS and fixed with 10% formaldehyde for 5 minutes at room temperature. The cells were then rinsed three times with 1×PBS and incubated with Chromogenic Substrate solution (Primary Cell, Co., Japan) for 30 minutes or until stained TRAP is clearly seen. Finally, cells were then rinsed with deionized water to neutralize the reaction and images were taken with Leica DMI 6000B inverted microscope.

Pit resorption assay. Purified Human osteoclasts were generated from healthy donor's monocytes and cultured in medium containing M-CSF (25 ng/mL) and RANKL (25 ng/mL) for 21 days. Afterwards, osteoclasts were rinsed, detached from tissue culture plates and seeded at $1\times10^4$ cells/well in 24 well plate pre-coated with synthetic carbonate apatite (Cosmo Bio Co, Japan) for 7 days. After the incubation period, culture medium was removed and cells were rinsed with 5% sodium hypochlorite for 5 minutes. The cells were then washed with water and photographed using Leica DMI 6000B inverted microscope.

ELISA. ELISAs for IFN-γ measurement were performed as described previously [31]. To analyze and obtain the cytokine concentration, a standard curve was generated by either two or three fold dilution of recombinant cytokines.

Multiplex Cytokine Array kit. Fluorokine MAP cytokine multiplex kits were purchased from Life Technologies and the procedures were conducted as suggested by the manufacturer. To analyze and obtain the cytokine concentration a standard curve was generated by threefold dilution of recombinant cytokines provided by the manufacturer. Analysis was performed using MAGPIX (Life Technologies, CA).

Surface Staining. Staining was performed by labeling the cells with antibodies as described above.

$^{51}$Cr release cytotoxicity assay was performed as described above.

Statistical analysis. An unpaired, two-tailed student t-test was performed for the statistical analysis. One way ANOVA with a Bonferroni post-test was used to compare the different groups.

Results

Figure 37:
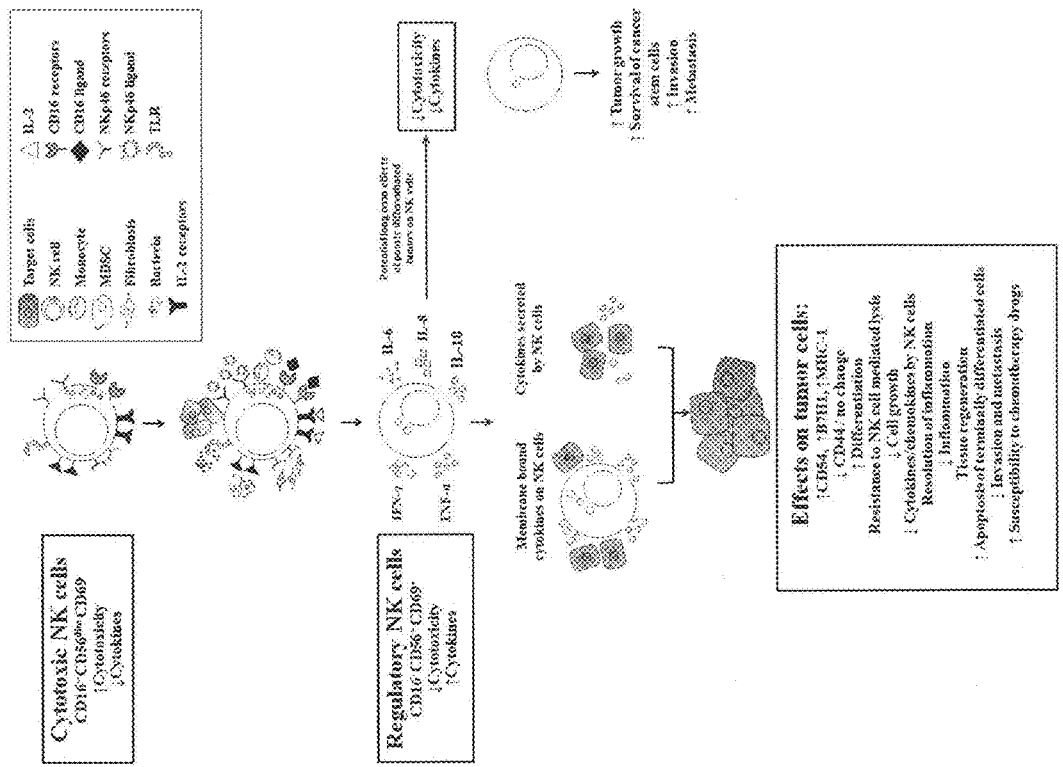
FIG. 37 Hypothetical model of induction of anergized/regulatory NK cells by immune inflammatory cells and by the effectors of connective tissue to support differentiation of non-transformed stem cells and cancer stem cells resulting in their resistance to NK cell mediated cytotoxicity. Induction of NK cell anergy in microenvironment is shown.

Phenotypic and functional characterization of osteoclasts purified from human monocytes. Human osteoclasts were generated using purified monocytes treated with Rank Ligand and M-CSF as described in the Materials and Methods section. Osteoclasts purified from monocytes at day 21 were positive for TRAP staining (FIG. 37). The analysis of cytokines, chemokines and growth factors using multiplex cytokine array demonstrated a gradual increase in the secretion of IL1RA, IL2R, IL12 cytokines and MIP-1a, MIP-1b and Rantes chemokines whereas a decrease in IL-6 cytokine secretion can be observed from day 2 to day 21 of differentiation of monocytes to osteoclasts. Increased detection of IL-15 and IFN-α but not IFN-γ was also observed. The levels of MCP-1 and IL-8 remained significantly high at all-time points tested. No significant secretion of IL-1b, IL-2, IL-4, IL-5, IL-7, IL-13, IL-17 and Eotaxin at the time points and concentration tested. Therefore, osteoclasts have the ability to secrete inflammatory cytokines and chemokines which can play important roles in differentiation and tissue remodeling.

Since there was a gradual decrease in IL-6 secretion from day 2 to 21 we compared the levels of IL-6 decrease to the release of anti-inflammatory cytokine IL-10. In contrast to gradual decrease in IL-6 secretion from day 3 to day 16 of culture, IL-10 secretion in osteoclast precursors exhibited a gradual increase from day 3 to day $16^{th}$. Therefore, there was an inverse modulation of IL-6 and IL-10 during differentiation of osteoclasts from monocyte precursors.

Figure 3C:
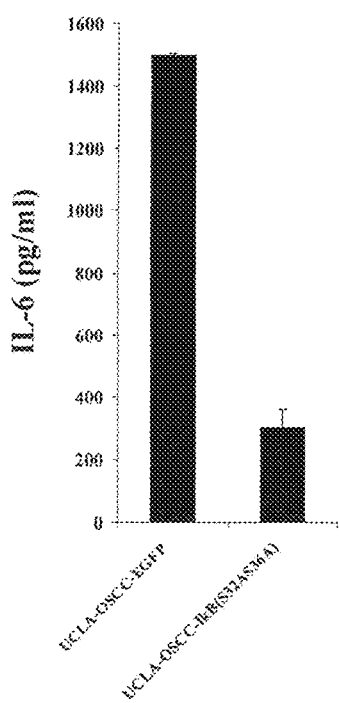
Figure 3D:
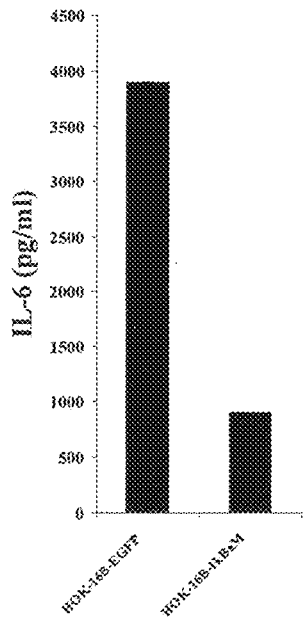
Figure 3E:
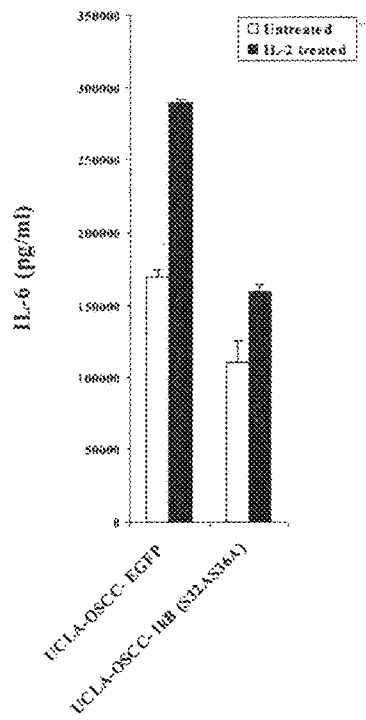
Figure 3F:
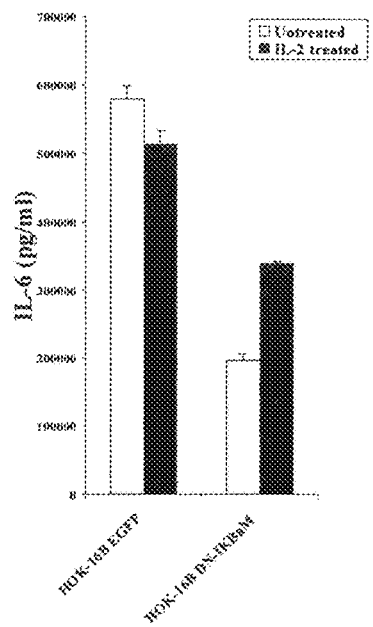
Figure 3G:
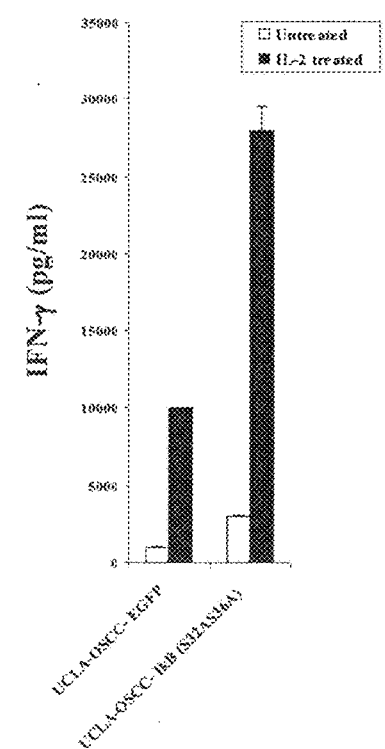
Figure 3H:
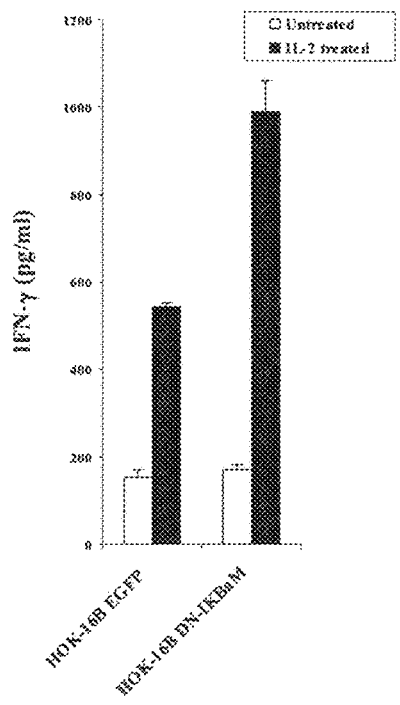
Figure 3I:
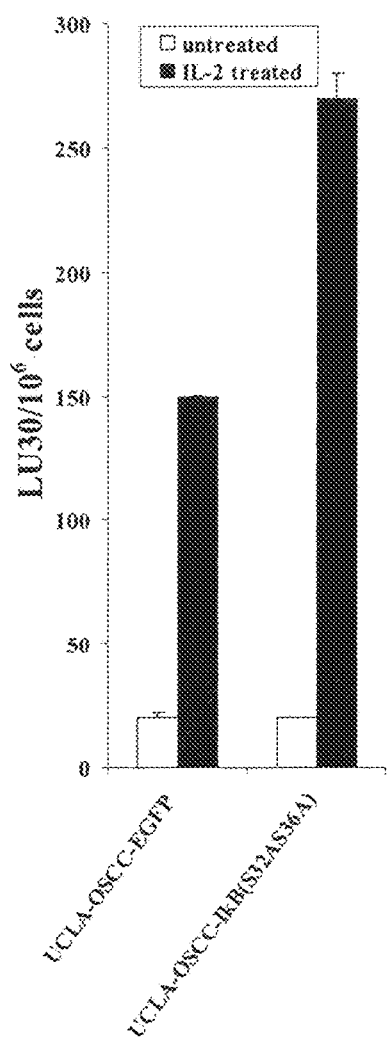
Figure 3J:
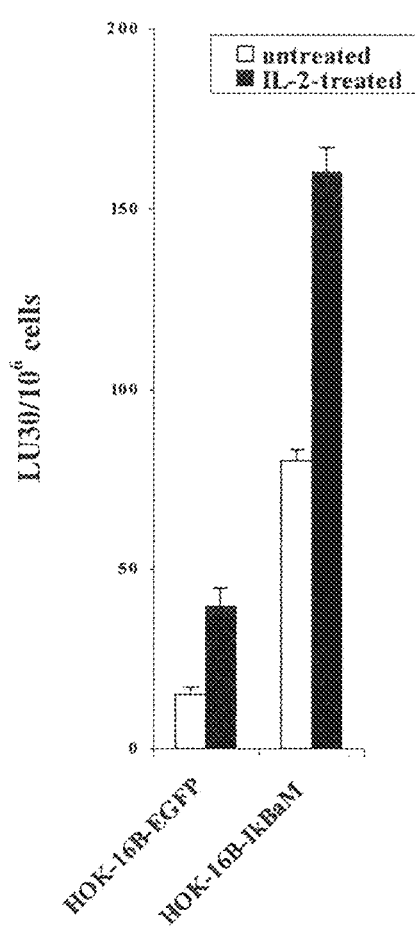

Irradiated PBMCs increased IL-6 secretion but inhibited resorptive activity of the osteoclasts. We then determined the effect of irradiated PBMCs on IL-6 and IL-10 secretion by day 21 differentiated osteoclasts. Addition of irradiated autologous PBMCs to osteoclasts significantly increased the secretion of IL-6 but it had marginal effect on the secretion of IL-10 (FIGS. 3B and 3C). Addition of irradiated PBMCs to osteoclasts abrogated completely the resorptive activity of osteoclasts. In contrast serum prepared from the autologous donor neither had augmenting effect on IL-6 secretion nor had an effect on the resorptive function of osteoclasts indicating that PBMC-osteoclast interaction is likely the mechanism to augment IL-6 secretion and inhibit the resorptive activity of the osteoclasts.

Differential induction of cytokines, chemokines and growth factors by monocytes, M1 and M2 macrophages, Dendritic cells and Osteoclasts. The profile and amounts of cytokines and chemokine secretion in osteoclasts resembled those of the freshly purified monocytes and cultured M2 macrophages, and were greatly distinct from M1 macrophages and Dendritic cells. M1 macrophages demonstrated the highest secretion of cytokines followed by the Dendritic cells which had lower overall secretion for the majority of cytokines tested, although there were some exceptions such as IL-1Ra which was higher from Dendritic cells. The amounts of cytokines were largely similar between freshly isolated monocytes, M2 macrophages and Osteoclasts with Osteoclasts having the lowest secretion. Interestingly, the levels of chemokines were high in all the subsets, M1 macrophages having the highest for the MIP-1a and MIP-1b and the lowest for MCP-1. IL-8 secretion was the highest from M1 macrophages and M2 macrophages, and monocytes had the next highest secretion, whereas Dendritic cells and Osteoclasts secreted lower amounts. Secretion of Rantes was the lowest for the M1 macrophages and higher in the other subsets. Monocytes, M2 macrophages and Osteoclasts secreted highest levels of MCP-1 and IP-10 when compared to DCs or M1 macrophages (Table 2). Osteoclasts had the lowest amounts of growth factor secretion whereas M1 macrophages had the highest with the exception of GM-CSF where they secreted the least. Overall, these results indicated that the profiles of cytokine, chemokine and growth factor secretion of Osteoclasts resemble to the monocytes and M2 macrophages.

Uptake and the pro-inflammatory effect of nitrogen-containing Zometa and Alendronate and non-nitrogen containing Etidronate on Osteoclasts. To determine the effect of bisphosphonates on Osteoclasts, first we determined the specific uptake of fluorescently labeled Zometa by Osteoclasts. Osteoclasts which were taken up zometa appeared red under the microscope since zometa was labeled with red florescence. We then determined the effect of all three bisphosphonates on cell viability. There was a dose dependent increase in cell death when nitrogen containing Zometa and Alendronate were added to Osteoclasts, with Zometa having higher toxicity than Alendronate. The non-nitrogen containing Etidronate did not mediate cell death at any concentration. Both nitrogen-containing Zometa and Alendronate but not Etidronate were able to induce secretion of IL-6 at the level of 1 µM and the levels significantly decreased with the 25-100 µM concentration of Zometa. Alendronate at the levels of 100 µM exhibited significant decrease in IL-6 secretion when compared to 1-25 µM levels. Etidronate at all different concentrations were not able to induce secretion of IL-6. In contrast to elevated secretion of IL-6 by nitrogen containing bisphosphonates, the levels of anti-inflammatory cytokine IL-10 was severely suppressed at the concentrations of 1-50 Etidronate at all concentrations had the ability to increase or retain the secretion of IL-10 by osteoclasts.

Since the highest increase in IL-6 secretion was observed at 1 µM, we then determined the ability of lower concentrations of bisphosphonates to induce IL-6 secretion at the range of 10 nM to 1 µM. The results demonstrated a dose and time dependent increase in IL-6 secretion by Zometa and Alendronate, with Zometa having higher ability to induce IL-6. Etidronate had no or minimal effect on the secretion of IL-6 at all different concentrations. Since both Zometa and Alendronate were found to induce cell death at higher concentrations, we then normalized the levels of IL-6 secretion based on live cells. The results indicated that Zometa exhibited the highest induction followed by Alendronate, with Etidronate having no or minimal activity. When the levels of IL-6 secretion normalized based on the live cells at the concentrations of 1-50 µM similar results to those obtained with the lower concentrations of Zometa and Alendronate were obtained, Zometa having the highest effect on the secretion of IL-6, followed by Alendronate and Etidronate did not change the levels at any concentration. Both Zometa and Alendronate inhibited IL-10 secretion at the concentrations of 1-50 µM. When the amounts were normalized based on the live cells, Zometa demonstrated the highest increase per live cell. The inhibitory effect of Zometa and Alendronate at the lower concentrations was not remarkable, however, still per live cell basis Zometa induced the highest secretion of IL-10, followed by Alendronate and Etidronate having the least activating effect on IL-10 secretion. The inhibitory effect of Zometa and Alendronate were dose and donor dependent.

In addition, to IL-6 and IL-10 secretion, the levels of TNF-α and IL-1β were also determined after bisphosphonate treatment. Dose dependent increase in TNF-α and IL-1β secretion was also observed by Zometa followed by Alendronate and no secretion by Etidronate. Overall, these data demonstrated the ability of both Zometa and Alendronate but not Etidronate to induce pro-inflammatory cytokines, whereas they had inhibitory effect on the release of anti-inflammatory IL-10 since the release of this cytokine was greatly affected by the decreased viability of the cells, even though Zometa had enhancing effect on the secretion of IL-10 per live cell basis.

Decreased pit numbers and size by Bisphosphonate-treated Osteoclasts. The resorptive activity of the osteoclasts was determined after treatment with Zometa, Alendronate and Etidronate. Although dose dependent decrease in the resorptive activity of osteoclasts could be seen by the treatment with the three bisphosphonates, Zometa exerted the most severe inhibition. Both the numbers of the pits and the size of the pits were affected by the treatment with the three bisphosphonates.

Comparison of cell surface receptor expression between Osteoclasts, monocytes, Dendritic cells and macrophages. When cell surface receptor expression was compared between Osteoclasts and freshly isolated autologous monocytes, a significant down-modulation of all the cell surface receptors were observed. Profound decreases in CD14, CD11b, CD44, MHC-class I and II and CD54 were observed on the surface of osteoclasts as compared to freshly isolated autologous monocytes. However, when monocytes were cultured in media in the absence of Rank ligand and M-CSF and the levels compared to Osteoclasts, the differences between monocytes and osteoclasts substantially decreased. The expression levels of CD14, CD11b B7H1 and CD54 increased and CD44 decreased, whereas no differences for MHC class I and II, CD33, CD15, CD124 could be seen. In contrast, the expression of all the cell surface receptors was significantly increased on the surface of macrophages as compared to either monocytes or osteoclasts. DCs expressed higher levels of CD11b, CD54, MHC class II, CD33, B7H1 and CD44 and lower levels of CD14 and MHC class I when compared to monocytes and osteoclasts. When the surface expression of day 8 differentiated Osteoclasts were compared with day 21, a slight increase in CD14, CD11b, CD33, and B7H1 and a decrease in MHC class II were noted. It is of note that even though mean channel florescence intensity of CD14 and CD44 were increased, the percentages of the cells expressing these surface receptors were decreased. Addition of combination of IFN-γ and TNF-α decreased CD44 and increased CD14, CD54, MHC class II, CD33, CD124 and B7H1 whereas no change in CD11b, MHC class I, CD15 were noted.

Zometa modulated surface receptor expression on Osteoclasts. Treatment of Osteoclasts with Zometa increased all the cell surface receptors at lower concentration of Zometa, which correlated with the increased cytokine induction. At higher concentration of Zometa there was less increase in the cell surface receptors. Comparison between Zometa treated Osteoclasts and those treated with the supernatants prepared from the activated NK cells demonstrated higher induction of cell surface receptors by Zometa with the exception of CD54 where supernatant treated Osteoclasts had higher induction. Of note both CD14 and CD44 expression were significantly down-modulated by NK supernatant treated Osteoclasts.

Osteoclasts are targets of NK cells and induce significant IFN-γ secretion by the NK cells. Since osteoclasts express lower levels of MHC class I on the surface they may be targets of NK cell lysis. To determine whether osteoclasts similar to monocytes are targets of NK cells, untreated, IL-2 treated and IL-2 in combination with anti-CD16 treated NK cells were used in cytotoxicity assays against Osteoclasts. Both untreated and IL-2 treated NK cells were able to lyse osteoclasts although the levels of IL-2 treated NK cells were significantly higher than the untreated NK cells. Addition of anti-CD16 mAb triggering antibody with IL-2 inhibited IL-2 induced NK cell cytotoxicity. To compare NK cell cytotoxicity against osteoclasts and monocytes, untreated and IL-2 treated NK cells were used in cytotoxicity assay. NK cells lysed osteoclasts much more than monocytes. In addition, both monocytes and osteoclasts were able to induce significant secretion of IFN-γ by the IL-2 treated NK cells, albeit the levels were higher when NK cells were cultured with osteoclasts than monocytes. NK cells treated with IL-2 in combination with anti-CD16 mAb triggered significant release of IFN-γ, and the combination with monocytes or osteoclasts were unable to increase beyond the amount which was induced by IL-2 in combination with anti-CD16mAb.

Zometa treated Osteoclasts are resistant to NK cell mediated cytotoxicity. We then determined the cytotoxic activity of NK cells against bisphosphonate treated osteoclasts and OSCSCs. IL-2 treated NK cells lysed untreated osteoclasts and the treatment with zometa induced resistance in osteoclasts against NK cell cytotoxicity. Zometa at 500 nM caused more resistance to NK cell mediated cytotoxicity than at 1 μM. The resistance to cytotoxicity is also seen with Alendronate but at much lower levels. To determine whether the ability to induce resistance in NK cells is specific for osteoclasts, we treated OSCSCs for 15-30 min and used in cytotoxicity assay against NK cells. Treatment of OSCSCs with zometa also induced resistance against NK cytotoxicity. The effect of Zometa treated osteoclasts on NK cells is similar to that induced by IL-2+anti-CD16mAb treated NK cells in which NK cytotoxicity is suppressed whereas there is significant induction of cytokine secretion by the NK cells (split anergy).

NK cells secrete significant levels of inflammatory cytokines and chemokines in culture with Zometa treated Osteoclasts. We next determined the effect of bisphosphonates when NK cells were cultured with either zometa or Alendronate treated osteoclasts. As shown in the Table, Zometa treated osteoclasts triggered significantly higher induction of cytokines and chemokines in the co-cultures with NK cells, and the effect was higher when compared to Alendronate treated Osteoclasts, whereas Etidronate had no enhancing effect. As expected, based on surface expression, osteoclasts triggered cytokine and chemokine secretion significantly more than monocytes. IL-2 treated NK cells triggered significantly higher release of IL-6, IFN-g, IL-10, IL-8, MCP-1, MIP-1a and MIP-1b in the cultures with osteoclasts than monocytes. Zometa treated osteoclasts upregulated secretion of cytokines and chemokines 2-6 fold higher for IL-6, IFN-g, MIP1a and MIP-1b by IL-2 and IL-2+anti-CD16mAb treated NK cells when compared to untreated osteoclasts. The levels of IL-8 and MCP-1 secretion were very high and plateaued in the cultures of NK cells with osteoclasts. Both Zometa and Alendronate treated osteoclasts demonstrated decreased secretion of IL-10 in the cultures with NK cells when compared to untreated osteoclasts. Zometa treated osteoclasts secreted higher levels of IL-18 when compared to monocytes, the levels significantly increased when cultured with NK cells.

Phenotypic and functional characteristics of osteoclasts treated with and without two nitrogen containing Zometa and Alendroante and one non-nitrogen containing bisphosphonate Etidronate were determined. Osteoclasts were generated from their precursor cells monocytes and differentiated with Rank Ligand and M-CSF. Initial characterization indicated that during differentiation with Rank L and M-CSF osteoclasts gradually increased the secretion of a number of chemokines and cytokines from day 2 to day 21 of culture, and the profiles of secretion was similar to those of M2 macrophages and monocytes than DCs or M1 macrophages. In comparison to all other subsets, osteoclasts, in general, secreted lower amounts of cytokines, however, they secreted substantial amounts of chemokines. Interestingly, secretion of IL-6 by osteoclasts decreased whereas the IL-10 secretion gradually rose from day 3 of differentiation to day 16, and even though cultures of osteoclasts with PBMCs triggered significant secretion of IL-6 it did not have an effect on the secretion of IL-10. Osteoclasts cultured with PBMCs lost the ability to induce pit formation. Similar to PBMCs, Zometa and Alendronate but not Etidronate treated osteoclasts triggered dose dependent secretion of IL-6 whereas they inhibited the secretion of IL-10. Indeed, in vivo experiments with Zometa injected mice during and after tooth extraction demonstrated significantly higher secretion of IL-6 by osteoclasts when determined in in situ immunohistochemical analysis of oral gingival mucosa indicating clear agreement between our in vitro and in vivo experiments. The dose dependent increase in IL-6 secretion by zometa was evident when Osteoclasts were treated with 10 nM-1 μM, and at higher concentration of zometa from 1 μM-100 μM a dose dependent decrease in the secretion of IL-6 could be observed which related to the ability of zometa to induce functional suppression and/or cell death in osteoclasts since after normalization based on the live cells an increase in IL-6 secretion could be observed in doses of 1 μM-50 μM.

Zometa induced increase of IL-6 was higher when compared to Alendronate whereas Etidronate demonstrated no ability to induce IL-6 secretion. In contrast, IL-10 secretion was not changed from doses 10 nM-1 μM, and at higher concentration of Zometa and Alendronate but not Etidronate a dose dependent suppression of IL-10 secretion could be observed, however, this could be due to the ability of zometa and Alendronate to induce cell death at high concentrations since after normalization based on the live osteoclasts a slight increase in IL-10 secretion in Zometa and much less with Alendronate could be seen. Zometa was also able to induce TNF-α and IL-1β from osteoclasts. The increase in inflammatory cytokines induced by Zometa and to a lesser extent by Alendronate correlated with the inability of Zometa and Alendronate treated osteoclasts to retain their resorptive activity since both the number and size of the pits formed on the resorptive plates were decreased. Interestingly, even though Etidronate did not induce inflammatory cytokines it was able to decrease the ability of osteoclasts to resorb hydroxyapatite significantly.

To determine whether zometa had the ability to modulate surface receptors on osteoclasts we first analyzed a number of key cell surface receptors on osteoclasts and compared it to monocytes, macrophages and DCs. Osteoclasts had significantly down-modulated many of the cell surface receptors, notably, MHC class I and II, CD14, CD11b and CD54. There was 4-25 fold decrease in the expression of surface receptors and the most decrease was seen for MHC class I (8 fold) and II (25 fold) expression on osteoclasts. Considering the size of the osteoclasts such a decrease in surface receptors is quite substantial and it may have significant physiological consequences for the activation of immune inflammatory cells.

Since osteoclasts were compared to freshly isolated monocytes, we next determined the surface receptors when both osteoclasts and monocytes were cultured for 8 days and compared the expression to monocytes treated with IFN-γ and LPS and Dendritic cells generated from monocytes treated with GM-CSF and IL-4. Monocytes cultured for 8 days also down-modulated their surface receptors and the levels of expression remained lower when compared to either 8 day or 21 day cultured osteoclasts for CD14, CD11b and CD54. The levels of MHC class I and II did not change substantially, however, lower amounts of MHC class II were seen on 21 day osteoclast culture. The surface expressions on osteoclasts were quite different from either macrophages or DCs. Activation of osteoclasts with IFN-γ and TNF-α up-regulated the majority of surface receptors, however, the increase never reached to the levels obtained on the surface of macrophages. These experiments suggested that monocytes in the periphery may be less activating for innate immune cells such as NK cells since they retain higher levels of key surface expression such as MHC class I, whereas once they move to the tissues and down-modulate their surface receptors they may become more activating. Indeed, this may be one reason why NK cells in peripheral blood remain relatively quiescent, even in the presence of competent NK cytotoxic machinery.

Treatment of osteoclasts with Zometa up-regulated surface receptors significantly and this increase was comparable or even higher when osteoclasts were treated with culture supernatants from NK cells and monocytes treated with sonicates of gram positive bacteria in which we had obtained the highest increase in surface receptors for cells such as OSCSCs and DPSC.

In our previous studies we determined that the stage of maturation and differentiation of the healthy untransformed stem cells, as well as transformed tumorigenic cancer stem cells, is predictive of their sensitivity to NK cell lysis. In this regard we have shown that OSCSCs, which are stem-like oral tumors, are significantly more susceptible to NK cell mediated cytotoxicity; whereas, their differentiated counterpart OSCCs is significantly more resistant. In addition, hESCs and hiPSCs, as well as a number of other healthy normal stem cells such as hMSCs and hDPSCs, were found to be significantly more susceptible to NK cell mediated cytotoxicity than their differentiated counterparts. Based on these results, we proposed that NK cells play a significant role in differentiation of the cells by providing critical signals via secreted cytokines as well as direct cell-cell contact. In addition, we have shown previously that CD14+ HLADR-monocytes can condition NK cells to lose cytotoxicity and gain the ability to secrete inflammatory cytokines. The signals received from the stem cells or monocytes alter the phenotype of NK cells and cause NK cells to lose cytotoxicity and change into cytokine producing cells. These alterations in NK cell effector function is found to ultimately aid in driving differentiation of surviving, healthy, as well as transformed stem cells. Differentiation of stem cells and their resistance to NK cell mediated cytotoxicity correlated with significant increase in the expression of MHC class I, CD54, B7H1 surface expression in a number of healthy and tumor stem cell models, and it was blocked by the addition of the combination of anti-TNF-α and anti-IFN-γ which restored NK cell cytotoxicity and blocked the increased expression of above-mentioned surface markers in addition to inhibition of cytokine and chemokine secretion. Since Zometa increased MHC class I, CD54 and B7H1 on osteoclasts we reasoned that it may behave as a differentiation agent capable of decreasing NK cell mediated cytotoxicity. Indeed, treatment of osteoclasts with Zometa and much less with Alendronate was able to inhibit NK cell cytotoxicity significantly. In addition, NK cells were able to lyse osteoclasts much more than freshly isolated monocytes and this correlated with the decreased expression of MHC class I and CD54 expression.

In contrast to the decrease in cytotoxicity, Zometa mediated dose dependent increase in cytokine secretion such as TNF-α and IFN-γ in the co-cultures of NK cells with osteoclasts. As mentioned above, TNF-α and IFN-γ secreted by the NK cells synergistically increase differentiation of stem cells resulting in their resistance to NK cell mediated cytotoxicity and substantial decrease in cytokine and chemokine secretion by the NK cells cultured with differentiated cells. Decrease in NK cell cytotoxicity by Zometa can be observed after 30 min. of treatment of cells with Zometa which is quite fast. These results suggest that zometa treated osteoclasts may remain viable in the microenvironment for a prolonged period of time and continuously trigger high levels of cytokines and chemokines resulting in the chronicity of inflammation. Indeed, under the conditions where supernatants from the NK cells induce differentiation in stem cells such as DPSCs or OSCSCs, there is a significant inhibition of both

| IL-6 | IFN-γ | IL-10 | MCP-1 | IL-8 | MIP-1α | MIP-1β |
| --- | --- | --- | --- | --- | --- | --- | cytotoxicity and cytokine and chemokine secretion, however, in the presence of Zometa, even though NK cell cytotoxicity is blocked, cytokine secretion continues at a very high level which may be the reason why complete wound closure does not occur after tooth extraction. In addition, Zometa treated osteoclasts may provide continuous NK cell stimulation by the increased production and synergistic functions of NK activating cytokines such as IL-18, IL-15, IL-12 and IFN-α which we have shown to be secreted by the osteoclasts. Both Zometa and Alendronate but not Etidronate are able to increase cytokine and chemokine secretion by the NK cells in the co-cultures of NK cells with osteoclasts.

The significance and function of Monocyte/macrophages and Dendritic cells in driving an effective immune response has been known for decades, however, their close relative, osteoclasts were primarily known for their function during bone turn-over and remodeling. Our studies impart greater significance to this subset as another subset of the immune system, and place them in the ranks of Monocyte/macrophages and DCs in regulating the function of innate immunity.

Table 3

Production of cytokines, chemokines and growth factors in cultures of NK cells with monocytes and Osteoclasts. Human monocytes purified from healthy donor's PBMCs were differentiated into osteoclasts in culture with medium containing M-CSF (25 ng/mL) and RANKL (25 ng/mL) for 17 days. After 72 hours of treatment of monocytes and cultured osteoclasts with bisphosphonates at 1 uM concentration, treated monocytes and osteoclasts were washed extensively with fresh media and cultured with untreated, IL-2 treated and IL-2+anti-CD16mAb treated NK cells.

Supernatants from the co-cultures of monocytes or osteoclasts with NK cells were harvested after 24 hours of incubation and the levels of cytokine and chemokine production were measured using multiplex cytokine array kit.

| | | | | | | | |
|---|---|---|---|---|---|---|---|
| Media | 7 | 1 | 0 | 56 | 7 | 1039 | 0 |
| Untreated NK | 24 | 1 | 0 | 999 | 1514 | 942 | 375 |
| IL-2 treated NK | 54 | 4 | 0 | 1252 | 3638 | 1039 | 586 |
| IL-2 + anti-CD16mAb treated NK | 2 | 25 | 0 | 3818 | 16969 | 5803 | 20368 |
| Monocytes | 106 | 4 | 0 | 239 | 11217 | 1377 | 375 |
| Monocytes + Untreated NK | 99 | 2 | 0 | 264 | 10426 | 1135 | 163 |
| Monocytes + IL-2 treated NK | 136 | 4 | 10 | 1232 | 11125 | 1232 | 374 |
| Monocytes + IL-2 + anti-CD16mAb treated NK | 424 | 33 | 10 | 28195 | 21638 | 1619 | 4229 |
| hOC | 41 | 4 | 14 | 31691 | 16607 | 1377 | 2129 |
| hOC + Untreated NK | 63 | 4 | 23 | 29258 | 16544 | 1715 | 2185 |
| hOC + IL-2 treated NK | 535 | 4 | 24 | 38655 | 19349 | 1908 | 5680 |
| hOC + IL-2 + anti-CD16mAb treated NK | 3866 | 57 | 82 | 38916 | 23766 | 6114 | 61555 |
| hOC + ZA | 196 | 4 | 14 | 37820 | 18589 | 1425 | 2157 |
| hOC + ZA + Untreated NK | 312 | 6 | 14 | 38159 | 20986 | 1715 | 2538 |
| hOC + ZA + IL-2 treated NK | 3267 | 12 | 20 | 39332 | 22631 | 4294 | 11587 |
| hOC + ZA + IL-2 + anti-CD16mAb treated NK | 11605 | 80 | 31 | 38748 | 24420 | 6105 | 38411 |

Example 7

NK Differentiated Pancreatic Stem-Like Tumors, Lose Metastatic Potential and Undergo Cell Death by Chemo-Drugs while Maintaining Resistance to NK Lysis Materials and Methods Cell Lines, Reagents, and Antibodies.

RPMI 1640 supplemented with 10% Fetal Bovine Serum (FBS) (Gemini Bio-Products, CA) was used for the cultures of human NK cells. Human pancreatic cancer cell lines Panc-1, MIA PaCa-2 (MP2), BXPC3, HPAF, Capan were generously provided by Dr. Guido Eibl (UCLA David Geffen School of Medicine) and PL12 was provide by Dr. Nicholas Cacalano (UCLA Jonsson Comprehensive Cancer Center). Panc-1, MP2 and BXPC3 were cultured DMEM in supplement with 10% FBS and 2% Penicillin-Streptomycin (Gemini Bio-Products, CA). HPAF, Capan and PL12 were cultured in RMPI 1640 medium supplemented with 10% FBS and 2% Penicillin-Streptomycin. Recombinant IL-2 was obtained from NIH-BRB. Recombinant TNF-α and IFN-γ were obtained from Biolegend (San Diego, Calif.). Antibodies to CD16 were purchased from Biolegend (San Diego, Calif.). Anti-MHC class I were prepared in our laboratory and 1:100 dilution was found to be the optimal concentration to use. PE conjugated anti-CD54, anti-CD44 anti-CD166, and anti-B7H1, were obtained from Biolegend (San Diego, Calif.). Monoclonal antibodies to TNF-α were prepared in our laboratory from ascites of mice injected with TNF-α hybridomas, after which the antibodies were purified and specificity determined by both ELISA and functional assays against recombinant TNF-α. Polyclonal IFN-γ antibodies were prepared in rabbits, purified and specificity determined with ELISA and functional assays against rIFN-γ. 1:100 dilution of anti-TNF-α and anti-IFN-γ antibodies was found to be the optimal concentration to block rTNF-α and rIFN-γ function. The human NK purification kits were obtained from Stem Cell Technologies (Vancouver, Canada). Propidium iodide and N-Acetyl Cysteine (NAC) were purchased from Sigma Aldrich (St. Louis, Mo.). Cisplatin and Paclitaxel were purchased from Ronald Reagan UCLA Medical Center Pharmacy (Los Angeles, Calif.).

Purification of NK Cells.

PBMCs from healthy donors were isolated as described before. Briefly, peripheral blood lymphocytes were obtained after Ficoll-hypaque centrifugation and purified NK cells were negatively selected by using an NK cell isolation kit (Stem Cell Technologies, Vancouver, Canada). The purity of NK cell population was found to be greater than 90% based on flow cytometric analysis of anti-CD16 antibody stained cells. The levels of contaminating CD3+ T cells remained low, at 2.4%±1%, similar to that obtained by the non-specific staining using isotype control antibody throughout the experimental procedures. Written informed consents approved by UCLA Institutional Review Board (IRB) were obtained from the blood donors and all the procedures were approved by the UCLA-IRB.

ELISA.

Single ELISAs were performed as described previously [1]. To analyze and obtain the cytokine and chemokine concentration, a standard curve was generated by either two or three fold dilution of recombinant cytokines provided by the manufacturer. Analysis was performed using the Star Station software.

Surface Staining and Cell Death Assays.

Staining was performed by labeling the cells with antibodies or propidium iodide as described previously.

$^{51}$Cr Release Cytotoxicity Assay.

The $^{51}$Cr release assay was performed as described previously [4]. Briefly, different numbers of purified NK cells were incubated with $^{51}$Cr-labeled tumor target cells. After a 4 hour incubation period the supernatants were harvested from each sample and counted for released radioactivity using the gamma counter. The percentage specific cytotoxicity was calculated as follows;

$$\% \text{ Cytotoxicity} = \frac{\text{Experimental cpm} - \text{spontaneous cpm}}{\text{Total cpm} - \text{spontaneous cpm}}$$

LU $30/10^6$ is calculated by using the inverse of the number of effector cells needed to lyse 30% of tumor target cells× 100.

Stem Cell Differentiation with NK Cell Supernatant.

Human NK cells were purified from healthy donor's PBMCs as described above. NK cells were left untreated or treated with anti-CD16mAb (3 ug/ml), IL-2 (1000 units/ml) or a combination or IL-2 (1000 units/ml) and anti-CD16mAb (3 ug/ml) for 18-24 hours before the supernatants were removed and used in differentiation experiments. The amounts of IFN-γ produced by the activated NK cells were assessed with IFN-γ ELISA (Biolegend, CA). Differentiation of MP2 was conducted with gradual daily addition of increasing amounts of NK cell supernatant. On average a total of 5000 pg of IFN-γ containing supernatants obtained from IL-2+anti-CD16mAb treated NK cells was added for 5 days to induce differentiation and resistance of MP2 to NK cell mediated cytotoxicity.

Analysis of Human Pancreatic Cancer Cell Growth in Immunodeficient Mice.

In vivo growth and metastatic behavior of human pancreatic cancer cell lines were determined by orthotopic cell implantation into 8-10 week-old severe combined immunodeficient (SCID) mice (NOD/SCID; IL-2Rγ$^{-/-}$, lacking T, B, and natural killer cells), as previously described. To establish orthotopic tumors, mice were first anesthetized with ketamine (100 mg/kg) and xylzine (10 mg/kg), and then the pancreas was exposed through an abdominal incision (laparotomy). Tumor cells were then transferred by direct injection of a single cell suspension ($5 \times 10^5$ cells) into the pancreas or transplantation of a subcutaneous tumor fragment (2 mm$^3$) onto the pancreas, secured by a 7-0 Prolene suture. After tumor implantation, all mice were monitored at least twice weekly for disease progression by abdominal palpation and for overall signs of morbidity such as ruffled fur, hunched posture, and immobility. Moribund mice were euthanized by isofluorane or CO2 inhalation. For survival studies, mice were followed until death or euthanized when signs of morbidity were evident. Tumor size was measured with a caliper. Pancreatic tumors, livers, and lungs were harvested from mice at the end of the experiment following orthotopic tumor implantation or when tumor size reached 2 cm diameter.

Statistical Analysis.

An unpaired, two-tailed student t-test was performed for the statistical analysis. One way ANOVA with a Bonferroni post-test was used to compare the different groups.

Results

The stage of differentiation in pancreatic tumors correlates with susceptibility to NK cell mediated cytotoxicity; Loss of NK cell cytotoxicity and gain in secretion of IFN-γ after NK cell receptor triggering. Six pancreatic tumor cells were used to determine surface expression, susceptibilty to NK cell mediated cytotoxicity and secretion of cytokiens when cultured with NK cells. Poorly differentiated MP-2 and Panc-1 expressed higher amounts of CD44 and moderate or low levels of MHC class I and CD54. Moderately differentiated BXPC3 and HPAF expressed moderate to high levels of CD44 and CD54 and higher levels of MHC class I. Well differentiated Capan and PL12 had much lower levels of CD44 and higher levels of CD54 and MHC class I. A direct correlation between the stage of differentiation and susceptibility to NK cell mediated cytotoxicity was observed in pancreatic tumor cells. Undifferentiated MP2 and Panc-1 exhibited the highest whereas PL-12 and Capan well differentiated tumors demonstrated the lowest sensitivity to NK mediated lysis. Moderately differentiated BXPC3 and HPAF demonstrated intermediate sensitivity to NK cell lysis. IL-2 treated NK cells had the highest increase in cytotoxicity and the addition of anti-CD16mAb to both untreated and IL-2 treated NK cells decreased NK cell mediated cytotoxicity significantly against all the tumors. Significant secretion of IFN-γ in the co-cultures of IL-2 treated NK cells with MP2 was observed, and the levels were significantly higher than that seen when NK cells were cultured with PL12. The combination of IL-2 and anti-CD16mAb treatment of NK cells although inhibited NK cell cytotoxicity, it induced higher release of IFN-γ when cultured with and without MP2 and PL12 tumors. The levels of IFN-γ secretion remained less in the co-cultures of NK cells with PL12 when compared to those cultured with MP2.

The induction of resistance of MP2 cells to NK cell mediated cytotoxicity by IL-2+ anti-CD16mAb treated NK cells is mediated by the combination of IFN-γ and TNF-α and not each cytokine alone. Treatment of MP2 with IL-2+ anti-CD16mAb treated NK cell supernatants decreased NK cell mediated cytotoxicity significantly by both untreated and IL-2 treated NK cells (P<0.05). A lower decrease in susceptibility of MP2 cells to NK cell mediated cytotoxicity could also be observed when MP2 cells were treated with supernatants obtained from untreated NK cells. To examine the mechanism by which MP2 tumors become resistant, we determined NK cell mediated cytotoxicity after the addition of each of IFN-γ and TNF-α antibodies alone or in combination with IL-2+anti-CD16mAb treated NK supernatants to MP2 tumors. The addition of each of the IFN-γ and TNF-α antibodies alone had a slight inhibitory effect on the induction of resistance of MP2 cells by the supernatants of NK cells treated with IL-2+anti-CD16mAb; however, the combination of anti-IFN-γ and anti-TNF-α antibodies abrogated the resistance of treated MP2 cells completely. The restoration of MP2 susceptibility to NK cell mediated lysis by the combination of anti-IFN-γ and anti-TNF-α antibodies could be observed when either untreated or IL-2 treated NK cells were used to assess cytotoxicity. Resistance of MP2 to NK cell mediated cytotoxicity induced by supernatants from IL-2+anti-CD16mAb treated NK cells correlated with the increased expression of CD54, B7H1 and MHC-1 as shown in FIG. 3B, and the addition of the combination of anti-IFN-γ and anti-TNF-α antibodies abrogated the increase completely. The effect of anti-IFN-γ mAb in the absence of anti-TNF-α antibody, however, was more dominant for surface receptor modulation than cytotoxicity, since its addition abrogated the increase in surface receptor expressions substantially. In addition, the rate of MP2 cell proliferation was decreased when supernatants obtained from IL-2+anti-CD16mAb treated NK cells were added, and this decrease was significantly inhibited in the presence of the combination of anti-IFN-γ and anti-TNF-α antibody, and not each antibody alone. No cell death could be observed in MP2 cells treated with any of the abovementioned NK supernatants.

The levels of MHC class I gradually decreased from day 0-12 after NK supernatant removal from the differentiated MP2 tumors (data not shown). Indeed there was a two-fold decrease in MHC class 1 expression from day 0 of the removal of NK cell supernatants to day 2 of the cultures and by day 12 the levels were similar to that obtained with untreated MP2 cells. Thus, there was a time dependent decrease in the expression of MHC class I which correlated with restoration of sensitivity to NK cell mediated cytotoxicity and increased cytokine secretion in co-cultures of NK cells with IL-2+anti-CD16mAb NK supernatant differentiated MP2 tumors when NK supernatants were removed and replaced with media from day 0-12.

Combination of rTNF-α and rIFN-γ induce differentiation and resistance of MP2 cells to NK cell mediated cytotoxicity. MP2 and Capan were treated with rTNF-α and rIFN-γ and their susceptibility to NK cell mediated lysis was assessed in a standard 4 hour $^{51}$Cr release assay. The addition of rTNF-α to MP2 was able to induce moderate resistance against NK cell mediated cytotoxicity whereas IFN-γ induced significant resistance. Combination of rTNF-α and rIFN-γ were able to upregulate CD54, MHC-1 and B7H1 and down modulate CD44 in MP-2 tumors. Both TNF-α and IFN-γ were able to increase surface expression of CD54 and MHC class I, however, only IFN-γ was able to upregulate B7H1. As indicated above Capan expressed higher surface expression of CD54, MHC class I and B7H1 and the levels further increased by TNF-α and IFN-γ and the their combination.

Treatment of MP2 with supernatants from IL-2 and anti-CD16mAb treated NK cells significantly inhibited the secretion of IFN-γ and IL-8 by NK cells. We next determined whether decrease in NK cytotoxicity correlated with a decrease in cytokine and chemokine secretion in co-cultures of NK cells with MP2 treated with supernatants from anergized NK cells. Treatment of MP2 with IL-2+anti-CD16mAb treated NK cell supernatant significantly decreased secretion of IFN-γ and IL-8 by freshly isolated untreated, IL-2 treated and IL-2+anti-CD16mAb treated NK cells. The addition of anti-TNF-α antibody or anti-IFN-γ antibody to co-cultures of NK cells with MP2 tumors treated with supernatants from NK cells stimulated with IL-2+anti-CD16mAb increased the levels of both IFN-γ and IL-8. However, the increase in IFN-γ and IL-8 with anti-IFN-γ antibody was more substantial than that mediated by anti-TNF-α. The increase in the secretion of IFN-γ and IL-8 was also observed when they were cultured in the presence of the combination of anti-TNF-α and anti-IFN-γ.

Increased induction of cell death by NAC in well differentiated PL12, Capan and OSCCs and not in poorly differentiated stem-like MP2 and OSCSCs; effect on CDDP mediated cell death. The effect of N-Acetyl Cysteine (NAC), previously characterized as a differentiation agent, was determined on MP2 and OSCSCs and differentiated PL12, Capan and OSCCs. Addition of NAC to either MP2 or OSCSCs had no significant effect on cell viability, however, when added to PL-12, Capan or OSCCs induced significant cell death. Addition of CDDP to MP2 and OSCSCs had no or moderate effect in inducing cell death, whereas when added to PL-12, Capan and OSCCs it induced significant cell death. Addition of NAC not only induced higher death in untreated PL12, Capan and OSCCs but also it inhibited CDDP mediated cell death in all cells tested. In contrast to CDDP, NAC synergistically increased Paclitaxel mediated cell death in PL-12, Capan and OSCCs, whereas had slight to moderate effect on Paclitaxel mediated cell death in MP2 and OSCSCs. Paclitaxel had dose dependent effect on induction of death in PL12, Capan. Both MP2 and OSCSCs were resistant to Paclitaxel mediated cell death, although at very high concentration of Paclitaxel (1000 nM) significant cell death could be observed against OSCSCs but not MP2s.

NAC, CDDP and Paclitaxel induce significant cell death in MP2s differentiated with IL-2+anti-CD16mAb treated NK supernatant. Differentiation of MP2s with supernatants from IL-2+anti-CD16mAb treated NK cells resulted in a significant susceptibility to CDDP which was significantly blocked by the addition of NAC. Similar to those seen with PL-12, Capan and OSCCs addition of NAC to MP2s differentiated with supernatants from IL-2+anti-CD16mAb treated NK cells mediated increased cell death. Blocking of IL-2+anti-CD16mAb treated NK supernatant differentiated MP2 cells with anti-IFN-γ and anti-TNF-α substantially decreased the levels of cell death induced by either NAC or CDDP to the levels that were seen with untreated or those treated with the untreated NK cell supernatant treated MP2s. Similarly, paclitaxel mediated higher cell death of IL-2+ anti-CD16 treated NK supernatant differentiated MP2s and NAC significantly increased paclitaxel mediated cell death. Blocking of IL-2+anti-CD16mAb treated NK supernatant differentiated MP2 cells with anti-IFN-γ and anti-TNF-α substantially decreased the levels of cell death induced by either Paclitaxel and/or NAC to the levels that were seen with untreated MP2s).

Lack of tumor growth and metastasis and long term survival of mice after orthotopic injection of IL-2+anti-CD16mAb stimulated NK cell supernatant differentiated MP2 tumors in pancreas. To determine whether IL-2+anti-CD16 mAb stimulated NK cell supernatant differentiated MP2 loses the ability to grow significantly and establish in the pancreas of NOD/SCID; IL-2Rγ$^{-/-}$ mice we first injected mice (n=9) with MP2 stem-like tumors and compared the growth rate and metastatic ability to PL12 well differentiated tumors (n=9). MP2 stem-like tumors grew within 4 weeks and metastasized to both liver and lungs and killed the animals whereas mice injected with PL12 generated very small tumors within 12 weeks and did not metastasize nor kill the animals. Injection of IL-2+anti-CD16 mAb stimulated NK cell supernatant differentiated MP2s to pancreas (n=6) did not exhibit growth nor metastasized to liver and lung and all mice survived at 12 weeks when the experiment was terminated. Since all of the IL-2+anti-CD16 mAb stimulated NK cell supernatant differentiated MP2s reverted to their stem-like phenotype after 12 days of incubation when NK supernatants were removed from the cells and replaced by control media, as evidenced by gradual decrease in expression of MHC class I and CD54 and B7H1 and gain in susceptibility to NK cell mediated cytotoxicity, we injected the reverted MP2 cells (Diff-MP2-R) in the pancreas (n=3) and observed their growth and metastatic potential. Although Diff-MP2-R grew to a smaller size than the untreated MP2s, it retained its metastatic potential to liver.

Example 8

Sustained and Elevated Cytokine and Chemokine Release by Tumor Cells and Prevention of NK Cell IFN-γ Release and Cytotoxicity After Differentiation of Brain Cancer Stem Cells is Mediated by IFN-γ and TNF-α

Materials and Methods:

Cell Lines, Reagents, and Antibodies. RPMI 1640 supplemented with 10% FBS (Gemini Bio-Product) was used for the cultures of human NK cells and monocytes. Stem-like GBMs were isolated from freshly resected human tumor tissues as described previously [23] and they were seeded at 1×10$^5$ cells/mL into culture flasks pre-coated with laminin (1 mg/mL; BD Bioscience) and Poly-L-Ornithine (15 ug/mL; Sigma Aldrich). The cells were cultured in medium containing DMEM/F12 (Gemini Bio-Products) supplemented with penicillin G, streptomycin sulfate, B-27 (1:50; Gemini Bio-Products), recombinant human Fibroblast Growth Factor (hFGF-2, 20 ng/mL, R&D Systems), recombinant human Epidermal Growth Factor (hEGF, 20 ng/mL, R&D Systems) and Leukemia Inhibitory Factor (LIF, 1000 U/mL). The medium was refreshed every 3 days. Recombinant IL-2 was obtained from NIH-BRB. The human NK purification kits were obtained from Stem Cell Technologies. The anti-CD44 were obtained from Biolegend. Antibodies for CD16 were purchased from Biolegend. EGFR antibody (Erbitux) was purchased from UCLA pharmacy.

Purification of NK cells and monocytes. NK cells and monocytes were purified from healthy donors using negative isolation kits from Stem Cell Technologies as described previously. Monocytes were irradiated at 20 Gy. Written informed consents approved by UCLA Institutional Review Board (IRB) were obtained from the blood donors and all the procedures were approved by the UCLA-IRB.

XO2GB CSC differentiation with NK cell supernatant. To differentiate XO2GB with NK cell supernatants, the NK cells were left untreated or treated with the combination of anti-CD16mAb (3 ug/ml) and IL-2 (1000 units/ml) in the presence or absence of autologous monocytes (1:1 NK:monocyte) for 18-24 hours before the supernatants were removed and used in differentiation experiments. The amounts of IFN-γ produced by activated NK cells were assessed with IFN-γ ELISA (Biolegend). Differentiation of OSCSCs and XO2GB was conducted with gradual daily addition of increasing amounts of NK cell supernatants. On average a total of 0.001 pg of IFN-γ containing supernatants obtained from IL-2+anti-CD16mAb treated NK cells was added per tumor cell for 5 days to induce differentiation and resistance of OSCSCs to NK cell mediated cytotoxicity. XO2GB cells required on average a total of 0.035 pg of IFN-γ containing supernatants from IL-2+anti-CD16mAb treated NK cells per tumor cell during a 7 day treatment. $1 \times 10^6$ tumor cells were cultured and treated with NK supernatants for differentiation. After differentiation target cells were rinsed with 1×PBS, detached and used for experiments.

ELISA. ELISAs for IFN-γ, IL-6 and IL-8 (Biolegend) measurement were performed as described previously.

Surface Staining. Staining was performed by labeling the cells with antibodies as described previously.

$^{51}$Cr release cytotoxicity assay. The $^{51}$Cr release assay was performed as described previously and the LU $30/10^6$ was calculated by using the inverse of the number of effector cells needed to lyse 30% of target cells×100.

Statistical analysis. An unpaired, two-tailed student t-test was performed for the statistical analysis. One way ANOVA with a Bonferroni post-test was used to compare the different groups.

Results:

Induction of split anergy in NK cells after treatment with IL-2+anti-CD16mAb inhibits NK cell mediated cytotoxicity against GBM tumors but increases secretion of IFN-γ. The brain (XO2GB) CSCs exhibited spheroid morphology and formed tumors in the brain of immunodeficient mice with high proliferative capacity. IL-2 activated NK cells were able to lyse X02GB CSCs significantly more than differentiated U87 GBMs (FIG. 1A) and they were also able to induce significant secretion of IFN-γ. A significant decrease in cytotoxicity could be observed when NK cells were treated with IL-2+anti-CD16mAb as compared to IL-2 treated NK cells cultured with XO2GB and U87. However, the levels of IFN-γ secretion was significantly more by IL-2+anti-CD16mAb treated NK cells when compared to IL-2 induced secretion of IFN-γ by the NK cells co-cultured with and without X02GB CSCs and U87. Anti-CD16mAb treated NK cells lost significant cytotoxicity and were unable to elevate IFN-γ secretion. IL-2 treated NK cells in the absence of brain tumors also secreted IFN-γ, however, the levels were less than those secreted by IL-2 treated NK cells cultured with either U87 or X02GB. Combination of IL-2 with anti-CD16mAb treated NK cells secreted significantly higher levels of IFN-γ in the absence of tumors and the levels increased when cultured with either U87 or X02GB brain stem cells.

Supernatants from the combination of IL-2+anti-CD16mAb treated NK cells induced resistance of XO2GB to NK cell mediated cytotoxicity. Treatment of XO2GB with IL-2+ anti-CD16mAb treated NK cell supernatants decreased NK cell mediated cytotoxicity significantly by freshly isolated untreated, IL-2 treated or IL-2+anti-CD16mAb treated NK cells (P<0.05). Resistance of XO2GB to NK cell mediated cytotoxicity could also be observed after their treatment with supernatants from IL-2 treated NK cells, however, the levels of resistance were significantly lower when compared to those induced by IL-2+anti-CD16mAb treated NK cell supernatants.

To examine the mechanisms by which XO2GB CSCs became resistant by anergized NK cells, we determined NK cell mediated cytotoxicity when XO2GBs were treated with supernatants of NK cells treated with IL-2+anti-CD16mAb in the presence and absence of each of IFN-γ and TNF-α antibodies alone or in combination. The addition of TNF-α antibody alone had a slight inhibitory effect whereas antibody to IFN-γ had significant inhibitory effect on the induction of resistance of XO2GB by the supernatants of NK cells, and the combination of anti-IFN-γ and anti-TNF-α abrogated the resistance of treated XO2GBs completely. The inhibition of XO2GB resistance to NK cell mediated cytotoxicity by either anti-IFN-γ antibody alone or the combination of anti-IFN-γ and anti-TNF-α antibodies could be observed when untreated, IL-2 treated or IL-2+anti-CD16mAb treated NK cells were used to assess cytotoxicity. Treatment of XO2GB with the combination of anti-TNF-α and anti-IFN-γ in the absence of NK supernatants had no effect on NK cell cytotoxicity.

Induction of NK resistance in XO2GB by supernatants from IL-2+anti-CD16mAb treated NK cells correlated with the increased expression of CD54 and MHC class I. We then assessed expression of key cell surface receptors after differentiation of XO2GBs with supernatants from IL-2+anti-CD16mAb treated NK cells. Among many surface receptors tested, CD44, CD54 and MHC class I expression were found to correlate significantly with the differentiation and resistance of NK sup-differentiated XO2GBs. The levels of CD54 and MHC class I increased substantially on XO2GB after the addition of IL-2+anti-CD16mAb treated NK cell supernatants. Supernatants from untreated NK cells did not have significant effect on surface expression of XO2GBs. The addition of a combination of anti-TNF-α and anti-IFN-γ antibodies along with IL-2+anti-CD16mAb treated NK supernatants prevented the up-regulation of CD54 and MHC class I on XO2GB. Either anti-TNF-α or anti-IFN-γ was able to decrease CD54 and MHC class I, and the addition of the combination of antibodies abrogated the increase in CD54 and MHC class I, although the effect of anti-IFN-γ appears to be more dominant than anti-TNF-α in blocking the increase in CD54 and MHC class I surface receptors on XO2GBs.

We have previously shown that monocytes induce significant split anergy in NK cells, therefore, we determined the expression of CD54, B7H1, and MHC class I on XO2GBs which were treated with supernatants from IL-2+anti-CD16mAb treated NK cells cultured with irradiated monocytes. The addition of irradiated monocytes in the absence of NK cells did not change the CD54, B7H1 and MHC class I surface expression significantly. However, when monocytes were added to IL-2+anti-CD16mAb NK cells, they synergistically increased the expression of all three receptor expression. Accordingly, the levels of resistance to NK cell mediated cytotoxicity in XO2GB rose significantly higher when compared to XO2GBs cultured with supernatants treated with IL-2+anti-CD16mAb treated NK cells in the absence of monocytes.

To determine growth dynamics of XO2GBs after treatment with the NK supernatants the numbers of XO2GBs were counted after treatment with the NK cell supernatants by microscopic evaluation, and the levels of cell death were determined by staining with propidium iodide followed by flow cytometric analysis. There was a decrease in the numbers of XO2GBs after their culture with IL-2+anti-CD16mAb treated NK cell supernatants when compared to untreated XO2GBs or those treated with untreated NK cell supernatants. However, the highest decrease was observed when XO2GBs were cultured with the supernatants obtained from the combination of IL-2+anti-CD16mAb treated NK cells with monocytes (data not shown). Anti-TNF-α antibody increased the numbers of IL-2+anti-CD16mAb differentiated XO2GBs, and anti-IFN-γ or the combination of anti-TNF-α and anti-IFN-γ antibodies restored the levels of cell growth to the levels observed with untreated XO2GBs. No detached XO2GB could be observed in any of the treatments tested. In addition, no significant cell death could be observed in XO2GBs treated with the supernatants from IL-2+anti-CD16mAb treated NK cells in the absence and presence of irradiated monocytes.

Although treatment of XO2GB with supernatants from IL-2+anti-CD16mAb treated NK cells was able to inhibit NK cell cytotoxicity, it increased IL-6 and IL-8 while inhibiting IFN-g in the co-cultures of NK cells with tumors. Unlike Oral Squamous Cancer Stem Cells (OSCSCs) in which treatment with supernatants from NK cells treated with IL-2+anti-CD16mAb inhibited NK cell cytotoxicity and increased CD54 and MHC class I and blocked secretion of cytokines and chemokines significantly, differentiation of XO2GBs with IL-2+anti-CD16mAb treated NK cell supernatants and cultured with IL-2 treated NK cells had approximately 20% inhibitory effect on the secretion of IFN-γ while it significantly up-regulated the release of IL-6 and IL-8 when compared to either untreated XO2GB, or those treated with anti-IFN-γ and/or anti-TNF-α with IL-2+anti-CD16mAb treated NK supernatants or treated with supernatants from untreated NK cells. Therefore, increase in IL-8 and IL-6 after differentiation of XO2GB with IL-2+anti-CD16mAb treated NK supernatants is mediated by the functions of either TNF-α or IFN-g since blocking of each cytokine or both together inhibited increased secretion of IL6 and IL-8. In addition, increased secretion of IL-8 and IL-6 could be seen in IL-2+anti-CD16mAb NK supernatant differentiated XO2GB cells regardless of whether they were cultured with or without untreated or IL-2 treated NK cells. Surprisingly, pre-treatment of XO2GBs with untreated NK supernatants even though was also inhibitory for the secretion of IFN-g after their co-cultures with IL-2 treated NK cells, this treatment, unlike IL-2+anti-CD16mAb treatment of XO2GBs, did not have any significant effect on IL-6 or IL-8 secretion in the presence and absence of untreated and IL-2 treated NK cell co-cultures. Thus, differentiation of XO2GBs with IL-2+anti-CD16mAb treated NK cell supernatants, has some inhibitory effect on IFN-g secretion by the IL-2 treated NK cells while it has significant activating effect on IL-6 and IL-8 secretion in the presence or absence of their co-cultures with NK cells.

We then assessed the levels and function of TNFR I and II and IFN-γ Rα and IFN-γ Rβ on XO2GBs and compared the levels to those expressed on OSCSCs to determine whether the magnitude of functional differences observed in differentiation could relate to the lower expression of these receptors on XO2GBs. Both the levels and function of these receptors were lower on XO2GBs than on OSCSCs. When compared to XO2GBs much higher expression of TNFRI and IFN-γRα and IFN-γRβ could be seen on OSCSCs than XO2GBs and differentiation with IL-2+anti-CD16mAb treated NK supernatants decreased the levels of TNFRI, II and IFN-γRβ on OSCSCs and not on XO2GBs. Similarly, the addition of the combination of rTNF-α and rIFN-γ to OSCSCs decreased the levels of TNFRI, II and IFN-γRβ, but not IFN-γRα.

In this report we present evidence that NK cells lyse brain cancer stem cells significantly more than their NK cell differentiated counterparts. We have previously demonstrated that the stage of maturation and differentiation of tumors is predictive of their sensitivity to NK cell lysis. NK cells may play a significant role in differentiation and subsequent resistance of the cells by providing critical signals via secreted cytokines as well as direct cell-cell contact.

In order to drive differentiation NK cells are conditioned by immune effectors such as monocyte-macrophages in the tumor stroma in order to lose cytotoxicity and gain in cytokine producing phenotype. When comparing differentiation of XO2GBs to OSCSCs with the IL-2+anti-CD16mAb treated NK cell supernatants we observed the following differences. To induce resistance to the NK cell mediated cytotoxicity, decrease in tumor proliferation and increase in CD54, B7H1 and MHC class I expression, an increased NK supernatant containing IFN-γ was required to differentiate XO2GBs in comparison to OSCSCs. Interestingly, IL-2+anti-CD16mAb treated NK supernatants were not only able to induce resistance to NK cell mediated cytotoxicity and decrease proliferation of OSCSCs, but it also inhibited cytokine and chemokine secretion in the cultures of NK cells with OSCSCs. In contrast, although treatment of XO2GBs with IL-2+anti-CD16mAb treated NK supernatants inhibited NK cell cytotoxicity significantly and decreased IFN-γ secretion, loss of NK cell cytotoxicity and decrease in IFN-g secretion were paralleled with significant increases in IL-6 and IL-8 secretion from XO2GBs differentiated with supernatants from NK cells activated by IL-2+anti-CD16mAb. In addition, unlike OSCSCs in which NK supernatants from IL-2+anti-CD16mAb activated NK cells could promote cell death in a subpopulation of OSCSCs after differentiation [1], IL-2+anti-CD16mab activated NK supernatants was unable to induce cell death in XO2GBs. These experiments revealed crucial differences between GBMs and oral tumors in their responses to NK cell mediated differentiation, which is likely one of the underlying mechanisms for GBMs aggressive behavior and poor prognosis in patients. GBMs, may therefore, survive because of the inability of NK cells to lyse, in addition to their resistance to cell death induced by death inducing cytokines such as TNF-α and Fas Ligand. Thus, GBMs may persistently remain inflammatory since upon differentiation with NK cell supernatants, they increase rather than decrease inflammatory cytokines and chemokine IL-6 and IL-8, whereas differentiation with NK cell supernatants block secretion of inflammatory cytokines in the cultures of NK cells with differentiated OSCSCs. Lack of cell death and decreased ability to control the release of inflammatory cytokines and chemokines in NK differentiated XO2GBs co-relates with the lower surface expression and function of TNF-α and IFN-γ receptors. OSCSCs express much higher levels of TNFRI and IFN-γRα and IFN-γRβ when compared to XO2GBs. Accordingly, upon differentiation with IL-2+anti-CD16mAb treated NK supernatants or treatment with the rTNF-α and/or rIFN-γ OSCSCs down-modulate both TNFRI and IFN-γRβ, suggesting an increased receptor signaling and function, whereas no changes could be seen for XO2GBs. Therefore, strategies to augment both TNF-α and IFN-γ receptors on GBMs may be effective in the control of these tumors.

GBM patients are likely to benefit from NK cell transplantation since NK cells are capable of eliminating cancer stem cells. In this regard depletion of NK anergizing effectors such as monocytes or other Myeloid Derived Suppressor Cells (MDSCs) in patients before NK cell transplantation should provide such strategy for targeting GBM cancer stem cells by the NK cells. In addition, this strategy may also decrease the ability of NK cells to secrete cytokines and chemokines due to the removal of synergizing effect of monocytes with NK cells for the secretion of TNF-α and IFN-γ.

Interestingly, secretion of TNF-α and IFN-γ by IL-2+anti-CD16mAb treated NK cells is responsible for the increased induction and secretion of inflammatory cytokines and chemokines by NK differentiated XO2GBs, which is remarkably different from oral, lung and pancreatic tumors which we have tested previously and in which a significant decrease rather t Tumor differentiation by NK cell supernatants containing TNF-α and IFN-γ was not only responsible for the decrease in inflammatory cytokines and chemokines in oral and pancreatic tumors, but it also inhibited tumor invasion and metastasis in animals.

It is unclear why GBMs behave differently from other tumors in regards to their response to differentiation by the NK cell supernatants, however, considering elevated inflammatory index in patients with GBMs and its underlying role in cancer progression, strategies for immune-therapeutics should be designed to retain tumor killing function of NK cells in the absence of increased cytokine or chemokine production. In this regard combination therapy can be developed in which either a broad inhibitor of cytokine release or specific inhibitor such as anti-IL-6 antibody can be used to target GBM tumors. The model provided herein is an appropriate pre-clinical model to test many such combination therapies before their applications to patients.

Example 9

In Vivo Analysis with NOD SCID Gamma (NSG), and Humanized Bone Marrow, Thymus and Liver Transplanted (BLT) Mice NSG and BLT mouse models were used to inject oral tumor cancer stem cells (OSCSCs) in the floor of the mouth of oral cavity; and to surgically implanted pancreatic cancer stem cells in the pancreas to establish tumors. A week after implantation of the tumors, expanded NK cells (which were activated by the presence of IL-2+ anti-CD16mAb+sAJ2+ Osteoclasts) were injected by tail vein injections. After 3-6 weeks of tumor growth in animals which did not receive NK cells all the animals were sacrificed and the dynamics of tumor growth and their effect on weight loss, body conditioning, size of the tumor, and several immunological parameters within the tumor and peripheral blood as well as in spleen, liver, pancreas, pen pancreatic adipose tissue and bone marrow were investigated.

The NSG mouse lacks competent T, B and NK cells. The BLT mouse is fully humanized, and has been implanted with human fetal thymus and liver under the kidney capsule, and reconstituted with CD34+ human hematopoietic stem cells which give rise to fully reconstituted human immune cells. The percent of NK cells are about 5% whereas the majority are T and B cells. This, the BLT mice provide a useful animal model for the activity of a human functional immune system.

Results

Oral tumors (OSCSCs). NSG and BLT animals that receive oral tumors grew large tumors, and the tumors in NSG were larger than those in BLT. BLT and NSG animals which received oral cancer stem cells exhibited very severe weight loss and the animals were relatively inactive, demonstrated hunched back posture and demonstrated significant wasting.

BLT animals that were implanted with the tumors and injected with expanded NK cells had very small tumors. No weight loss could be observed and they were very active similar to the control animals which were not implanted with the tumors.

All the immunological parameters in BLT animals which received expanded NK cells were significantly higher in comparison with those that did not receive NK cells. There was significant levels of IFN-γ secreted by the peripheral blood mononuclear cells, bone marrow immune cells, and splenocytes. Liver immune cells exhibited the inverse in which animals that did not receive NK cells exhibited higher IFN-γ secretion and the levels of IFN-γ from liver in animals with expanded NK cells resembled those of the control animals.

There was a significant mobilization of immune cells into the tumors from the animals that received expanded NK cells, and the ratio of immune cells to the tumor was significantly higher. Most tumors from animals that received expanded NK cells were of differentiated phenotype.

There was a significant decrease in the immune cell subsets in the peripheral blood in animals that receive tumors in the absence of NK cells; whereas animals that received NK cells had a similar immune cell subset profile to those of the control animals that did not receive tumors but received only expanded NK cells.

The tumors resected from NSG mice and BLT mice which did not receive NK cells grew very fast after dissociation and plating; and they were highly susceptible to NK cell mediated cytotoxicity indicating that the cells retained their stem like phenotype. The tumor cells also exhibited a no/low MHC class I phenotype.

In contrast, tumors resected from BLT mice that received NK cells grew much slower and they were resistant to NK cell mediated cytotoxicity, indicating that the tumor cells were of a more differentiated phenotype. The tumor cells exhibited a high expression of MHC Class I proteins.

Pancreatic tumors (Mia Paca-2; MP2). BLT animals that received MP2 stem-like tumors grew large tumors that enveloped most of the organs in the peritoneal cavity. The animals were less active.

BLT animals that were implanted with MP2 stem-like tumors and injected with expanded NK cells after one week had small tumors and the tumor did not envelope the other organs. No weight loss could be observed and they were very active similar to the control animals which were not implanted with the tumors.

BLT animals that were implanted with NK supernatant differentiated MP2 tumors did not show any tumor growth, and the pancreas resembled those of control animals with no tumor injection. No weight loss could be observed and they were very active similar to the control animals which were not implanted with the tumors.

NK cells from the peripheral blood of BLT animals which received MP2 stem like tumors and expanded NK cells, were similar to BLT animals that were implanted with differentiated MP2 tumors. The NK cells from peripheral blood mediated significant cytotoxicity against OSCSC cancer stem cells and secreted high levels of IFN-γ. In BLT animals implanted with MP2 stem like tumors which did not receive expanded NK cells, the peripheral blood cells did not mediate cytotoxicity and secreted very slight levels of IFN-γ.

In contrast liver immune cells demonstrated higher IFN-γ secretion in animals that received tumors in the absence of additional expanded NK cells; and the levels of IFN-γ from liver in animals with MP2 stem like tumors and expanded NK cells resembled those of animals that were implanted with differentiated MP2 tumors.

The tumors resected from BLT mice which did not receive NK cells grew very fast after dissociation and plating and they were highly susceptible to NK cell mediated cytotoxicity, indicating their stem like phenotype. Tumors resected from BLT mice that received NK cells grew much slower and they were resistant to NK cell mediated cytotoxicity representing their differentiated phenotype.

Overall, the in vivo data demonstrated that stem like tumors grew in the presence of fully competent human T and B cells, and that administration of activated and expanded NK cells cultured in the presence of IL-2+anti-CD16mAb+sAJ2+Osteoclasts was very effective in elimination and differentiation of these tumors, leading to much lower tumor burden, much improved peripheral blood NK numbers and function and no weight loss or wasting syndrome in fully humanized mouse model of BLT. NK supernatant differentiated tumors did not grow and did not form tumors in pancreas as seen in NSG tumor model.

What is claimed is:

1. A method for depleting cancer stem cells at a tumor site in an individual, the method comprising:
   depleting endogenous effector cells at the site; and
   administering a composition of activated NK cells at a dose effective to deplete the cancer stem cell, wherein the activated NK cells are enriched from peripheral blood and activated by culture in the presence of IL-2, anti-CD16 antibodies, sonicated probiotic bacteria, and osteoclasts.

2. The method of claim 1, wherein the cancer stem cells are carcinoma stem cells.

3. The method of claim 2, wherein the carcinoma is a squamous cell carcinoma.

4. The method of claim 2, wherein the cancer stem cells are adenocarcinoma stem cells.

5. The method of claim 1, wherein endogenous effector cells are depleted by a dose of radiation sufficient to substantially eliminate monocytes in the tumor microenvironment.

6. The method of claim 1, wherein endogenous effector cells are depleted by a dose of chemotherapy sufficient to substantially eliminate monocytes in the tumor microenvironment.

7. The method of claim 1, wherein the NK cells are autologous.

8. The method of claim 1, wherein the NK cells are allogeneic.

9. The method of claim 1, wherein the NK cells are injected at the site of the tumor.

10. The method of claim 1, further comprising administering to the individual a chemotherapeutic agent that depletes differentiated cancer cells.

11. The method of claim 10, wherein the chemotherapeutic agent is an effective dose of a taxane and N-acetylcysteine.

12. The method of claim 11, wherein the taxane is paclitaxel.

13. The method of claim 1, wherein the NK cells are cultured with sonicated probiotic bacteria at a cell:cell ratio of from 10:1 to 1:10.

14. The method of claim 1, wherein the sonicated probiotic bacteria comprise *Streptococcus thermophilus, Bifidobacterium longum*, and *Bifidobacterium breve*.

15. The method of claim 1, wherein the sonicated probiotic bacteria comprise *Streptococcus thermophilus, Bifidobacterium longum, Bifidobacterium breve, Bifidobacterium infantis, Lactobacillus acidophilus, Lactobacillus plantarum, Lactobacillus casei*, and *Lactobacillus bulgaricus*.

16. A method for depleting cancer stem cells at a tumor site in an individual, the method comprising:
   depleting endogenous effector cells at the site; and
   administering a composition of activated NK cells at a dose effective to deplete the cancer stem cell, wherein the NK cells are the NK cells are enriched from peripheral blood and activated by culture in the presence of IL-2, anti-CD16 antibodies, sonicated probiotic bacteria, and osteoclasts; and
   further sequentially administering to said individual NK cells treated with IL-2 and/or IL-12, or IFN-α, in the presence of anti-CD16 antibody to induce split anergy, in a dose effective to support differentiation of cancer stem cells.

* * * * *